United States Patent
Blumberg et al.

(10) Patent No.: US 10,513,540 B2
(45) Date of Patent: Dec. 24, 2019

(54) MODULATION OF THE IMMUNE RESPONSE

(71) Applicant: THE BRIGHAM AND WOMEN'S HOSPITAL, INC., Boston, MA (US)

(72) Inventors: Richard S. Blumberg, Waltham, MA (US); Vijay K. Kuchroo, Newton, MA (US); Yu-Hwa Huang, Boston, MA (US); Chen Zhu, Brookline, MA (US); Ana C. Anderson, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 567 days.

(21) Appl. No.: 14/418,726

(22) PCT Filed: Jul. 30, 2013

(86) PCT No.: PCT/US2013/052612
§ 371 (c)(1),
(2) Date: Jan. 30, 2015

(87) PCT Pub. No.: WO2014/022332
PCT Pub. Date: Feb. 6, 2014

(65) Prior Publication Data
US 2015/0225457 A1     Aug. 13, 2015

Related U.S. Application Data

(60) Provisional application No. 61/677,596, filed on Jul. 31, 2012.

(51) Int. Cl.
| C07K 7/06 | (2006.01) |
| C07K 7/08 | (2006.01) |
| C07K 16/28 | (2006.01) |
| C07K 16/30 | (2006.01) |
| A61K 38/10 | (2006.01) |
| A61K 39/395 | (2006.01) |
| C07K 14/705 | (2006.01) |
| A61K 39/00 | (2006.01) |

(52) U.S. Cl.
CPC .............. *C07K 7/08* (2013.01); *A61K 38/10* (2013.01); *A61K 39/3955* (2013.01); *C07K 14/70503* (2013.01); *C07K 16/2803* (2013.01); *C07K 16/30* (2013.01); *A61K 2039/505* (2013.01); *A61K 2039/507* (2013.01); *C07K 2317/31* (2013.01); *C07K 2317/73* (2013.01); *C07K 2319/30* (2013.01); *Y02A 50/463* (2018.01); *Y02A 50/466* (2018.01)

(58) Field of Classification Search
None
See application file for complete search history.

(56) References Cited

U.S. PATENT DOCUMENTS

| 6,852,320 | B2 | 2/2005 | Blumberg |
| 7,132,255 | B2 | 11/2006 | Blumberg |
| 7,470,428 | B2 | 12/2008 | Kuchroo et al. |
| 8,101,176 | B2 | 1/2012 | Kuchroo et al. |
| 8,198,412 | B2 | 6/2012 | Kojima et al. |
| 2004/0005322 | A1 | 1/2004 | Kuchroo et al. |
| 2004/0047858 | A1 | 3/2004 | Blumberg et al. |
| 2005/0191721 | A1 | 9/2005 | Kuchroo et al. |
| 2007/0110668 | A1 | 5/2007 | Markel |
| 2010/0061992 | A1 | 3/2010 | Anderson et al. |
| 2010/0247521 | A1* | 9/2010 | Jones ............... G01N 33/56988 424/131.1 |
| 2011/0189181 | A1 | 8/2011 | Utku et al. |
| 2012/0189617 | A1 | 7/2012 | Takayanagi et al. |

FOREIGN PATENT DOCUMENTS

| EP | 2417984 A1 | 2/2012 |
| WO | 1999052552 A1 | 10/1999 |
| WO | 02/12535 a1 | 2/2002 |
| WO | 2005/033144 A2 | 4/2005 |
| WO | 2007/012614 A2 | 2/2007 |
| WO | 2008060617 | 5/2008 |
| WO | 2010/125571 A1 | 11/2010 |
| WO | 2011159877 A1 | 12/2011 |
| WO | 2013082366 A1 | 6/2013 |

OTHER PUBLICATIONS

Sanchez-Fueyo et al., "Tim-3 inhibits T helper type 1-mediated auto- and alloimmune responses and promotes immunological tolerance", Nature Immunology, 4(11): 1093-1101 (2003).
Lee et al., "The inhibition of the T-cell immunoglobulin and mucin domain 3 (Tim3) pathway enhances the efficacy of tumor vaccine", Biochemical and Biophysical Research Communications, 402(1): 88-93 (2010).
Anderson et al., Science, 318(5853):1141-3 (2007) "Promotion of tissue inflammation by the immune receptor Tim-3 expressed on innate immune cells."
Barnett et al., J. Cell Biol. 108(2): 267-276 (1989) "Carcinoembryonic antigens: alternative splicing accounts for the multiple mRNAs that code for novel members of the carcinoembryonic antigen family."
Barnett et al., Mol. Cell Biol. 13(2): 1273-1282 (1993) "Human biliary glycoprotein gene: characterization of a family of novel alternatively spliced RNAs and their expressed proteins."
Bitonti et al., PNAS. 101(26): 9763-9768 (2004) "Pulmonary delivery of an erythropoietin Fc fusion protein in non-human primates through an immunoglobulin transport pathway."

(Continued)

*Primary Examiner* — G. R. Ewoldt
(74) *Attorney, Agent, or Firm* — Nixon Peabody LLP

(57) ABSTRACT

Described herein are compositions and methods for the modulation of T-cell tolerance, which can be upregulated or down regulated by concurrent enhancement or inhibition of CEACAM1/TIM3 interactions. As described herein, the discovery that CEACAM1 is a direct ligand of TIM3 and vice versa has been shown in cis and in trans. In addition, as demonstrated herein, CEACAM1 and TIM3 are co-regulated during the course of T-cell activation.

8 Claims, 25 Drawing Sheets

Specification includes a Sequence Listing.

(56) References Cited

OTHER PUBLICATIONS

Chen e al., J Immunol, 180(11):7327-7337 (2008). "Latency-Associated Peptide Identifies a Novel CD4+CD25+Regulatory T Cell Subset with TGFbeta-Mediated Function and Enhanced Suppression of Experimental Autoimmune Encephalomyelitis."
Curran et al., PNAS, 107(9):4275-7280 (2010). "PD-1 and CTLA-4 combination blockade expands infiltrating T cells and reduces regulatory T and myeloid cells within B16 melanoma tumors."
Fujita et al., A.J. Pathology, 175:1116-1123 (2009). "Carcinoembryonic Antigen-Related Cell Adhesion Molecule 1 Modulates Experimental Autoimmune Encephalomyelitis via an iNKT Cell-Dependent Mechanism ."
Gallagher, J. of Virology, 71(4):3129-3137 (1997). "A role for naturally occurring variation of the murine coronavirus spike protein in stabilizing association with the cellular receptor."
Gaur et al., Mol. Cancer, 7-46 (2008) "Altered splicing of CEACAM1 in breast cancer: identification of regulatory sequences that control splicing of CEACAM1 into long or short cytoplasmic domain isoforms."
Gray et al., Eur. J. Immunol., 38:2499-2511 (2008). "Optimising anti-tumour CD8 T-cell responses using combinations of immunomodulatory antibodies."
Iijima et al., J Exp Med, 199:471-482 (2004). "Specific Regulation of T Helper Cell 1-mediated Murine Colitis by CEACAM1".
Markel et al., J. Clin. Invest. 110(7): 943-953 (2002) "Pivotal role of CEACAM1 protein in the inhibition of activated decidual lymphocyte functions.."
Markel et al., Eur. J. Immunol. 34(8): 2138-2148 (2004) "Biological function of the soluble CEACAM1 protein and implications in TAP2-deficient patients."
Melero et al., Nature Reviews Cancer, 7:95-106 (2007). "Immunostimulatory monoclonal antibodies for cancer therapy."
Monney et al., Nature, 415(6871):536-41 (2002). "Th1-specific cell surface protein Tim-3 regulates macrophage activation and severity of an autoimmune disease."
Morales et al., J. Immunol. 163(3): 1363-1370 (1999) "Regulation of human intestinal intraepithelial lymphocyte cytolytic function by biliary glycoprotein (CD66a)."
Nakayama et al., Blood 113(16):3821-3830(2000) "Tim-3 mediates phagocytosis of apoptotic cells and cross-presentation."
Ortenberg et al., Mol. Cancer. Ther. 11(6); 1300-1310 (2012). "Novel immunotherapy for malignant melanoma with a monoclonal antibody that blocks CEACAM1 homophilic interactions."
Watt et al., Blood, 98(5): 1469-1479 (2001). "Homophilic adhesion of human CEACAM1 involves N-terminal domain interactions: structural analysis of the binding site."
Yu et al., J. Biol. Chem. 281(51): 39179-39193 (2006) "CEACAM1 (CD66a) Promotes Human Monocyte Survival via a Phosphatidylinositol 3-Kinase- and AKT-dependent Pathway."
Nagaishi et al., "Roel fo CEACAM1 as a Regulator of T Cells", Annals of the New York Academy of Sciences, 1072(1):155-175 (2006).
Ergun et al., "CEA-Related Cell Adhesion Molecule 1: A Potent Angiogenic Factor and a Major Effector of Vascular Endothelial Growth Factor", Molecular Cell, 5:311-320 (2000).
Stuart et al., "Targeting T cell costimulation in autoimmune disease", Expert Opinion on Therapeutic Targets, Informa Healthcare, 6(3):275-289 (2002).
Chen et al., "The Cell-Cell Adhesion Molecule Carcinoembryonic Antigen-Related Cellular Adhesion Molecule 1 Inhibits 1L-2 Production and Proliferation in Human T Cells by Association with Src Homology Protein-1 and Down-Regulates IL-2 Receptor", The Journal of Immunology 172(6):3544-3552(2004).
Markel et al., "Inhibition of human tumor-infiltrating lymphocyte effector functions by the homophilic carcinoembryonic cell adhesion molecule 1 interactions." The Journal of Immunology 177(9):6062-6071 (2006).
Nakajima et al., "Activation-induced expression of carcinoembryonic antigen-cell adhesion molecule 1 regulates mouse T lymphocyte function." The Journal of Immunology 168(3):1028-1035 (2002).
Ngiow et al., "Prospects for TIM3-Targeted Antitumor Immunotherapy", Cancer Res 71(21) 6567-6571 (2011).
Sapoznik et al., "Novel anti-melanoma immunotherapies: disarming tumor escape mechanisms", Clin Dev Immunol 2012: 818214 (2012).

\* cited by examiner

Peptide 1: linear
-Cys-Pro-Val-Phe-Glu-Cys-Gly-Asn-Val-Val-Leu-Arg-Thr-Asp-Glu-Arg-Asp-Val-Asn-Tyr-77

Peptide 2: non-linear
-Cys-Pro-Val-Phe-Glu-Ser-Gly-Ser-Gly-Arg-Ile-Gln-Glu-Pro-Gly-Ile-Met-119

SEQUENCE LISTING

<160> NUMBER OF SEQ ID NOS: 34

<210> SEQ ID NO 1
<211> LENGTH: 301
<212> TYPE: PRT
<213> ORGANISM: Homo sapiens

<400> SEQUENCE: 1

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 2
<211> LENGTH: 301
<212> TYPE: PRT
<213> ORGANISM: Homo sapiens

<400> SEQUENCE: 2

```
Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
                35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
                115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
                180                 185                 190

Arg Asp Ser Gly Ala Thr Ile Arg Ile Gly Ile Tyr Ile Gly Ala Gly
                195                 200                 205

Ile Cys Ala Gly Leu Ala Leu Ala Leu Ile Phe Gly Ala Leu Ile Phe
                210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
                260                 265                 270

Glu Val Glu Glu Pro Asn Glu Tyr Tyr Cys Tyr Val Ser Ser Arg Gln
                275                 280                 285

Gln Pro Ser Gln Pro Leu Gly Cys Arg Phe Ala Met Pro
                290                 295                 300
```

<210> SEQ ID NO 3
<211> LENGTH: 197
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Phe Ser Gly Leu Thr Leu Asn Cys Val Leu Leu Leu Leu Gln Leu
1               5                   10                  15

Leu Leu Ala Arg Ser Leu Glu Asp Gly Tyr Lys Val Glu Val Gly Lys
            20                  25                  30

Asn Ala Tyr Leu Pro Cys Ser Tyr Thr Leu Pro Thr Ser Gly Thr Leu
                35                  40                  45
```

```
Val Pro Met Cys Trp Gly Lys Gly Phe Cys Pro Trp Ser Gln Cys Thr
 50                  55                  60

Asn Glu Leu Leu Arg Thr Asp Glu Arg Asn Val Thr Tyr Gln Lys Ser
 65                  70                  75                  80

Ser Arg Tyr Gln Leu Lys Gly Asp Leu Asn Lys Gly Asp Val Ser Leu
                 85                  90                  95

Ile Ile Lys Asn Val Thr Leu Asp Asp His Gly Thr Tyr Cys Cys Arg
                100                 105                 110

Ile Gln Phe Pro Gly Leu Met Asn Asp Lys Lys Leu Glu Leu Lys Leu
            115                 120                 125

Asp Ile Lys Ala Gly Tyr Ser Cys Lys Lys Lys Leu Ser Ser Leu
        130                 135                 140

Ser Leu Ile Thr Leu Ala Asn Leu Pro Pro Gly Gly Leu Ala Asn Ala
145                 150                 155                 160

Gly Ala Val Arg Ile Arg Ser Glu Glu Asn Ile Tyr Thr Ile Glu Glu
                165                 170                 175

Asn Val Tyr Glu Val Glu Asn Ser Asn Glu Tyr Tyr Cys Tyr Val Asn
                180                 185                 190

Ser Gln Gln Pro Ser
            195

<210> SEQ ID NO 4
<211> LENGTH: 281
<212> TYPE: PRT
<213> ORGANISM: Mus musculus

<400> SEQUENCE: 4

Met Phe Ser Gly Leu Thr Leu Asn Cys Val Leu Leu Leu Gln Leu
 1               5                  10                  15

Leu Leu Ala Arg Ser Leu Glu Asp Gly Tyr Lys Val Glu Val Gly Lys
                 20                  25                  30

Asn Ala Tyr Leu Pro Cys Ser Tyr Thr Leu Pro Thr Ser Gly Thr Leu
                 35                  40                  45

Val Pro Met Cys Trp Gly Lys Gly Phe Cys Pro Trp Ser Gln Cys Thr
 50                  55                  60

Asn Glu Leu Leu Arg Thr Asp Glu Arg Asn Val Thr Tyr Gln Lys Ser
 65                  70                  75                  80

Ser Arg Tyr Gln Leu Lys Gly Asp Leu Asn Lys Gly Asp Val Ser Leu
                 85                  90                  95

Ile Ile Lys Asn Val Thr Leu Asp Asp His Gly Thr Tyr Cys Cys Arg
                100                 105                 110

Ile Gln Phe Pro Gly Leu Met Asn Asp Lys Lys Leu Glu Leu Lys Leu
            115                 120                 125

Asp Ile Lys Ala Ala Lys Val Thr Pro Ala Gln Thr Ala His Gly Asp
        130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
        195                 200                 205

Ile Ile Gly Val Leu Ile Leu Lys Trp Tyr Ser Cys Lys Lys Lys Lys
210                 215                 220
```

```
Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
            275                 280

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ser His Gly Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Ile Ser Ser Gly Gly Thr Tyr Thr Tyr Tyr Pro Asp Ser Val Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Asp Phe Asp Tyr Asp Ala Ala Trp Phe Ala Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ala Asn Ser Ser Val Ser Tyr Met Tyr
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Leu Thr Ser Asn Leu Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Trp Ser Ser Asn Pro Pro Thr
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Phe Tyr Gly Met Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Asp Tyr Tyr Leu Tyr
1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Phe Ser Gly Gly Gly Asn Tyr Thr Tyr Tyr Pro Asp Ser Val Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ile Ser Val Gly Gly Gly Asn Thr Ser Tyr Pro Asp Ser Val Lys
1               5                   10                  15

Gly
```

```
<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Gly Gly Leu Pro Phe Tyr Ala Met Asp Tyr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Leu Thr Thr Gly Pro Ala Trp Phe Ala Tyr
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Val Ser Ser Ser Ile Ser Ser Ser Asn Leu His
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ser Ser Gln Ser Leu Leu Asn Ser Ser Asn Gln Lys Asn Tyr Leu
1               5                   10                  15

Ala

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Ser Gln Lys Ile Ser Gly Tyr Leu Ser
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Ser Val Ser Ser Ser Ile Ser Ser Ser Asn Leu His
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Ala Ser Thr Arg Glu Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ser Thr Leu Asp Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Trp Ser Ser His Pro Phe Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln His Tyr Ser Thr Pro Trp Thr
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Gln Tyr Ala Ser Ser Leu Met Tyr Thr
1               5                   10
```

<210> SEQ ID NO 26
<211> LENGTH: 417
<212> TYPE: PRT
<213> ORGANISM: Homo sapiens

<400> SEQUENCE: 26

| Met | Gly | His | Leu | Ser | Ala | Pro | Leu | His | Arg | Val | Arg | Val | Pro | Trp | Gln |
|---|---|---|---|---|---|---|---|---|---|---|---|---|---|---|---|
| 1 | | | | 5 | | | | | 10 | | | | | 15 | |

| Gly | Leu | Leu | Leu | Thr | Ala | Ser | Leu | Leu | Thr | Phe | Trp | Asn | Pro | Pro | Thr |
|---|---|---|---|---|---|---|---|---|---|---|---|---|---|---|---|
| | | | 20 | | | | | 25 | | | | | 30 | | |

| Thr | Ala | Gln | Leu | Thr | Thr | Glu | Ser | Met | Pro | Phe | Asn | Val | Ala | Glu | Gly |
|---|---|---|---|---|---|---|---|---|---|---|---|---|---|---|---|
| | | | 35 | | | | | 40 | | | | | 45 | | |

| Lys | Glu | Val | Leu | Leu | Leu | Val | His | Asn | Leu | Pro | Gln | Gln | Leu | Phe | Gly |
|---|---|---|---|---|---|---|---|---|---|---|---|---|---|---|---|
| | 50 | | | | | 55 | | | | | 60 | | | | |

| Tyr | Ser | Trp | Tyr | Lys | Gly | Glu | Arg | Val | Asp | Gly | Asn | Arg | Gln | Ile | Val |
|---|---|---|---|---|---|---|---|---|---|---|---|---|---|---|---|
| 65 | | | | | 70 | | | | | 75 | | | | | 80 |

| Gly | Tyr | Ala | Ile | Gly | Thr | Gln | Gln | Ala | Thr | Pro | Gly | Pro | Ala | Asn | Ser |
|---|---|---|---|---|---|---|---|---|---|---|---|---|---|---|---|
| | | | | 85 | | | | | 90 | | | | | 95 | |

| Gly | Arg | Glu | Thr | Ile | Tyr | Pro | Asn | Ala | Ser | Leu | Leu | Ile | Gln | Asn | Val |
|---|---|---|---|---|---|---|---|---|---|---|---|---|---|---|---|
| | | | 100 | | | | | 105 | | | | | 110 | | |

| Thr | Gln | Asn | Asp | Thr | Gly | Phe | Tyr | Thr | Leu | Gln | Val | Ile | Lys | Ser | Asp |
|---|---|---|---|---|---|---|---|---|---|---|---|---|---|---|---|
| | | | 115 | | | | | 120 | | | | | 125 | | |

| Leu | Val | Asn | Glu | Glu | Ala | Thr | Gly | Gln | Phe | His | Val | Tyr | Pro | Glu | Leu |
|---|---|---|---|---|---|---|---|---|---|---|---|---|---|---|---|
| | 130 | | | | | 135 | | | | | 140 | | | | |

| Pro | Lys | Pro | Ser | Ile | Ser | Ser | Asn | Asn | Ser | Asn | Pro | Val | Glu | Asp | Lys |
|---|---|---|---|---|---|---|---|---|---|---|---|---|---|---|---|
| 145 | | | | | 150 | | | | | 155 | | | | | 160 |

| Asp | Ala | Val | Ala | Phe | Thr | Cys | Glu | Pro | Glu | Thr | Gln | Asp | Thr | Thr | Tyr |
|---|---|---|---|---|---|---|---|---|---|---|---|---|---|---|---|
| | | | | 165 | | | | | 170 | | | | | 175 | |

| Leu | Trp | Trp | Ile | Asn | Asn | Gln | Ser | Leu | Pro | Val | Ser | Pro | Arg | Leu | Gln |
|---|---|---|---|---|---|---|---|---|---|---|---|---|---|---|---|
| | | | 180 | | | | | 185 | | | | | 190 | | |

| Leu | Ser | Asn | Gly | Asn | Arg | Thr | Leu | Thr | Leu | Leu | Ser | Val | Thr | Arg | Asn |
|---|---|---|---|---|---|---|---|---|---|---|---|---|---|---|---|
| | | | 195 | | | | | 200 | | | | | 205 | | |

| Asp | Thr | Gly | Pro | Tyr | Glu | Cys | Glu | Ile | Gln | Asn | Pro | Val | Ser | Ala | Asn |
|---|---|---|---|---|---|---|---|---|---|---|---|---|---|---|---|
| | 210 | | | | | 215 | | | | | 220 | | | | |

| Arg | Ser | Asp | Pro | Val | Thr | Leu | Asn | Val | Thr | Tyr | Gly | Pro | Asp | Thr | Pro |
|---|---|---|---|---|---|---|---|---|---|---|---|---|---|---|---|
| 225 | | | | | 230 | | | | | 235 | | | | | 240 |

| Thr | Ile | Ser | Pro | Ser | Asp | Thr | Tyr | Tyr | Arg | Pro | Gly | Ala | Asn | Leu | Ser |
|---|---|---|---|---|---|---|---|---|---|---|---|---|---|---|---|
| | | | | 245 | | | | | 250 | | | | | 255 | |

| Leu | Ser | Cys | Tyr | Ala | Ala | Ser | Asn | Pro | Pro | Ala | Gln | Tyr | Ser | Trp | Leu |
|---|---|---|---|---|---|---|---|---|---|---|---|---|---|---|---|
| | | | 260 | | | | | 265 | | | | | 270 | | |

| Ile | Asn | Gly | Thr | Phe | Gln | Gln | Ser | Thr | Gln | Glu | Leu | Phe | Ile | Pro | Asn |
|---|---|---|---|---|---|---|---|---|---|---|---|---|---|---|---|
| | | | 275 | | | | | 280 | | | | | 285 | | |

| Ile | Thr | Val | Asn | Asn | Ser | Gly | Ser | Tyr | Thr | Cys | His | Ala | Asn | Asn | Ser |
|---|---|---|---|---|---|---|---|---|---|---|---|---|---|---|---|
| | 290 | | | | | 295 | | | | | 300 | | | | |

| Val | Thr | Gly | Cys | Asn | Arg | Thr | Thr | Val | Lys | Thr | Ile | Ile | Val | Thr | Glu |
|---|---|---|---|---|---|---|---|---|---|---|---|---|---|---|---|
| 305 | | | | | 310 | | | | | 315 | | | | | 320 |

| Leu | Ser | Pro | Val | Val | Ala | Lys | Pro | Gln | Ile | Lys | Ala | Ser | Lys | Thr | Thr |
|---|---|---|---|---|---|---|---|---|---|---|---|---|---|---|---|
| | | | | 325 | | | | | 330 | | | | | 335 | |

| Val | Thr | Gly | Asp | Lys | Asp | Ser | Val | Asn | Leu | Thr | Cys | Ser | Thr | Asn | Asp |
|---|---|---|---|---|---|---|---|---|---|---|---|---|---|---|---|
| | | | 340 | | | | | 345 | | | | | 350 | | |

| Thr | Gly | Ile | Ser | Ile | Arg | Trp | Phe | Phe | Lys | Asn | Gln | Ser | Leu | Pro | Ser |
|---|---|---|---|---|---|---|---|---|---|---|---|---|---|---|---|
| | | | 355 | | | | | 360 | | | | | 365 | | |

| Ser | Glu | Arg | Met | Lys | Leu | Ser | Gln | Gly | Asn | Thr | Thr | Leu | Ser | Ile | Asn |
|---|---|---|---|---|---|---|---|---|---|---|---|---|---|---|---|
| | 370 | | | | | 375 | | | | | 380 | | | | |

```
Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Cys
            405                 410                 415

Lys

<210> SEQ ID NO 27
<211> LENGTH: 321
<212> TYPE: PRT
<213> ORGANISM: Homo sapiens

<400> SEQUENCE: 27

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
290                 295                 300

Val Thr Gly Cys Asn Arg Thr Thr Val Lys Thr Ile Ile Val Thr Gly
305                 310                 315                 320

Lys
```

<210> SEQ ID NO 28
<211> LENGTH: 351
<212> TYPE: PRT
<213> ORGANISM: Homo sapiens

<400> SEQUENCE: 28

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Ser Pro Val Leu Gly Glu Asp Glu Ala Val Pro Gly Gln His His Pro
                325                 330                 335

Gln His Lys Pro Cys Gln Glu Gly Gly Cys Trp Asp Val Leu Val
            340                 345                 350

<210> SEQ ID NO 29
<211> LENGTH: 526
<212> TYPE: PRT
<213> ORGANISM: Homo sapiens

<400> SEQUENCE: 29

```
Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Val His Asn Leu Pro Gln Gln Leu Phe Gly
50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
                85                  90                  95

Gly Arg Glu Thr Ile Tyr Pro Asn Ala Ser Leu Leu Ile Gln Asn Val
                100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
                180                 185                 190

Leu Ser Asn Gly Asn Arg Thr Leu Thr Leu Leu Ser Val Thr Arg Asn
            195                 200                 205

Asp Thr Gly Pro Tyr Glu Cys Glu Ile Gln Asn Pro Val Ser Ala Asn
        210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
                260                 265                 270

Ile Asn Gly Thr Phe Gln Gln Ser Thr Gln Glu Leu Phe Ile Pro Asn
            275                 280                 285

Ile Thr Val Asn Asn Ser Gly Ser Tyr Thr Cys His Ala Asn Asn Ser
        290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415
```

```
Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Arg Ala Ser Asp Gln Arg
    450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510

Leu Thr Ala Thr Glu Ile Ile Tyr Ser Glu Val Lys Lys Gln
        515                 520                 525

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Pro Val Phe Glu Cys Gly Asn Val Val Leu Arg Thr Asp Glu Arg
1               5                   10                  15

Asp Val Asn Tyr
            20

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Pro Val Phe Glu Ser Gly Ser Gly Arg Ile Gln Glu Pro Gly Ile
1               5                   10                  15

Met

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Gly Ser Gly
1

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 33

His His His His His His
1               5

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Pro Val Phe Glu Ser Gly Ser Gly Ile Gln Ile Pro Gly Ile Met
1               5                   10                  15

Asn
```

MODULATION OF THE IMMUNE RESPONSE

CROSS-REFERENCE TO RELATED APPLICATIONS

This application is a 35 U.S.C. 371 National Stage Application of International Application No. PCT/US2013/052612 filed on Jul. 30, 2013, which designates the United States, and which claims benefit under 35 U.S.C. § 119(e) of U.S. Provisional Patent Application Ser. No. 61/677,596 filed on Jul. 31, 2012, the contents of each of which are herein incorporated by reference in its entirety.

GOVERNMENT SUPPORT

This invention was made with government support under Grant No. NIKDK51362, awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 30, 2015, is named 043214-073952-US_SL.txt and is 30,190 bytes in size.

FIELD OF THE INVENTION

The present invention relates to molecular immunology and cell biology. More specifically, the present embodiments provide for the modulation of the T-cell tolerance immune response by harnessing the interactions of TIM3 and CEACAM1, which are ligands for each other.

BACKGROUND

The immune system protects the body from foreign invaders and diseased cells; but immune disorders, particularly those associated with T-cell tolerance, such as cancers, can wreak havoc. According to the most recent data from the World Health Organization, ten million people around the world were diagnosed with the cancer in 2000, and six million died from it. Moreover, statistics indicate that the cancer incidence rate is on the rise around the globe. In America, for example, projections suggest that fifty percent of those alive today will be diagnosed with some form of cancer at some point in their lives.

T-cell tolerance is also implicated in immune suppression that can be desirable, for example, in autoimmune diseases and in organ transplant situations, wherein an overactive immune response can cause great permanent damage to the afflicted individual and or donor organ. More specifically, autoimmune disorders are caused by dysfunctional immune responses directed against the body's own tissues, resulting in chronic, multisystem impairments that differ in clinical manifestations, course, and outcome. Autoimmune diseases are on the rise in the U.S. and around the world. In the U.S. alone, some fifty million are affected, and autoimmune disease is one of the top ten causes of death in women under the age of 65, is the second highest cause of chronic illness, and the top cause of morbidity in women.

Hence, there remains an urgent need for compositions and approaches to treating T-cell tolerance mediated immune disorders.

SUMMARY

Provided herein are compositions and methods for the modulation of T-cell tolerance, which can be upregulated or down regulated by concurrent enhancement or inhibition of CEACAM1/TIM3 interactions. More specifically, demonstrated herein is the discovery that CEACAM1 is a direct ligand of TIM3 and vice versa. As described herein, this association has been shown in cis (interactions between CEACAM1 and TIM3 on the same cell) and in trans (CEACAM1 on one cell binding to TIM3 on another cell). In addition, as demonstrated herein, CEACAM1 and TIM3 are co-regulated during the course of T-cell activation. Specifically, in the absence of CEACAM1, TIM3 is not expressed on activated T-cells, and T cell tolerance is not induced. CEACAM1 and TIM3 have both been linked to the regulation of T-cells. This, the coordinate regulation of TIM3 expression by CEACAM1, and the present discovery described herein that CEACAM1 and TIM3 act as ligands for each other, indicate that CEACAM1 and TIM3 are interacting players involved in the development of tolerance or generation of hypo-responsive T-cells during the course of an active immune response.

As demonstrated herein, CEACAM1 binds to TIM3 and also regulates its expression. This binding interaction and coordinate regulation of expression is linked to the development of T-cell tolerance, as described herein. This indicates that CEACAM1-related ligands for TIM3 and, as a corollary, TIM3-related ligands for CEACAM1, can be developed and utilized for the modulation of each other. This is useful when one seeks to increase T-cell tolerance, for example, to treat autoimmune diseases or in transplantation situations. In contrast, blockade of the interactions between TIM3 and CEACAM1 provides a means to abrogate tolerance, which is useful, for example, to treat cancers. As such, this knowledge provides an opportunity for a unique means to regulate an important series of checkpoints associated with T-cell tolerance. As described herein, useful compositions include biologics or small molecules that specifically target the function or interaction between these two molecules, for example, at the interaction site.

Thus, there are several aspects to the CEACAM1/TIM3 interaction that are implicated in the compositions and methods described herein as targets for modulating T-cell tolerance: CEACAM1 interacts with TIM3 via heterophilic trans binding; CEACAM1 and TIM3 interact in cis, in the same cell; CEACAM1 homophilic binding in trans leads to up-regulation of TIM3; in the absence of CEACAM1, TIM3 is not expressed Inhibiting any of these interactions can abrogate the development of T-cell tolerance.

Accordingly, in some aspects, described herein are compositions for modulating the interaction between TIM3 and CEACAM1, the compositions comprising a bispecific agent comprising binding sites specific for TIM3 and CEACAM1. In some embodiments of these and all such aspects described herein, the bispecific agent binds TIM3 and CEACAM1 and inhibits signaling mediated by the interaction of TIM3 and CEACAM1. In some embodiments of these and all such aspects described herein, the bispecific agent binds TIM3 and CEACAM1 and increases signaling mediated by the interaction of TIM3 and CEACAM1. In some embodiments of these and all such aspects described herein, the composition modulates the interaction between TIM3 and CEACAM1 on the same cell. For example, homophile trans interactions between two CEACAM1 molecules can upregulate CEACAM1 and TIM-3 cis or trans interactions. In some embodiments of these and all such aspects described herein, the bispecific agent modulates the interaction between TIM3 on a first cell and CEACAM1 on a second cell. In some embodiments of these and all such aspects described herein, the bispecific agent comprises an antibody or antigen binding portion thereof that specifically binds TIM3 and an antibody or antigen binding portion thereof that specifically binds CEACAM1.

In some aspects, provided herein are compositions for modulating T cell tolerance, the composition comprising an agent that modulates the interaction of CEACAM1 with TIM3. In some embodiments, the composition inhibits the interaction of CEACAM1 with TIM3 and inhibits T cell tolerance. In other embodiments, the composition enhances or mimics the interaction of CEACAM1 with TIM3 and promotes T cell tolerance.

In some embodiments of these aspects and all such aspects described herein, the agent comprises a proteo-mimetic of CEACAM1 that binds to TIM3. In some embodiments, the proteo-mimetic binds to TIM3 and activates signaling mediated by the interaction of TIM3 and CEACAM1. In some embodiments, the proteo-mimetic binds to TIM3 and inhibits signaling mediated by the interaction of TIM3 and CEACAM1.

In some embodiments of these and all such aspects described herein, the agent comprises a proteo-mimetic of TIM3 that binds to CEACAM1. In some embodiments of these and all such aspects described herein, the proteo-mimetic of TIM3 comprises SEQ ID NO: 30 or SEQ ID NO: 31. In some embodiments, the proteo-mimetic binds to CEACAM1 and activates signaling mediated by the interaction of TIM3 and CEACAM1. In some embodiments, the proteo-mimetic binds to CEACAM1 and inhibits signaling mediated by the interaction of TIM3 and CEACAM1.

In some embodiments of these and all such aspects described herein, the agent comprises a proteo-mimetic of CEACAM1 that binds to TIM3 and a proteo-mimetic of TIM3 that binds to CEACAM1.

In some embodiments of these and all such aspects described herein, the composition comprises a polypeptide that specifically binds TIM-3. In some embodiments of these and all such aspects described herein, the composition comprises a polypeptide that specifically binds CEACAM1. In some embodiments, the polypeptide that specifically binds TIM3 comprises an antibody or antigen binding portion thereof. In some embodiments, the polypeptide that specifically binds CEACAM1 comprises an antibody or antigen binding portion thereof. In some embodiments of these and all such aspects described herein, the composition comprises an antibody or antigen-binding portion thereof that specifically binds TIM3 and an antibody or antigen-binding portion thereof that specifically binds CEACAM1.

Each of the embodiments of the compositions described herein can be used in methods of modulating the interaction between TIM3 and CEACAM1 and/or in methods of modulating T cell tolerance.

Accordingly, in some aspects, described herein are methods of modulating interaction of CEACAM1 with TIM3, such methods comprising contacting a cell with an agent that binds CEACAM1 and/or TIM3 and modulates binding of CEACAM1 to TIM3. In some embodiments of these and all such aspects described herein, such an agent increases signaling mediated by CEACAM1 interaction with TIM3. Such increasing or enhancing of the signaling mediated by CEACAM1 interaction with TIM3 can be used, in some embodiments, in the treatment or amelioration of autoimmunity. In some embodiments of these and all such aspects described herein, the agent inhibits signaling mediated by CEACAM1 interaction with TIM3. In some embodiments of these and all such aspects described herein, the agent comprises binding sites specific for both CEACAM1 and TIM3. In some embodiments of these and all such aspects described herein, the agent comprises a bispecific polypeptide agent comprising binding sites specific for TIM3 and CEACAM1. In some embodiments of these and all such aspects described herein, the bispecific polypeptide agent comprises an antibody or antigen binding portion thereof that specifically binds TIM3 and an antibody or antigen binding portion thereof that specifically binds CEACAM1.

Also provided herein, in some aspects, are methods of modulating T cell tolerance, the methods comprising administering an agent that modulates the interaction of TIM3 with CEACAM1. In some embodiments of these aspects and all such aspects described herein, the agent promotes the interaction of TIM3 with CEACAM1 and promotes T cell tolerance. In some embodiments of these and all such aspects described herein, the agent inhibits the interaction of TIM3 with CEACAM1 and inhibits T cell tolerance. Such inhibition can be used, in some embodiments, for inhibiting tumor or cancer growth and progression. In some embodiments of these and all such aspects described herein, the agent comprises binding sites specific for both CEACAM1 and TIM3. In some embodiments of these and all such aspects described herein, the agent comprises a bispecific polypeptide agent comprising binding sites specific for TIM3 and CEACAM1. In some embodiments of these and all such aspects described herein, the bispecific polypeptide agent comprises an antibody or antigen binding portion thereof that specifically binds TIM3 and an antibody or antigen binding portion thereof that specifically binds CEACAM1.

Provided herein, in some aspects, are compositions for modulating the interaction between TIM3 and CEACAM1, the compositions comprising a bispecific agent comprising binding sites specific for TIM3 and CEACAM1.

In some embodiments of these aspects and all such aspects described herein, the bispecific agent binds TIM3 and CEACAM1 and inhibits signaling mediated by the interaction of TIM3 and CEACAM1.

In some embodiments of these aspects and all such aspects described herein, the bispecific agent binds TIM3 and CEACAM1 and increases signaling mediated by the interaction of TIM3 and CEACAM1.

In some embodiments of these aspects and all such aspects described herein, the bispecific agent modulates the interaction between TIM3 and CEACAM1 on the same cell.

In some embodiments of these aspects and all such aspects described herein, the bispecific agent modulates the interaction between TIM3 on a first cell and CEACAM1 on a second cell.

In some embodiments of these aspects and all such aspects described herein, the bispecific agent comprises an antibody or antigen binding portion thereof that specifically binds TIM3 and an antibody or antigen binding portion thereof that specifically binds CEACAM1.

Provided herein, in some aspects, are compositions for modulating T cell tolerance, the compositions comprising an agent that modulates the interaction of CEACAM1 with TIM3.

In some embodiments of these aspects and all such aspects described herein, the agent inhibits the interaction of CEACAM1 with TIM3 and inhibits T cell tolerance.

In some embodiments of these aspects and all such aspects described herein, the agent enhances or mimics the interaction of CEACAM1 with TIM3 and promotes T cell tolerance.

In some embodiments of these aspects and all such aspects described herein, the agent comprises a proteo-mimetic of CEACAM1 that binds to TIM3. In some embodiments of these aspects and all such aspects described herein, the proteo-mimetic binds to TIM3 and activates or mimics signaling mediated by the interaction of TIM3 and CEACAM1. In some embodiments of these aspects and all such aspects described herein, the proteo-mimetic binds to TIM3 and inhibits signaling mediated by the interaction of TIM3 and CEACAM1.

In some embodiments of these aspects and all such aspects described herein, the agent comprises a proteo-mimetic of TIM3 that binds to CEACAM1. In some embodiments of these aspects and all such aspects described herein, the proteo-mimetic binds to CEACAM1 and activates signaling mediated by the interaction of TIM3 and CEACAM1. In some embodiments of these aspects and all such aspects described herein, the proteo-mimetic binds to CEACAM1 and inhibits signaling mediated by the interaction of TIM3 and CEACAM1. In some embodiments of these aspects and all such aspects described herein, the proteo-mimetic binds comprises SEQ ID NO: 30 or SEQ ID NO: 31.

In some embodiments of these aspects and all such aspects described herein, the agent comprises a proteo-mimetic of CEACAM1 that binds to TIM3 and a proteo-mimetic of TIM3 that binds to CEACAM1.

In some embodiments of these aspects and all such aspects described herein, wherein the agent comprises a polypeptide that specifically binds TIM-3. In some embodiments of these aspects and all such aspects described herein, the polypeptide that specifically binds TIM3 comprises an antibody or antigen binding portion thereof.

In some embodiments of these aspects and all such aspects described herein, the agent comprises a polypeptide that specifically binds CEACAM1. In some embodiments of these aspects and all such aspects described herein, the polypeptide that specifically binds CEACAM1 comprises an antibody or antigen binding portion thereof.

In some embodiments of these aspects and all such aspects described herein, the agent comprises an antibody or antigen-binding portion thereof that specifically binds TIM3 and an antibody or antigen-binding portion thereof that specifically binds CEACAM1.

Also provided herein, in some aspects, are methods of modulating the interaction of CEACAM1 with TIM3, the methods comprising contacting a cell with an agent that binds CEACAM1 and/or TIM3 and modulates binding of CEACAM1 to TIM3.

In some embodiments of these aspects and all such aspects described herein, the agent increases signaling mediated by CEACAM1 interaction with TIM3.

In some embodiments of these aspects and all such aspects described herein, the agent inhibits signaling mediated by CEACAM1 interaction with TIM3.

In some embodiments of these aspects and all such aspects described herein, the agent comprises binding sites specific for both CEACAM1 and TIM3.

In some embodiments of these aspects and all such aspects described herein, the agent comprises a bispecific polypeptide agent comprising binding sites specific for TIM3 and CEACAM1.

In some embodiments of these aspects and all such aspects described herein, the bispecific polypeptide agent comprises an antibody or antigen binding portion thereof that specifically binds TIM3 and an antibody or antigen binding portion thereof that specifically binds CEACAM1.

Also provided herein, in some aspects, are methods of modulating T cell tolerance, the methods comprising administering an agent that modulates the interaction of TIM3 with CEACAM1.

In some embodiments of these aspects and all such aspects described herein, the agent increases signaling mediated by CEACAM1 interaction with TIM3 and increases T cell tolerance.

In some embodiments of these aspects and all such aspects described herein, the agent inhibits signaling mediated by CEACAM1 interaction with TIM3.

In some embodiments of these aspects and all such aspects described herein, the agent comprises binding sites specific for both CEACAM1 and TIM3.

Also provided herein, in some aspects, are methods of modulating T cell tolerance in a subject in need thereof, the methods comprising administering an effective amount of an agent that modulates the interaction of TIM3 with CEACAM1.

In some embodiments of these aspects and all such aspects described herein, the agent increases or mimics signaling mediated by CEACAM1 interaction with TIM3 and increases T cell tolerance. In some embodiments of these aspects and all such aspects described herein, the subject has an autoimmune disorder. In some embodiments of these aspects and all such aspects described herein, the subject is a transplant recipient.

In some embodiments of these aspects and all such aspects described herein, the agent inhibits signaling mediated by CEACAM1 interaction with TIM3 and inhibits T cell tolerance. In some embodiments of these aspects and all such aspects described herein, the subject has cancer or a tumor. In some embodiments of these aspects and all such aspects described herein, the subject is a transplant recipient In some embodiments of these aspects and all such aspects described herein, the agent comprises a proteo-mimetic of CEACAM1 that binds to TIM3. In some embodiments of these aspects and all such aspects described herein, the proteo-mimetic binds to TIM3 and activates signaling mediated by the interaction of TIM3 and CEACAM1. In some embodiments of these aspects and all such aspects described herein, the proteo-mimetic binds to TIM3 and inhibits signaling mediated by the interaction of TIM3 and CEACAM1.

In some embodiments of these aspects and all such aspects described herein, the agent comprises a proteo-mimetic of TIM3 that binds to CEACAM1. In some embodiments of these aspects and all such aspects described herein, the proteo-mimetic binds to CEACAM1 and activates or mimics signaling mediated by the interaction of TIM3 and CEACAM1. In some embodiments of these aspects and all such aspects described herein, the proteo-mimetic binds to CEACAM1 and inhibits signaling mediated by the interaction of TIM3 and CEACAM1. In some embodiments of these aspects and all such aspects described herein, the proteo-mimetic binds comprises SEQ ID NO: 30 or SEQ ID NO: 31. In some embodiments of these aspects and all such aspects described herein, the agent comprises a proteo-mimetic of CEACAM1 that binds to TIM3 and a proteo-mimetic of TIM3 that binds to CEACAM1.

In some embodiments of these aspects and all such aspects described herein, the agent comprises a polypeptide that specifically binds TIM-3. In some embodiments of these aspects and all such aspects described herein, the agent comprises a polypeptide that specifically binds CEACAM1. In some embodiments of these aspects and all such aspects described herein, the polypeptide that specifically binds TIM3 comprises an antibody or antigen binding portion thereof. In some embodiments of these aspects and all such aspects described herein, the polypeptide that specifically binds CEACAM1 comprises an antibody or antigen binding portion thereof. In some embodiments of these aspects and all such aspects described herein, the agent comprises an antibody or antigen-binding portion thereof that specifically binds TIM3 and an antibody or antigen-binding portion thereof that specifically binds CEACAM1. In some embodiments of these aspects and all such aspects described herein, the agent comprises binding sites specific for both CEACAM1 and TIM3.

Provided herein, in some aspects, are agents that modulates the interaction of TIM3 with CEACAM1 for use in modulating T cell tolerance in a subject.

In some embodiments of these aspects and all such aspects described herein, the agent the agent increases or mimics signaling mediated by CEACAM1 interaction with TIM3 and increases T cell tolerance. In some embodiments of these aspects and all such aspects described herein, the subject has an autoimmune disorder. In some embodiments of these aspects and all such aspects described herein, the subject is a transplant recipient.

In some embodiments of these aspects and all such aspects described herein, the agent inhibits signaling mediated by CEACAM1 interaction with TIM3 and inhibits T cell tolerance. In some embodiments of these aspects and all such aspects described herein, the subject has cancer or a tumor. In some embodiments of these aspects and all such aspects described herein, the subject is a transplant recipient.

In some embodiments of these aspects and all such aspects described herein, the agent comprises a proteo-mimetic of CEACAM1 that binds to TIM3. In some embodiments of these aspects and all such aspects described herein, the proteo-mimetic binds to TIM3 and activates signaling mediated by the interaction of TIM3 and CEACAM1. In some embodiments of these aspects and all such aspects described herein, the proteo-mimetic binds to TIM3 and inhibits signaling mediated by the interaction of TIM3 and CEACAM1. In some embodiments of these aspects and all such aspects described herein, the agent comprises a proteo-mimetic of TIM3 that binds to CEACAM1. In some embodiments of these aspects and all such aspects described herein, the proteo-mimetic binds to CEACAM1 and activates or mimics signaling mediated by the interaction of TIM3 and CEACAM1. In some embodiments of these aspects and all such aspects described herein, the proteo-mimetic binds to CEACAM1 and inhibits signaling mediated by the interaction of TIM3 and CEACAM1. In some embodiments of these aspects and all such aspects described herein, the proteo-mimetic binds comprises SEQ ID NO: 30 or SEQ ID NO: 31. In some embodiments of these aspects and all such aspects described herein, the agent comprises a proteo-mimetic of CEACAM1 that binds to TIM3 and a proteo-mimetic of TIM3 that binds to CEACAM1.

In some embodiments of these aspects and all such aspects described herein, the agent comprises a polypeptide that specifically binds TIM-3. In some embodiments of these aspects and all such aspects described herein, the agent comprises a polypeptide that specifically binds CEACAM1. In some embodiments of these aspects and all such aspects described herein, the polypeptide that specifically binds TIM3 comprises an antibody or antigen binding portion thereof. In some embodiments of these aspects and all such aspects described herein, the polypeptide that specifically binds CEACAM1 comprises an antibody or antigen binding portion thereof.

In some embodiments of these aspects and all such aspects described herein, the agent comprises an antibody or antigen-binding portion thereof that specifically binds TIM3 and an antibody or antigen-binding portion thereof that specifically binds CEACAM1.

BRIEF DESCRIPTION OF THE DRAWINGS

FIG. 5A shows that CD4$^+$Vβ8$^+$ T cells are deleted by SEB treatment in presence or absence of murine CEACAM1-N domain-Fc fusion protein demonstrating T cell receptor engagement by SEB is not significantly influenced by fusion protein. FIG. 5B demonstrates that ligation of CEACAM1 with murine CEACAM1-N domain-Fc fusion protein induces increased TIM3 expression on SEB-responsive CD4$^+$Vβ8$^+$ T cells.

FIG. 8A shows an IP followed by immunoblot showing cis interaction as defined by immunoprecipitation for CEACAM1 or TIM3 and immunoblotting for alternative partner. FIG. 8B depicts that mutations of the IgV domain of TIM3 dramatically affect the binding affinity between CEACAM1 and TIM3. R112W represents a natural single nucleotide polymorphism (SNP) identified in the human population. FIG. 8C shows mutations of what is expected to be a critical disulfide bond between residues 58 and 110 of TIM3 based upon structural modeling, which indicates that these residues contribute to the structural stabilization for the cleft on IgV domain of TIM3, which is a critical feature for the binding affinity between CEACAM1 and TIM3. C58R is a natural SNP in the human population.

In FIG. 10A, WT, TIM3Tg/Ceacam1$^{-/-}$ or Ceacam1$^{-/-}$ mice received 100 µg mouse N-CEACAM1-Fc (or human IgG Fc as control as Fc for fusion protein is human) intraperitoneally by the schedule shown and at 10 days lymph nodes were isolated and stimulated in vitro with either anti-CD3 or staphylococcal enterotoxin (SEB). In FIG. 10B, in vitro responses of cells are shown for proliferation or interferon gamma production. Tolerance is demonstrated when TIM3 and CEACAM1 in trans are present. , P<0.01; *, P<0.001

FIG. 12 shows that CEACAM1 and TIM3 double positive cells accumulate amongst tumor infiltrating lymphocytes (TILs) associated with CT26 colorectal tumor cells and exhibit an exhausted phenotype with nearly undetectable levels of intracellular interferon-gamma, IL-2 and TNF. CT26 colorectal cancer cells were administered subcutaneously into WT Balb/c recipients and monitored for tumor growth. After 28 days, tumor infiltrating lymphocytes (TIL) were isolated and analyzed by flow cytometry for CEACAM1 and TIM3 or PD1 and TIM3 and the levels of intracellular interferon gamma, IL-2 or TNF assessed in each of the populations.

FIG. 13A shows the schedule for transfer of OTII-Rag2 ko T cells into WT or Ceacam1$^{-/-}$ recipients. FIG. 13B depicts, after gating on the lymphocytes, proliferation (CFSE) and CEACAM1 expression assessment on the Tg T cells. Increased proliferation and TIM3 expression were observed on transferred T cells when CEACAM1 was absent on antigen presenting cells. FIG. 13C shows a summary of results that demonstrate increased Tg T cell proliferation in all compartments examined when CEACAM1 was absent in the recipient mice, indicating the absence of a trans CEACAM1 signal provided by antigen-presenting cells which leads to decreased tolerance. *, P<0.05; , P<0.01; *, P<0.001

DETAILED DESCRIPTION

Figures 1A, 1B:
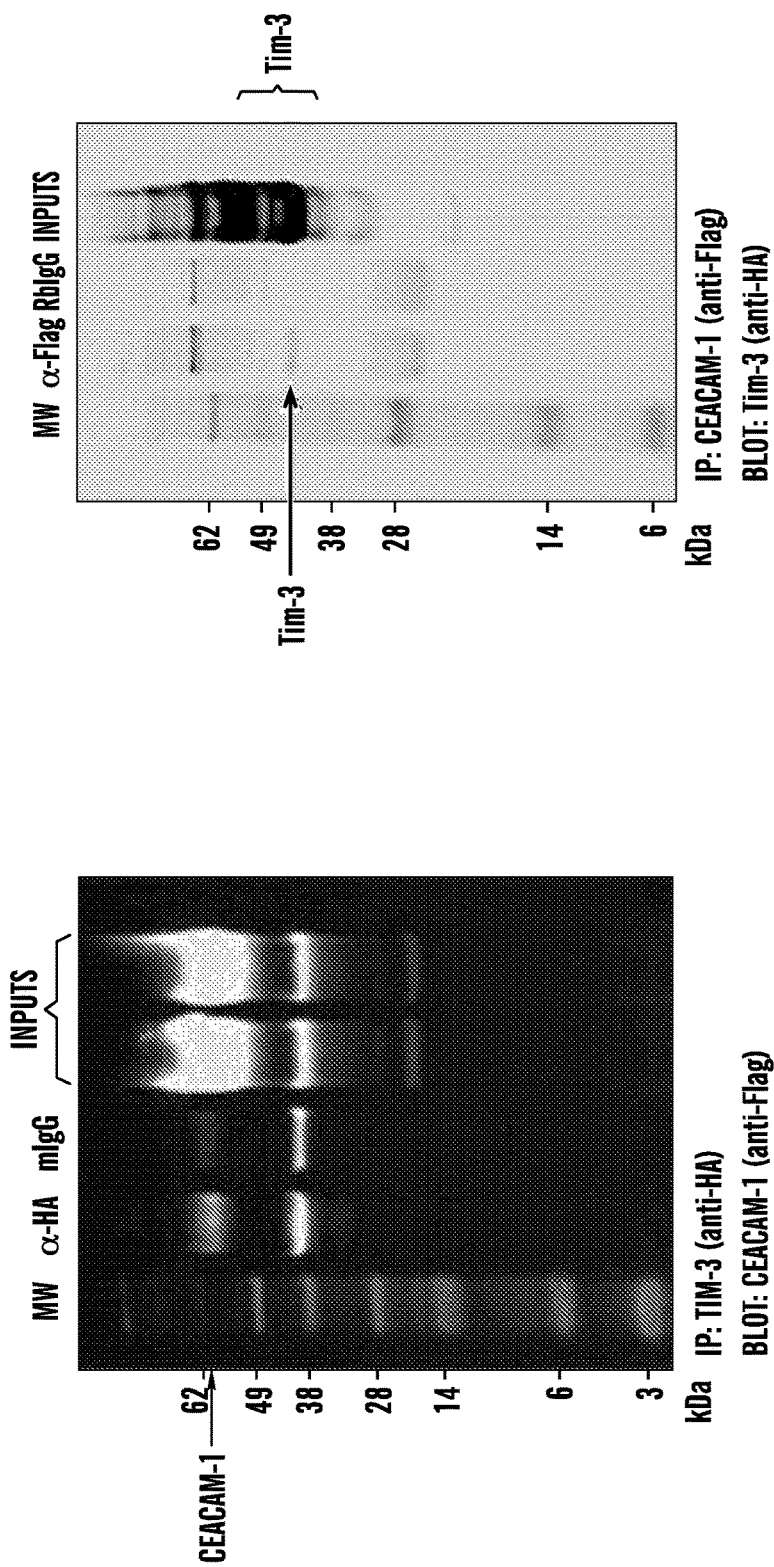
FIGS. 1A-1B demonstrate that CEACAM1 and TIM3 exhibit a biochemical interaction with each other. 293T-cells were transfected with human CEACAM1 and TIM3 expression plasmids. Whole cell lysates were prepared 48 hours after transfection for co-immunoprecipitation by anti-HA mAb TIM3 and western blot for CEACAM1 (anti-Flag) (FIG. 1A). Alternatively, whole cell lysates were prepared 48 hours after transfection for co-immunoprecipitation by anti-flag monoclonal antibody against CEACAM1 and western blot for TIM3 (anti-HA) (FIG. 1B).

T-cell tolerance functions, in part, to provide a population of immune system cells that recognize self-major histocompatability complex (MHC) molecules but do not recognize self-peptides. Previous studies have shown that both carcinoembryonic antigen related cell adhesion molecule 1 (CEACAM1) and Th1-specific cell surface molecule T-cell Immunoglobulin and Mucin domain-containing molecule-3 (TIM3) are important components of immune regulation. Both molecules have been observed previously to be expressed on activated T-cells, especially after prolonged activation.

More specifically, TIM3 is known to be involved in tolerance induction, and blockade of this molecule exacerbates experimental autoimmune encephalomyelitis (EAE) as well as disease in the non-obese diabetic (NOD) model of Type I diabetes. TIM3 is a receptor molecule selectively expressed on a subset of murine IFNγ-secreting Th1 cells, but not on Th2 cells, and regulates Th1 immunity and tolerance in vivo. In humans, TIM3 is expressed by a subset of activated CD4+ cells, and antiCD3/28 stimulation increases both the level of expression as well as the number of TIM3+ T-cells. TIM3 is expressed at high levels on in vitro polarized Th1 cells, IFNγ-secreting Th1 cells, and is also constitutively expressed on dendritic cells, on peripheral macrophages, and is expressed at lower levels on Th17 cells. In addition, human CD4+ T-cells secreted elevated levels of IFN-γ, IL-17, IL-2, and IL-6, but not IL-10, IL-4, or TNFα, when stimulated with anti-CD3/28 in the presence of TIM3-specific, antagonistic antibodies, which is mediated by induction of cytokines at the transcriptional level. TIM3 is a negative regulator of human T-cells and regulates Th1 and Th17 cytokine secretion; blockade of TIM3 with either monoclonal antibody or RNA interference agents increases the secretion of IFNγ by activated human T-cells (Hastings et al., 39 Eur. J. Immunol 2492 (2009)). TIM3 has also been shown to bind phosphatidylserine, a major "eat me" signal. TIM3 has been shown previously to utilize galectin-9 as a heterophilic ligand. Galectin-9 was identified as a TIM3 ligand that specifically recognizes carbohydrate motif(s) on the TIM3 IgV domain (Zhu et al., Nat. Immunol (2005); U.S. Patent Pub. No. 2005/0191721).

Structurally, TIM3 comprises an N-terminal IgV domain followed by a mucin domain, a transmembrane domain, and a cytoplasmic tail. The TIM3 IgV domain (of mice and men) has four noncanonical cysteines that form two unique disulfide bonds, which place the CC' and FG loops in close proximity. The surface formed by these loops form a binding cleft (FG-CC' cleft) that is not present in other immunoglobulin superfamily (IgSF) members, and mutagenesis studies demonstrated that this surface contributes to the recognition of a non-galectin-9-ligand(s) that is present on a wide range of primary immune cells (Cao et al., 26 Immunity 311 (2007); Anderson et al., 26 Immunity 273 (2007)). Within the FG-CC' cleft, Gln62 and Arg112 are critical for galactin-9-independent ligand binding. Substitution of Gln62 did not alter phagocytic activity, whereas substitution of Arg112 completely abrogated the activity. The metal-ion-dependent ligand binding site of TIM3, also important for recognition of apoptotic cells, requires N120 and D121, and to a lesser extent L118 and M119, present in the FG loop of the IgV domain. (Nakayama et al., 113 Blood 3821 (2009)). Thus, although a second heterophilic ligand had been predicted to be involved in TIM3 binding (i.e., to the FG-CC' cleft), the identity and nature of this interaction remained a mystery until the discoveries described herein.

In regard to CEACAM1 (also known as CD66 or biliary glycoprotein), clinical evidence shows that high-level CEACAM1 expression on tumors and tumor-infiltrating lymphocytes correlates with poor prognosis and high risk of metastasis. CEACAM1 functions as a regulatory co-receptor for both lymphoid and myeloid cell types, and is constitutively expressed in a wide range of tissues and cell types. Its expression on natural killer (NK) cells and T-cells is, however, mainly induced by cytokines and membrane-activating receptor activation. CEACAM1 consists of a single Ig variable domain-like amino terminus, from one to three Ig constant domain-like regions, and a single membrane-spanning segment followed by either a short (CEACAM1-S) or long (CEACAM1-L) cytoplasmic domain (Hinoda et al., 85 PNAS 6959 (1988)). The N-terminal domain has been shown to facilitate homophilic intercellular binding that influences a broad spectrum of cellular processes related to cellular activation and/or cell cycle progression; and is also targeted by the heterophilic adhesins of viral (murine hepatitis virus) and bacterial (*Neisseria gonorrhoeae* and *N. meningitidis*, *Moraxella catarrhalis*, and *Haemophilus influenzae*) pathogens, allowing their infection of the diverse array of CEACAM1-expressing human cells and tissues in vivo.

When expressed, CEACAM1 is characterized by significant alternate RNA splicing leading to eleven isoforms in humans and at least four isoforms in mice. These isoforms differ in the length of the cytoplasmic tail and the number of extracellular Ig-like domains and are named accordingly. As noted, the majority of CEACAM1 isoforms possess either a long (CEACAM1-L) CT or a short (CEACAM1-S) cytoplasmic tails (Azuz-Lieberman et al., 17 Intl. Immunol 837 (2005); Gray-Owen & Blumberg, 2006; Moller et al., 65 Int. J. Cancer 740 (1996); Nakajima et al., 168 J. Immunol 1028 (2002); Singer et al., 168 J. Immunol 5139 (2002)). The long cytoplasmic tail (~72 amino acids in humans) contains two immune-receptor tyrosine-based inhibitory motifs (ITIMs) (Chen et al., 172 J. Immunol 3535 (2004)). These isoforms are inhibitory for T-cell responses, which inhibition generally involves the ITIM domains and Src homology 2 domain phosphatase 1 (SHP-1). ITIM phosphorylation and, consequently, its association with SHP-1 requires p56 Lck kinase and the ability to bind homophilically. CEACAM1 recruits SHP-1 to the T-cell receptor (TCR) signalsome where SHP-1 blocks ZAP-70 activation via dephosphorylation of CD3-ξ, ZAP-70, or both. Indeed, masking the homophilic binding site with a specific Fab causes increased cytotoxicity and lymphocyte degranulation (Chen et al., 180 J. Immunol 6085 (2008)).

Figure 4:
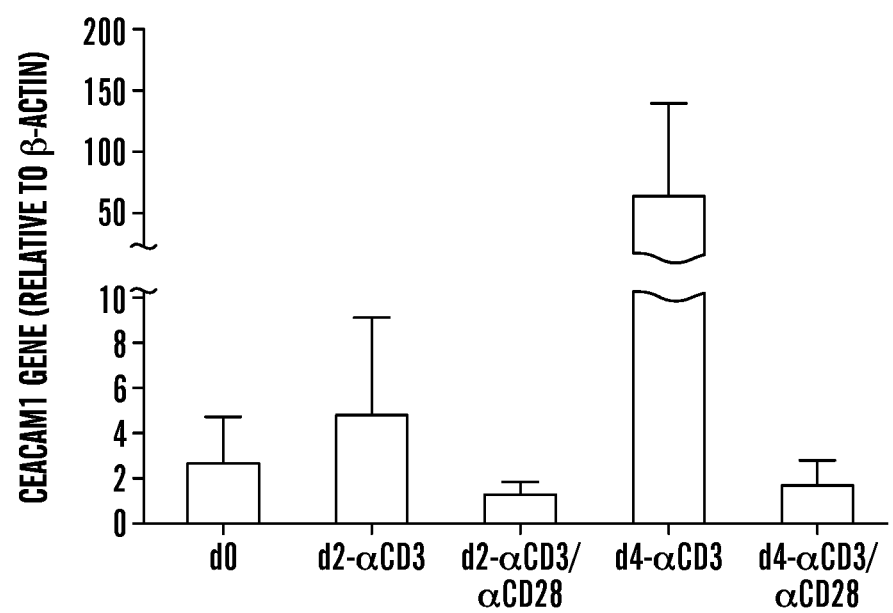
FIG. 4 depicts Pan T-cells stimulated with CD3, and CD3/CD28 for 0, 2 or 4 days. CEACAM1 expression was analyzed by quantitative PCR. CEACAM1 expression, which is low on resting T-cells, is transcriptionally regulated by ligation of T-cells through the TCR/CD3 complex (signal 1) but negatively regulated when the TCR/CD3 complex is co-engaged by the classical co-stimulatory signal (signal 2) provided by CD28.
Figure 5A:
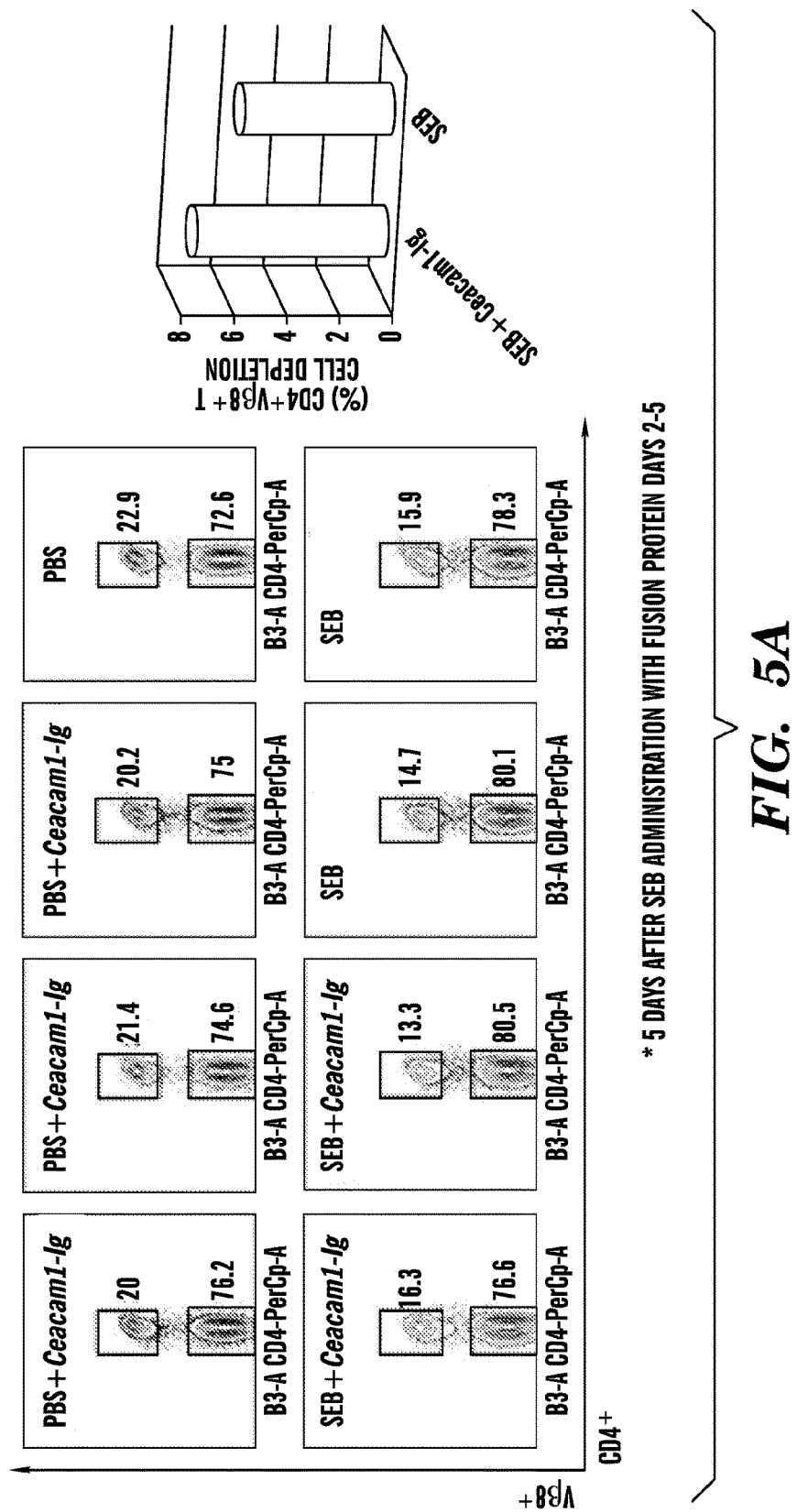
FIGS. 5A-5B confirm in vitro data demonstrating induction of TIM3 by homophilic ligation only in the SEB-responsive T cell subset.
Figure 5B:
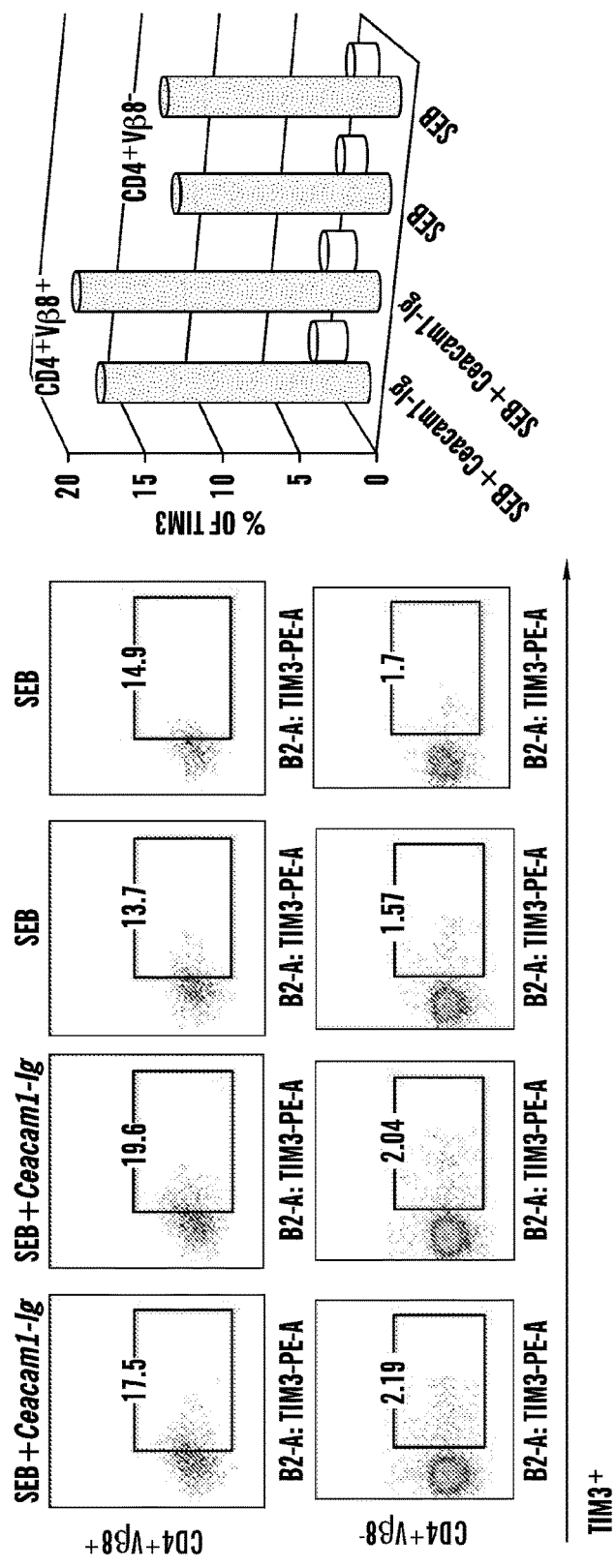

As described herein, previous studies have determined that CEACAM1 is a ligand for itself (homophilic ligation), and is involved in heterophilic ligation with galectin 3 and selectins. CEACAM1 expression, which is low on resting T-cells, is transcriptionally regulated by ligation of T-cells through the TCR/CD3 complex (signal 1) but negatively regulated when the TCR/CD3 complex is co-engaged by the classical co-stimulatory signal (signal 2) provided by CD28 (FIG. 4). Given the fact that TCR/CD3 ligation alone (in the absence of costimulation) is a common mechanism for the induction of T-cell tolerance, the strong induction of CEACAM1 by such stimulation may, without wishing to be bound or limited by theory, be part of the tolerogenic program.

Further, in regard to the tertiary structure of CEACAM1, the two major isoforms, CEACAM1-4L and CEACAM1-4S, which differ only in their cytoplasmic domains, have extracellular domains (ectodomains) comprised of four glycosylated Ig domains. CEACAM1-induced cell signaling is regulated by its intercellular homophilic binding at the cell surface, which is mediated by the N-terminal Ig domain (D1) in a reciprocal D1-D1 interaction. The basic structure of the IgV N-terminal domain of CEACAM1 is a tertiary fold of a stacked pair of β-pleated sheets. There are nine component β strands, with strands A, B, E, and D lying in one sheet and strands C, C', C", F, and G being antiparallel in the other sheet. The GFCC' face of the N-terminal domain of CEACAM1 is known to be crucial for mediating homophilic adhesion. Homophilic and heterophilic interactions have been observed for other adhesion receptor-ligand pairs; such as of CD2 with CD58; ICAM-1 with ICAM-1, LFA-1, rhinoviruses or *Plasmodium falciparum*—infected erythrocytes; or cadherins with cadherins (Watt et al., 98 Blood 1469 (2001)). These interactions indicated that the GFCC' faces of the immunoglobulin family members may have evolved, without wishing to be bound or limited by theory, as a sticky patch to recognize a variety of protein-protein interactions (Springer et al., 6 Ann. Rev. Cell Biol. 359 (1990)).

A peptide region responsible for CEACAM heterophilic interactions, for example with *Neisseria* Opa proteins, is also on the GFCC'C" face and overlaps partially with the homophilic binding site. Fedarovich et al., D62 Acta Cryst. 971 (2006). In comparison, binding of a murine CEACAM1 to murine coronavirus requires a uniquely folded CC' loop, in which amino acids 34 to 52 play a crucial role (Tan et al., 21 EMBO J. 2076 (2002); Watt et al., 2001). Additionally, amino acids between residues 27 to 42 (particularly D27L28F29) and S32, Y34, V39, Q44, Q89, and 191 on the GFCC'C" face form differential adhesioptopes for the binding of *H. influenzae*, and the *N. gonorhheae* and *N. meningiditis* Opa proteins. These adhesiotopes are likely a groove; formed by homophilic cis binding that involves V39 and D40 CC' loop residues, or formed after disruption of CEACAM1 cis dimerization by cytokine (e.g., TNFα) activation that precedes CEACAM1/pathogen binding (Watt et al., 2001).

Moreover, the IgC2 domain of CEACAM1 has also been implicated in coronavirus and *H. influenzae* receptor activity Immobilized CEACAM1, in which the tertiary structure of this highly flexible molecule is limited, also exhibits decreased adhesion, further implicating the cytoplasmic regions of the molecule (e.g., intracellular dimerization) in both homophilic and heterophilic interactions and signaling. Further, the formation of homodimers in cis has been characterized for multiple splice variants (isoforms), even those lacking IgC2 domains.

The lack of intradomain disulfide bridges in the N-terminal D1 domain renders the CEACAM1 ectodomain highly flexible. CEACAM1 exists in the cell membrane in microclusters; whereas homophilic binding triggers reorganization that results in two different kinds of dimers, as well as trimers and higher-order oligomers. Because of the hinge regions between the Ig domains, antiparallel trans-dimers (C-dimers) and parallel cis-dimers (A-dimers) can be formed. The N-terminal D1 domain participates in both C- and A-dimerization, while the D2-D4 domains are involved only in A-dimerization. Divalent cations decreased ectodomain flexibility and enhanced formation of multimeric complexes, which are further implicated in CEACAM1-mediated cell adhesion. Importantly, the dimerization of the ectodomains is transduced by the transmembrane domains to the cytoplasmic domains, thus, in turn, directing intracellular signaling. Another binding site might be implicated across the ABED face, depending on the level and flexibility of glycosylations on the CEACAM1 molecule (Klaile et al., 187 J. Cell Biol. 553 (2009)).

CEACAM1 function is also likely impacted by glycosylation. Carbohydrates account for up to sixty percent of the weight of CEACAM1 expressed on the cell surface. The role of this enormous carbohydrate content allows for the construction of "subspecies" of CEACAM1 isoforms. For example, the ability of CEACAM1 to express sialyl Lewis x modifications can affect leukocyte homing (Chen et al., 86 J. Leuk. Biol. 195 (2009)).

Discriminating between cis and trans interactions in both homophilic and heterophilic adhesions, whether expressed on the same or opposing cells are important, with cis interactions being able to inhibit or enhance interactions in trans. Homophilic interactions or dimerization in cis can thus maintain, create, or obliterate the receptor conformation for heterophilic binding or cell signaling. For example, homophilic interactions or dimerization of CEACAM1 molecules in cis can either maintain the receptor in a conformation incapable of interacting with opposing cells, or place the N-terminal GFCC'C" face in the correct orientation to increase the avidity of binding to homophilic or heterophilic counter-receptors on the same or opposing cells (as is the case with, for example, ICAM-1, the cadherins, and CEA). Engagement of CEACAM1 homophilically on the same epithelial cell can prevent its interaction in trans and can deliver a negative signal inhibiting epithelial cell proliferation, a regulatory mechanism that is lost when CEACAM1 levels are decreased during epithelial tumor formation. Alternatively, the activation of CEACAM1 molecules on the surface of neutrophils during inflammation can control the presentation of sLex residues to E-selectin ligands on endothelial cells and regulate CD11/CD18 and L-selectin levels. On endothelial and epithelial cells, CEACAM1 activation, perhaps by inducing or inhibiting homophilic interactions or dimerization, can also regulate isoform concentrations on the cell surface, orient the molecules, or increase the avidity of adjacent residues on the GFCC'C" face of CEACAM1 for Neisserial Opa proteins or *H. influenzae*. Before the discoveries described herein, however, it was not clear which mechanisms are involved in homophilic versus heterophilic interactions of the N-terminal domain interaction of CEACAM1 in relation to T-cell tolerance.

Figure 2A:
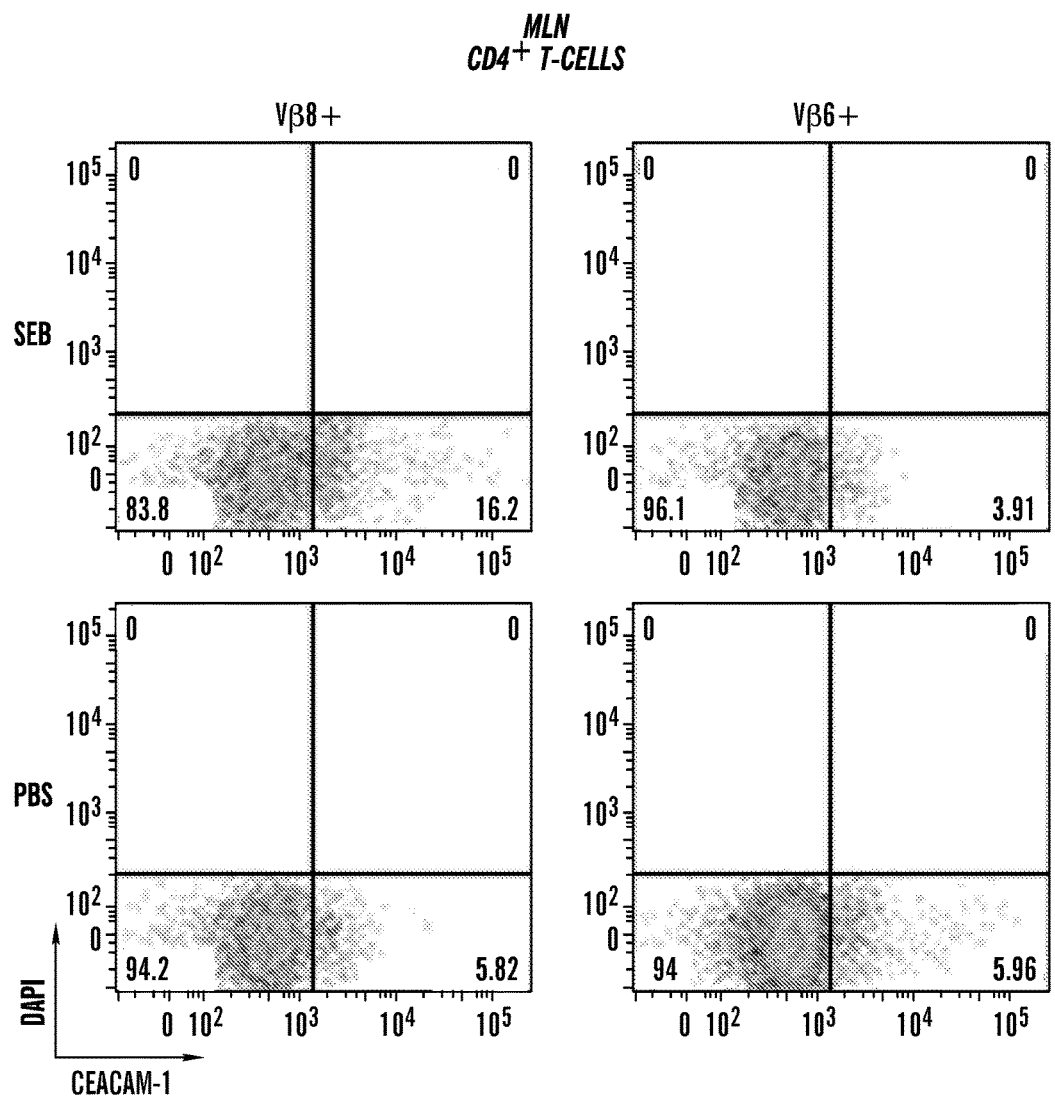
FIG. 2A presents data from FACS analysis showing maximal CEACAM1 expression on the proportion of SEB-reactive T-cells during 8-days of SEB-administration. Mice were injected intraperitoneally with 100 µg/100 µl SEB, or 100 µl of PBS as control. After 8 days (before the crash of Vβ8 T-cells), the expression of CEACAM1 on Vβ8 T-cells (SEB-reactive), and on Vβ6 T-cell (SEB non-reactive) from mice in both of these groups was analyzed.
Figure 15:
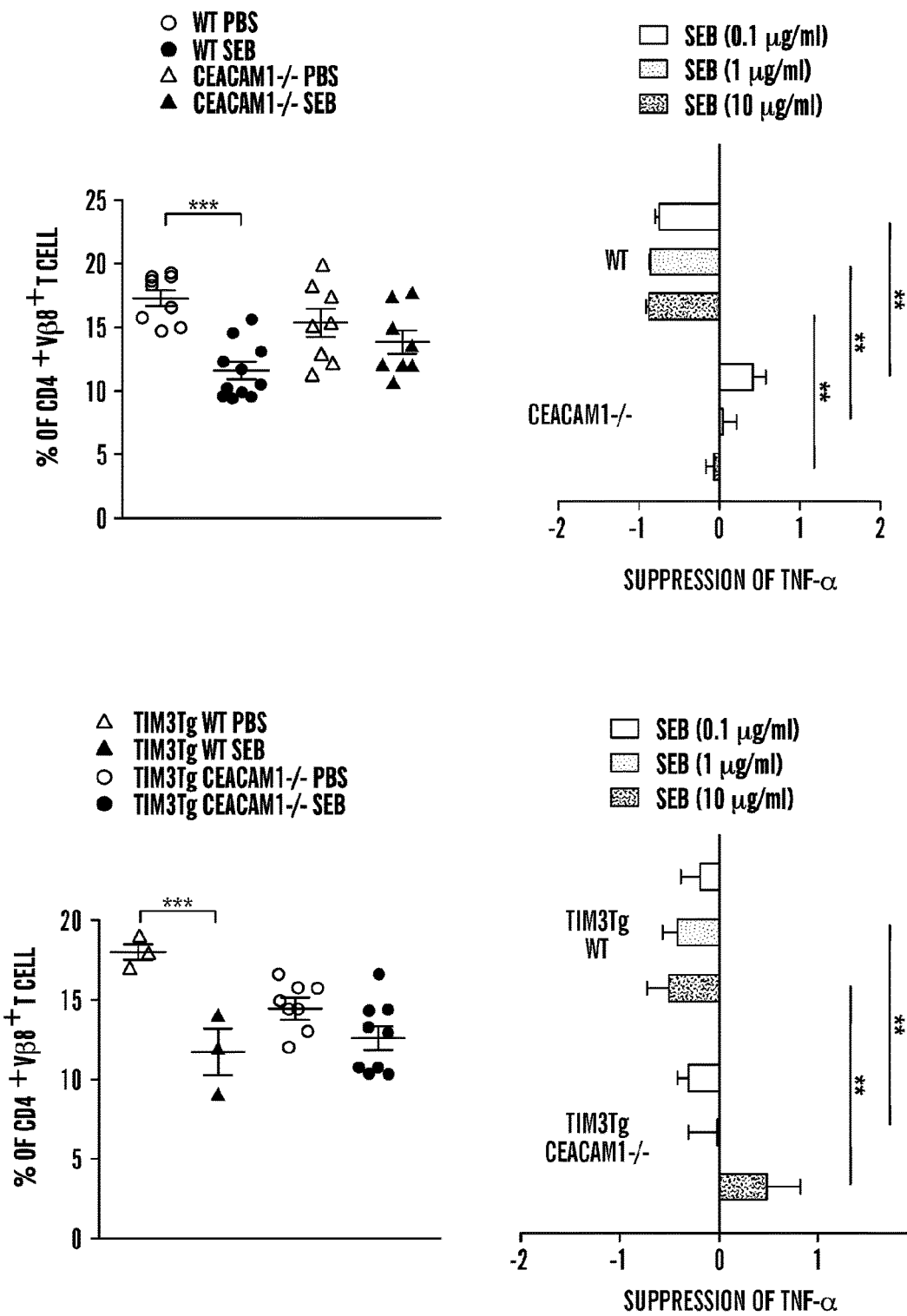
FIG. 15 demonstrates that Staphylococcal enterotoxin (SEB) induced tolerance (both deletional and non-deletional) is abrogated in either CEACAM1-deficient mice or CEACAM1-deficient mice with forced transgenic expression of TIM3 on T cells demonstrating that TIM3 requires CEACAM1 for its function as a tolerance inducing molecule. SEB induced tolerance was generated by standard methods in WT, Ceacam1$^{-/-}$, Ceacam1$^{-/-}$-TIM3Tg or TIM3Tg-WT mice and T cells expressing T cell receptor Vβ8 analyzed for deletion or responses to SEB evaluated on splenocytes from SEB treated mice as defined by TNF expression. Whereas WT and TIM3Tg-WT mice exhibited deletional (decreased) Vβ8 T cells and non-deletional tolerance (decreased TNF secretion in response to SEB), these were absent in CEACAM1-deficient mice. , P<0.01; *, P<0.001
Figure 16:
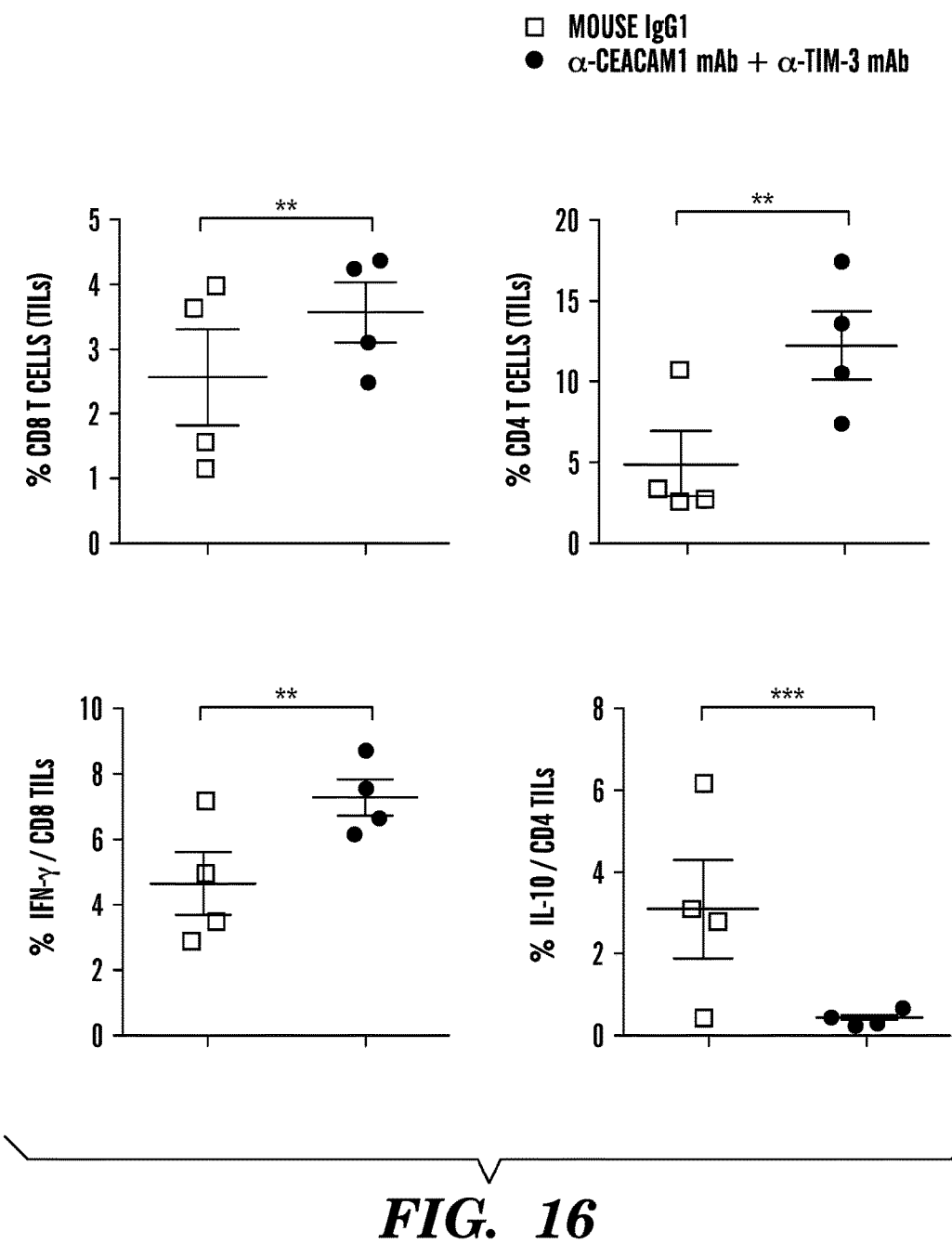
FIG. 16 demonstrates that co-blockade of CEACAM1 and TIM3 synergistically enable anti-tumor immune responses. Co-blockade of TIM3 and CEACAM1 enhances anti-colorectal tumor responses as defined by decreased growth of CT26 tumors, as depicted at FIG. 6, and increased anti-tumor immune responses as shown here as defined by increased CD8$^+$ and CD4$^+$ T cells, CD8$^+$ T cells secreting interferon gamma and decreased CD4$^+$ T cells secreting IL10 among tumor infiltrating lymphocytes (TILs). CT26 colorectal tumor cells were inoculated subcutaneously into WT Balb/c mice and monitored for tumor growth after treatment with either MOPC (IgG1 control) or a combination of antibodies specific for CEACAM1 and TIM3. After 26 days, tumor infiltrating lymphocytes (TIL) were isolated and analyzed for the relative proportion of CD4$^+$ and CD8$^+$ T cells, the proportion of CD8$^+$ T cells that expressed intracellular interferon gamma and the proportion of CD4$^+$ T cells that expressed intracellular IL-10 as defined by flow cytometry. *, P<0.05; , P<0.01; *, P<0.001
Figure 17A:
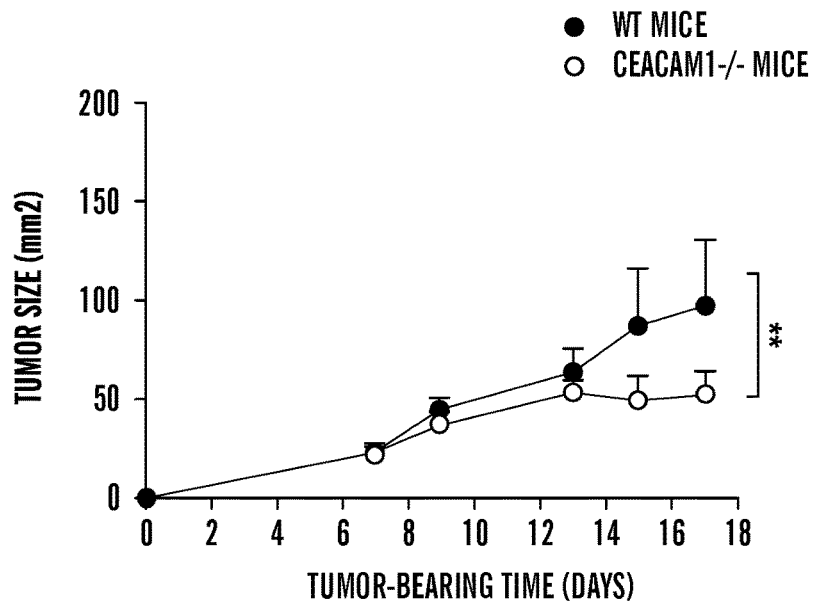
FIGS. 17A-17C demonstrate that genetic deletion of CEACAM1 leads to increased anti-tumor responses against a colorectal cancer (CT26) as shown by decreased tumor growth after subcutaneous inoculation relative to WT mice (FIG. 17A), increased CD8$^+$AH1-tetramer$^+$ T cells in draining lymph nodes that are directed against and specific for the CT26 tumor cells (FIG. 17B) and decreased TIM3$^+$CD8$^+$ T cells among TILs (FIG. 17C). CT26 colorectal tumor cells were inoculated subcutaneously into WT Balb/c or Ceacam1$^{-/-}$ mice on a BALB/c background and tumor growth monitored. After 26 days, TILs were isolated and examined for TIM3 expression or lymphocytes isolated from draining lymph nodes and analyzed for staining with AH1-tetramer on CD8$^+$ T cells. The AH1 tetramer detects a MHC class I restricted antigen which is expressed by CT26 tumor cells and recognized by cytolytic CD8+$^+$ T cells. , P<0.01; *, P<0.001
Figure 17B:
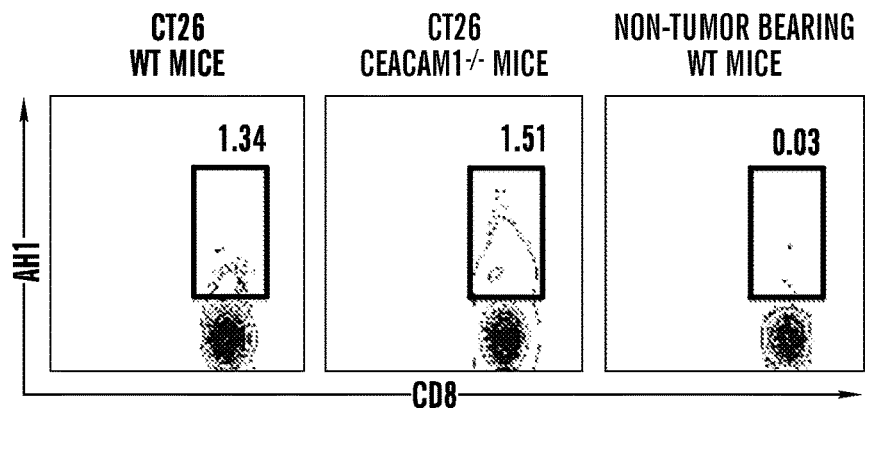
Figure 17C:
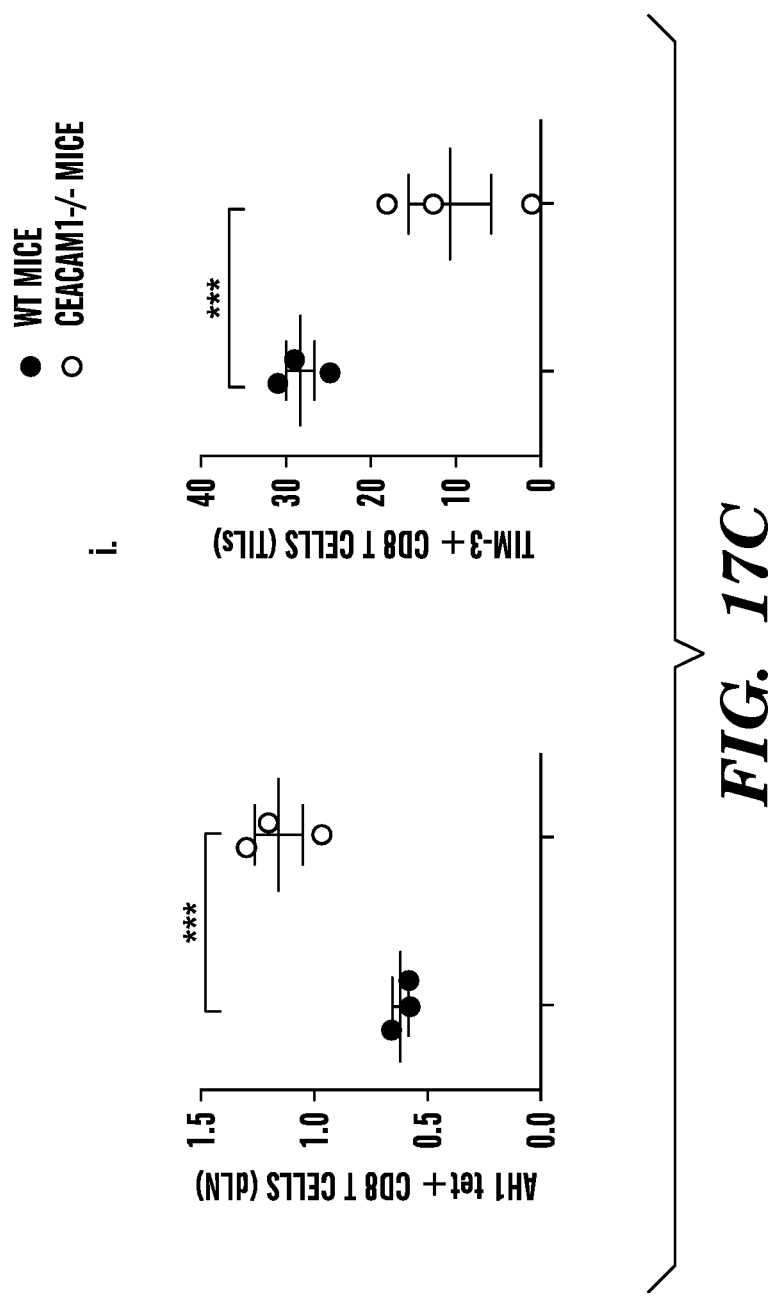

Thus, while both CEACAM1 and TIM3 have been shown to play indispensible roles to fulfill immune regulation, the interaction between these two molecules had not been identified or characterized before the discoveries described herein. Biochemical co-immunoprecipitation analysis on these two molecules, as shown herein, reveals that CEACAM1 exhibits a biochemical interaction with TIM3 (FIGS. 1A-1B and 8A-8C). Further, the mechanisms responsible for the activity of CEACAM1 and TIM3 interaction were examined in T-cell tolerance models following administration of staphylococcal enterotoxin B (SEB), an in vivo stimulus of the TCR/CD3 complex. SEB belongs to a class of molecules known as bacterial "superantigens," which are potent activators of T-cells, especially for those expressing T-cell receptor Vβ chains, and induce the production of cytokines such as IFN-γ, TNFα, IL-1, IL-2, IL-6, IL-12, etc. As demonstrated herein, SEB administration revealed an up-regulation of CEACAM1 in the context of tolerance induction in vivo (FIG. 2A, FIG. 15).

The ability of a chimeric fusion protein to target the N-domain binding domain of CEACAM1 (and thus control activation of tolerance), was also examined, given its importance in inhibiting excessive inflammation in irritable bowel disease, multiple sclerosis, and rheumatoid arthritis. CEACAM1 ligation with a CEACAM1-Fc fusion protein on SEB-responsive T-cells was followed by in vitro re-stimulation with SEB (FIG. 2B): only with homophilic trans binding do these cells up-regulate TIM3 (29% Mean Fluorescence) in response to SEB re-stimulation, indicating a naturally occurring tolerance mechanism. Similar results were also observed in vivo (FIGS. 5A and 5B, FIGS. 10A, 10B, and 11).

Thus, there are several aspects to the CEACAM1/TIM3 interaction that are provided by the compositions and methods described herein as avenues for modulating T-cell tolerance: CEACAM1 interacts with TIM3 via heterophilic trans binding; CEACAM1 and TIM3 interact in cis, in the same cell; CEACAM1 homophilic binding in trans leads to up-regulation of TIM3; in the absence of CEACAM1, TIM3 is not expressed Inhibiting any of these interactions provides approaches, in some aspects, for limiting the development of T-cell tolerance. Enhancing any of these interactions, in some aspects, can be harnessed to enhance the development of T-cell tolerance.

Accordingly, in some aspects, the compositions and methods described herein modulate T-cell tolerance by inhibiting the biological interaction of TIM3 and CEACAM1, thus abrogating T-cell tolerance. Relieving the suppression of the immune system is highly desirable in, for example, an immunocompromised subject or a subject suffering from cancer, which can comprise, in some embodiments of the aspects described herein, inhibiting T-cell tolerance by inhibiting TIM3/CEACAM1 interaction; inhibiting CEACAM1 homophilic binding so that TIM3 expression is not up-regulated; targeting cells in which TIM3 and CEACAM1 have associated in cis, by, for example, targeting the interaction between CEACAM1 and the C-C' loop of TIM3; and/or a combination thereof.

In some aspects, the compositions and methods described herein modulate T-cell tolerance by enhancing the biological interaction of TIM3 and CEACAM1. Such approaches provide for methods of treating an autoimmune disease or other disorders in which it is desirable that T cell tolerance is increased in a subject by enhancing T-cell tolerance comprising stimulating the TIM3/CEACAM1 interaction.

In some embodiments of these compositions and methods, a TIM3 molecule is provided as a ligand for CEACAM1. As used herein, the term TIM3 refers to the polypeptide of SEQ ID NOs: 1 or 2, together with any naturally occurring allelic, splice variants, and processed forms thereof. Typically, TIM-3 refers to human TIM-3. The term "TIM-3" is also used in notation to refer to particular truncated forms or fragments of the TIM-3 polypeptide. Reference to any such forms or fragments of TIM-3 can be identified in the application, e.g., by "TIM-3 (24-131)." Specific residues of TIM-3 can be referred to as, for example, "TIM-3(62)." For example, the IgV region of TIM3, which comprises amino acids 24-131 of SEQ ID NO: 1, can be referred to as TIM3 (24-131). Exemplary single nucleotide polymorphisms found in the human population include, for example, TIM3(R112W) and TIM3(C58R).

In some embodiments, the TIM3 molecule is a soluble TIM3 or peptide variant thereof "Soluble TIM3," as used herein, refers to any form of TIM3, including functional variants of TIM3, that is dissociated from the cell membrane. Soluble TIM3 can be, for example, in some embodiments, a C-terminal truncated form of full-length TIM3 or a transmembrane-deleted version of TIM3. In some embodiments, the soluble TIM3 molecule comprises a single domain of the extracellular region of TIM3, i.e., the IgV domain or the mucin domain or the C-C' loop. In some embodiments, the soluble TIM3 is an alternatively spliced variant of full-length TIM3, which includes the IgV domain and intracellular region, but not the mucin domain or transmembrane region. In some embodiments, the soluble TIM3 molecule includes an extracellular region of TIM3.

In addition to TIM3 itself, the CEACAM1-binding molecule can be a mimic of TIM3, such as a small molecule, a polypeptide (e.g., a peptido-mimetic), an antibody or a portion of an antibody, a polynucleotide, a polysaccharide, a lipid, a drug, or a functional variant or derivative thereof, or a combination of any of these that acts to mimic or recapitulate the effects of TIM3 binding to CEACAM1, for example. The CEACAM1-binding TIM3 mimic can be found in nature or it can be derived or synthesized using suitable in vitro and synthetic methods known by those of skill in the art. For example, in some embodiments, the TIM3 mimic CEACAM1-binding molecule can be a small molecule that is identified through screening a library of small molecules for the ability to compete with TIM3 binding to CEACAM1. As another example, in some embodiments, the TIM3-derived CEACAM1-binding molecule can be generated and identified using phage display of peptides. The TIM3 mimic can be designed, in different embodiments, to act as either an antagonist or agonist of the natural CEACAM1-TIM3 interaction. For example, in some embodiments of the aspects described herein, a TIM3 peptide that can bind CEACAM1 for use in the compositions and methods described herein comprises TIM-3 (58-77) or Cys-Pro-Val-Phe-Glu-Cys-Gly-Asn-Val-Val-Leu-Arg-Thr-Asp-Glu-Arg-Asp-Val-Asn-Tyr (SEQ ID NO: 30). For example, in some embodiments of the aspects described herein, a TIM3 peptido-mimetic that can bind CEACAM1 for use in the compositions and methods described herein comprises amino acids 58-62 and 112-119 of TIM-3 linked by a SGSG linker or Cys-Pro-Val-Phe-Glu-Ser-Gly-Ser-Gly-Arg-Ile-Gln-Glu-Pro-Gly-Ile-Met (SEQ ID NO: 31).

In certain aspects and embodiments, provided herein are isolated and/or purified forms of TIM-3 polypeptides and fragments thereof, which are isolated from, or are otherwise substantially free of, other proteins which might normally be associated with the protein or a particular complex including the protein.

Accordingly, in some embodiments of the compositions and methods described herein, a TIM-3 polypeptide is a polypeptide having an amino acid sequence that is at least 90%, at least 95%, at least 97%, at least 99% or 100% identical to SEQ ID NO: 1 or SEQ ID NO: 2, and which retains one or more signaling activities of the TIM3 polypeptide of SEQ ID NO: 1 or SEQ ID NO: 2. The term "TIM3 polypeptide," as used herein, also encompasses a portion or fragment of such a TIM3 polypeptide that retains one or more signaling activities of the polypeptide of SEQ ID NO: 1 or SEQ ID NO: 2, as well as conservative substitution variants of a TIM-3 polypeptide that retain one or more signaling activities of the polypeptide of SEQ ID NO: 1. At a minimum, a TIM3 polypeptide as described herein can mediate the activation of CEACAM1 and/or can specifically bind to or interact with CEACAM1. In some embodiments of the methods and compositions described herein, the portion of the TIM3 polypeptide comprises the IgV domain of TIM3. In some embodiments of the compositions and methods described herein, the soluble TIM3 polypeptides contain one or more conservative amino acid substitutions relative to SEQ ID NO: 1 or SEQ ID NO: 2. The amino acid identity between two polypeptides can be determined, for example, by first aligning the two polypeptide sequences using an alignment algorithm, such as one based on the PAM250 matrix or by other methods well-known in the art.

In some embodiments of the compositions and methods described herein, peptides are provided having CEACAM1-binding activity that mimic that of TIM3, referred to herein as a "TIM3 mimic," "TIM3 peptido-mimetic," or "TIM3-derived CEACAM1-binding peptide,"—that is, in other words, a peptide comprising a functional portion of TIM3 that acts as a CEACAM1 ligand. In some particular embodiments, the TIM3 peptide comprises the FG-CC' cleft of TIM3. Thus, in some embodiments of the compositions and methods described herein, the agent that increases CEACAM1 activity is a peptide mimetic or a small molecule that can functionally replace TIM3 in activating the CEACAM1 receptor. The peptide or small molecule can structurally resemble the surface of TIM3 that binds CEACAM1, such that the peptide or small molecule can activate CEACAM1 upon binding it, leading to increased CEACAM1 activity. For example, in some embodiments of the aspects described herein, a TIM3 peptide that can bind CEACAM1 for use in the compositions and methods described herein comprises SEQ ID NO: 30 or SEQ ID NO: 31.

The amino acid sequences of exemplary TIM3 polypeptides have been deposited at the GenBank database under accession numbers AAL65156-AAL65158, as follows:

```
GenBank Accession No. AAL65157, human TIM3, clone 1
                                              (SEQ ID NO: 1)
MFSHLPFDCV LLLLLLLLTR SSEVEYRAEV GQNAYLPCFY TPAAPGNLVP VCWGKGACPV
60

FECGNVVLRT DERDVNYWTS RYWLNGDFRK GDVSLTIENV TLADSGIYCC RIQIPGIMND
120

EKFNLKLVIK PAKVTPAPTL QRDFTAAFPR MLTTRGHGPA ETQTLGSLPD INLTQISTLA
180

NELRDSRLAN DLRDSGATIR IGIYIGAGIC AGLALALIFG ALIFKWYSHS KEKIQNLSLI
240

SLANLPPSGL ANAVAEGIRS EENIYTIEEN VYEVEEPNEY YCYVSSRQQP SQPLGCRFAM
300

P
301

GenBank Accession No. AAL65158, human TIM3, clone 2
                                              (SEQ ID NO: 2)
MFSHLPFDCV LLLLLLLLTR SSEVEYRAEV GQNAYLPCFY TPAAPGNLVP VCWGKGACPV
60

FECGNVVLRT DERDVNYWTS RYWLNGDFRK GDVSLTIENV TLADSGIYCC RIQIPGIMND
120

EKFNLKLVIK PAKVTPAPTR QRDFTAAFPR MLTTRGHGPA ETQTLGSLPD INLTQISTLA
180

NELRDSRLAN DLRDSGATIR IGIYIGAGIC AGLALALIFG ALIFKWYSHS KEKIQNLSLI
240

SLANLPPSGL ANAVAEGIRS EENIYTIEEN VYEVEEPNEY YCYVSSRQQP SQPLGCRFAM
300

P
301
```

```
-continued
An example of a truncated, soluble TIM3 peptide having the
amino acid sequence (SEQ ID NO: 3):
MFSGLTLNCV LLLLQLLLAR SLEDGYKVEV GKNAYLPCSY TLPTSGTLVP MCWGKGFCPW
60

SQCTNELLRT DERNVTYQKS SRYQLKGDLN KGDVSLIIKN VTLDDHGTYC CRIQFPGLMN
120

DKKLELKLDI KAGYSCKKKK LSSLSLITLA NLPPGGLANA GAVRIRSEEN IYTIEENVYE
180

VENSNEYYCY VNSQQPS
197

GenBank Accession No. AAL65156, murine TIM3
                                                          (SEQ ID NO: 4)
MFSGLTLNCV LLLLQLLLAR SLEDGYKVEV GKNAYLPCSY TLPTSGTLVP MCWGKGFCPW
60

SQCTNELLRT DERNVTYQKS SRYQLKGDLN KGDVSLIIKN VTLDDHGTYC CRIQFPGLMN
120

DKKLELKLDI KAAKVTPAQT AHGDSTTASP RTLTTERNGS ETQTLVTLHN NNGTKISTWA
180

DEIKDSGETI RTAIHIGVGV SAGLTLALII GVLILKWYSC KKKKLSSLSL ITLANLPPGG
240

LANAGAVRIR SEENIYTIEE NVYEVENSNE YYCYVNSQQP S
281
```

TIM3 peptides and portions thereof for use with the compositions and methods described herein can be made according to methods disclosed elsewhere. See, e.g., PCT US2007/024067, filed 15 Nov. 2007, entitled Therapeutic Uses of TIM3 Modulators; Monney et. al., 415 Nature 536 (2002); Anderson et. al., 318 Science 1141 (2007); U.S. Patent Pubs. No. 2004/0005322; No. 2005/0191721. Alternatively, TIM3 peptides and portions thereof for use with the compositions and methods described herein can be cloned and expressed according to molecular methods known to one skilled in the art. In some embodiments, the gene encoding TIM3, or a portion thereof, can be cloned into an expression vector for the overexpression of the respective protein.

In other embodiments of the compositions and methods described herein for increasing TIM3 and CEACAM1 activity and enhances T cell tolerance, the agent that increases TIM3 activity is a peptide mimetic or a small molecule which can functionally replace CEACAM1 in activating the TIM3 receptor. In some embodiments, the peptide or small molecule can, for example, structurally resemble the surface of CEACAM1 that binds TIM3, such that the peptide or small molecule can activate TIM3 upon binding it, leading to increased TIM3 activity. In some specific embodiments, the agent that increases TIM3 activity promotes the tyrosine phosphorylation of the intracellular domain of TIM3.

Functional variants of TIM3 useful with the compositions and methods described herein include molecules representing mutations, additions, deletions, and truncations of full-length TIM3, provided such molecules retain the ability to bind to CEACAM1. Alternatively, an agent that inhibits TIM3-stimulated CEACAM1 activity and/or CEACAM1-stimulated TIM3 activity can, in some embodiments of the compositions and methods described herein, include soluble TIM3 proteins or conjugates, or protein or antibody, small interfering RNA specific for or targeted to TIM3 mRNA, and antisense RNA that hybridizes with the mRNA of TIM3, for example.

As used herein, an "agent" can refer to a protein-binding agent that permits modulation of CEACAM1/TIM3 interactions. Such agents include, but are not limited to, antibodies ("antibodies" includes antigen-binding portions of antibodies such as epitope- or antigen-binding peptides, paratopes, functional CDRs; recombinant antibodies; chimeric antibodies; tribodies; midibodies; or antigen-binding derivatives, analogs, variants, portions, or fragments thereof), protein-binding agents, small molecules, recombinant protein, peptides, aptamers, avimers and protein-binding derivatives, portions or fragments thereof.

Antisense oligonucleotides represent another class of agents that are useful in the compositions and methods described herein, particularly as TIM3 or CEACAM1 antagonists. This class of agents and methods for preparing and using them are all well-known in the art, as are ribozyme and miRNA molecules. See, e.g., PCT US2007/024067 for a thorough discussion.

In some embodiments, the agent that modulates the TIM3/CEACAM1 interaction or pathway can be the coding nucleic acid for full-length TIM3 or CEACAM1, and is carried in a vector for transport and protein expression in living mammalian cells, for example, an adeno-associated virus. Upon transfection into a cell, the agent permits overexpression of TIM3 or CEACAM1 in vivo. Cloning and over expression of the full-length TIM3 and CEACAM1 can be performed as disclosed in, for example, U.S. Patent Pubs. No. 2004/0005322 and No. 2005/0191721.

Other agents for use in the compositions and methods described herein that inhibit TIM3 interaction with CEACAM1 include, for example, antibodies against TIM3, specifically reactive or specifically binding to the extracellular region of TIM3. Non-limiting examples include antibodies from the hydridomas 7D11, 10G12, and 11G8 (all mouse IgG1) for human TIM-3; monoclonal anti-human TIM-3, Clone #: 344823, isotype rat IgG2A, from R&D SYSTEMS; anti-human TIM3 antibodies from GALPHARMA; and antibodies from the hydridomas 8B.2C12 and 25F.1 D6, rat IgG2a, κ (Nakayama et al., 113 Blood 3821 (2000).

The term "antibody" as used herein, whether in reference to an anti-TIM3 or anti-CEACAM1 antibody, refers to a full length antibody or immunoglobulin, IgG, IgM, IgA, IgD or IgE molecules, or a protein portion thereof that comprises only a portion of an intact antibody, generally including an antigen binding site of the intact antibody and thus retaining the ability to bind a target, such as an epitope or antigen. Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al., 8 Protein Eng. 1057 (1995); and U.S. Pat. No. 5,641,870).

The term "specificity" refers to the number of different types of antigens or antigenic determinants to which a particular antibody or antigen-binding portion thereof can bind. The specificity of an antibody or antigen-binding portion thereof, alone or in the context of a bispecific or multispecific polypeptide agent, can be determined based on affinity and/or avidity. The affinity, represented by the equilibrium constant for the dissociation ($K_D$) of an antigen with an antigen-binding protein (such as a bispecific or multispecific polypeptide agent), is a measure for the binding strength between an antigenic determinant and an antigen-binding site on the antigen-binding protein: the lesser the value of the $K_D$, the stronger the binding strength between an antigenic determinant and the antigen-binding molecule. Alternatively, the affinity can also be expressed as the affinity constant ($K_A$), which is $1/K_D$. As will be clear to the skilled person, affinity can be determined in a manner known per se, depending on the specific antigen of interest. Accordingly, a bispecific or multispecific polypeptide agent as defined herein is said to be "specific for" a first target or antigen compared to a another target or antigen when it binds to the first antigen with an affinity (as described above, and suitably expressed, for example as a $K_H$ value) that is at least 10×, such as at least 100×, and preferably at least 1000×, and up to 10000× or more better than the affinity with which said amino acid sequence or polypeptide binds to the other target or polypeptide. For example, when a bispecific or multispecific polypeptide agent is "specific for" a target or antigen compared to another target or antigen, it is directed against said target or antigen, but not directed against such other target or antigen.

Avidity is the measure of the strength of binding between an antigen-binding molecule (such as a bispecific polypeptide agent described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as a bispecific polypeptide agent described herein) will bind to their cognate or specific antigen with a dissociation constant ($K_D$) of $10^{-5}$ to $10^{-12}$ moles/liter or less, such as $10^{-7}$ to $10^{-12}$ moles/liter or less or $10^{-8}$ to $10^{-12}$ moles/liter (i.e., with an association constant ($K_A$) of $10^5$ to $10^{12}$ liter/moles or more, and such as $10^7$ to $10^{12}$ liter/moles or $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. A binding site on a bispecific or multispecific polypeptide agent described herein may bind to the desired antigen with an affinity less than 500 nM, less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of a polypeptide domain described herein to bind to a target, such as a molecule present on the cell-surface, with a $K_D$ of $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$M or less. For example, if a polypeptide agent described herein binds to TIM3 with a $K_D$ of $10^{-5}$ M or lower, but not to another TIM molecule, such as TIM1 or TIM4, or a related homologue, then the agent is said to specifically bind TIM3. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

Similarly, antibodies or epitope-binding proteins that specifically target CEACAM1 can be used, in some embodiments of the compositions and methods described herein, to inhibit CEACAM1 binding to TIM3. For example, in some embodiments, humanized or composite human anti-CEACAM1 antibodies or portions thereof can be used in the compositions and methods described herein. Such antibodies are described, e.g., in U.S. Patent App. No. 61/565,640, entitled Anti-CEACAM1 Recombinant Antibodies for Cancer Therapy, filed 1 Dec. 2011, and in WO 2013/82366 published Jun. 6, 2013, and the references discussed therein. For example, in some embodiments of the compositions and methods described herein, a particular isolated recombinant antibody or antigen-binding portion thereof that binds specifically to CEACAM1 can comprise a heavy chain complementarity determining region (CDR) 1 consisting of the amino acid residues SSHGMS (SEQ ID NO: 5), a heavy chain CDR2 consisting of the amino acid residues TISSGGTYTYYPDSVKG (SEQ ID NO: 6), a heavy chain CDR3 consisting of the amino acid residues HDFDYDAAWFAY (SEQ ID NO: 7), a light chain CDR1 consisting of the amino acid residues SANSSVSYMY (SEQ ID NO: 8), a light chain CDR2 consisting of the amino acid residues LTSNLAS (SEQ ID NO: 9), and a light chain CDR3 consisting of the amino acid residues QQWSSNPPT (SEQ ID NO: 10).

Alternatively, in some embodiments of the compositions and methods described herein, the CEACAM1-binding antibody or epitope-binding peptide can be constructed to have CDR regions selected from the following: a heavy chain CDR 1 consisting of the amino acid residues SSHGMS (SEQ ID NO:5), SFYGMS (SEQ ID NO: 11), or SDYYLY (SEQ ID NO:12); a heavy chain CDR2 consisting of the amino acid residues TISSGGTYTYYPDSVKG (SEQ ID NO:6), TFSGGGNYTYYPDSVKG (SEQ ID NO:13) or TISVGGGNTSYPDSVKG (SEQ ID NO: 14); a heavy chain CDR3 consisting of the amino acid residues HDFDYDAAWFAY (SEQ ID NO: 7), or HGGLPFYAMDY (SEQ ID NO: 15), or GLTTGPAWFAY (SEQ ID NO: 16); a light chain CDR1 consisting of the amino acid residues SANSSVSYMY (SEQ ID NO: 8), SVSSSISSSNLH (SEQ ID NO: 17), KSSQSLLNSSNQKNYLA (SEQ ID NO: 18), or RASQKISGYLS (SEQ ID NO: 19); a light chain CDR2 consisting of the amino acid residues LTSNLAS (SEQ ID NO: 9), SVSSSISSSNLH (SEQ ID NO: 20), FASTRES (SEQ ID NO: 21), or AASTLDS (SEQ ID NO: 22); and a light chain CDR3 consisting of the amino acid residues QQWSSNPPT (SEQ ID NO: 10), QQWSSHPFT (SEQ ID NO: 23), QQHYSTPWT (SEQ ID NO: 24) or LQYASSLMYT (SEQ ID NO: 25). See also U.S. Patent Pub. No. 2004/0047858, for example.

Other anti-CEACAM1 monoclonal antibodies useful in the compositions and methods described herein include AgB10, that inhibits CEACAM1-mediated EAE suppression in mice (Fujita et al., 175 Am. J. Pathol. 1116 (2009)); a CEACAM1 antibody (Chen et al., 2004); murine D14HD11 (Yu et al., 281 J. biol. Chem. 39179 (2006)); murine CEACAM1-specific CC1 (Iijima et al., 199 J. Exp. Med. 471 (2004)); mouse anti-human CEACAM1 MRG-1 (Ortenberg 2012); mouse anti-human CEACAM1 N-domain specific antibodies 5F4, 34B1, and 26H7 (IgG1) (Morales et al., 1999) each of which recognizes the N-terminal domain of CEACAM1 (Watt et al., 2001); and 12-I40-4, 4/3/17, COL-4, YG-C28F2, D14HD11, B18.7.7, D11-AD11, HEA 81, CLB-gran-10, F34-187, T84.1, B6.2, and B1.1. Monoclonal antibodies 34B1, 26H7, and 5F4 are also discussed in U.S. Patent Pub. No. 2004/0047858, Therapeutic anti-BGP (C-CAM1) antibodies and uses thereof; U.S. Pat. No. 7,132, 255; WO 99/52552, and Morales et al., 163 J. Immunol 1363 (1999). Further assessment of specificity was published in Watt et al., 2001, which described that monoclonal antibody 5F4 binds to a domain within the N-Domain of CEACAM1 that is involved in homophilic interactions between the N-Domains of different CEACAM1 molecules.

Other CEACAM1-Fc fusion proteins have been described, including, for example, the extracellular portion of CEACAM1 fused to human IgFc in a mammalian expression vector (Markel et al., 110 J. Clin. Invest. 943 (2002)); pCEP4-N-CEACAM1-Fc see Gallagher, 71 J. Virol. 3129 (1997)); as well as commercially available sources of CEACAM1 fusion proteins, as known to one of ordinary skill in the art.

Accordingly, in some embodiments of the compositions and methods described herein, CEACAM1 is provided as a ligand for TIM3. In some embodiments, CEACAM1 can be a soluble CEACAM1. "Soluble CEACAM1," as used herein, refers to any form of CEACAM1, including functional variants of CEACAM1, that is dissociated from cell membrane. In some embodiments of the compositions and methods described herein, soluble CEACAM1 is a C-terminal truncated form of full-length CEACAM1. In some embodiments of the compositions and methods described herein, soluble CEACAM1 is a transmembrane-deleted version of CEACAM1. In some embodiments of the compositions and methods described herein, soluble CEACAM1 is an N-terminal region of CEACAM1. In some embodiments of the compositions and methods described herein, soluble CEACAM1 is an ectodomain of CEACAM1. In some embodiments of the compositions and methods described herein, soluble CEACAM1 is a CEACAM1-Fc fusion protein. In some embodiments of the compositions and methods described herein, the ligand for TIM-3 or TIM3-binding molecule includes or comprises a single domain of the extracellular region of CEACAM1, e.g., the IgV domain or a portion of the GFCC'C" face. In some embodiments of the compositions and methods described herein, the soluble CEACAM1 is an alternatively spliced variant of full-length CEACAM1, which includes the IgV domain and some intracellular region. In some embodiments of the compositions and methods described herein, the ligand for TIM-3 or TIM3-binding molecule includes or comprises an extracellular (ectodomain) region of CEACAM1.

For example, the secreted human CEACAM1 isoform 2 (UniProtKB P13688-2) has the amino acids:

```
                                        (SEQ ID NO: 26)
MGHLSAPLHRVRVPWQGLLLTASLLTFWNPPTTAQLTTESMPFNVAEGKE

VLLLVHNLPQQLFGYSWYKGERVDGNRQIVGYAIGTQQATPGPANSGRET

IYPNASLLIQNVTQNDTGFYTLQVIKSDLVNEEATGQFHVYPELPKPSIS

SNNSNPVEDKDAVAFTCEPETQDTTYLWWINNQSLPVSPRLQLSNGNRTL

TLLSVTRNDTGPYECEIQNPVSANRSDPVTLNVTYGPDTPTISPSDTYYR

PGANLSLSCYAASNPPAQYSWLINGTFQQSTQELFIPNITVNNSGSYTCH

ANNSVTGCNRTTVKTIIVTELSPVVAKPQIKASKTTVTGDKDSVNLTCST

NDTGISIRWFFKNQSLPSSERMKLSQGNTTLSINPVKREDAGTYWCEVFN

PISKNQSDPIMLNVNCK
```

Secreted human CEACAM1 isoform 3 (UniProtKB P13688-3) has the amino acids:

```
                                        (SEQ ID NO: 27)
MGHLSAPLHRVRVPWQGLLLTASLLTFWNPPTTAQLTTESMPFNVAEGKE

VLLLVHNLPQQLFGYSWYKGERVDGNRQIVGYAIGTQQATPGPANSGRET

IYPNASLLIQNVTQNDTGFYTLQVIKSDLVNEEATGQFHVYPELPKPSIS

SNNSNPVEDKDAVAFTCEPETQDTTYLWWINNQSLPVSPRLQLSNGNRTL

TLLSVTRNDTGPYECEIQNPVSANRSDPVTLNVTYGPDTPTISPSDTYYR

PGANLSLSCYAASNPPAQYSWLINGTFQQSTQELFIPNITVNNSGSYTCH

ANNSVTGCNRTTVKTIIVTGK.
```

Secreted human CEACAM1 isoform 4 (UniProtKB P13688-4) has the amino acids:

```
                                        (SEQ ID NO: 28)
MGHLSAPLHRVRVPWQGLLLTASLLTFWNPPTTAQLTTESMPFNVAEGKE

VLLLVHNLPQQLFGYSWYKGERVDGNRQIVGYAIGTQQATPGPANSGRET

IYPNASLLIQNVTQNDTGFYTLQVIKSDLVNEEATGQFHVYPELPKPSIS
```

```
-continued
SNNSNPVEDKDAVAFTCEPETQDTTYLWWINNQSLPVSPRLQLSNGNRTL

TLLSVTRNDTGPYECEIQNPVSANRSDPVTLNVTYGPDTPTISPSDTYYR

PGANLSLSCYAASNPPAQYSWLINGTFQQSTQELFIPNITVNNSGSYTCH

ANNSVTGCNRTTVKTIIVTESPVLGEDEAVPGQHHPQHKPCQEGGCWDVL

V
```

The longest isoform, CEACAM1-4L (isoform 1) has 526 amino acids, having the sequence:

```
                                         (SEQ ID NO: 29)
         10         20         30         40
MGHLSAPLHR VRVPWQGLLL TASLLTFWNP PTTAQLTTES 50         60         70         80
MPFNVAEGKE VLLLVHNLPQ QLFGYSWYKG ERVDGNRQIV 90        100        110        120
GYAIGTQQAT PGPANSGRET IYPNASLLIQ NVTQNDTGFY 130        140        150        160
TLQVIKSDLV NEEATGQFHV YPELPKPSIS SNNSNPVEDK 170        180        190        200
DAVAFTCEPE TQDTTYLWWI NNQSLPVSPR LQLSNGNRTL 210        220        230        240
TLLSVTRNDT GPYECEIQNP VSANRSDPVT LNVTYGPDTP 250        260        270        280
TISPSDTYYR PGANLSLSCY AASNPPAQYS WLINGTFQQS 290        300        310        320
TQELFIPNIT VNNSGSYTCH ANNSVTGCNR TTVKTIIVTE 330        340        350        360
LSPVVAKPQI KASKTTVTGD KDSVNLTCST NDTGISIRWF 370        380        390        400
FKNQSLPSSE RMKLSQGNTT LSINPVKRED AGTYWCEVFN 410        420        430        440
PISKNQSDPI MLNVNYNALP QENGLSPGAI AGIVIGVVAL 450        460        470        480
VALIAVALAC FLHFGKTGRA SDQRDLTEHK PSVSNHTQDH 490        500        510        520
SNDPPNKMNE VTYSTLNFEA QQPTQPTSAS PSLTATEIIY

SEVKKQ
```

The foregoing amino acid sequences include a leader sequence (34 amino acids), and the mature peptide starting at QLT. The DNA and amino acid sequences of CEACAM1 isoforms of various species are available on the world wide web from the NCBI, including human (ID: 634), mouse (ID: 26365), rat (ID: 81613), cow (ID: 404118), zebra fish (ID: 114465), dog (ID: 612435), goat (ID: 100384959), and orangutan (ID: 100172828).

CEACAM1 or a portion thereof for use in the compositions and methods described herein can be made by methods known in the art, such as cloning and expression according to molecular methods known to one skilled in the art. In some embodiments of the compositions and methods described herein, the gene encoding CEACAM1, or a portion thereof, is cloned into an expression vector for the overexpression of the respective protein.

Functional variants of CEACAM1 useful in various embodiments of the compositions and methods described herein include molecules representing mutations, additions, deletions, and truncations of full-length CEACAM1, provided such molecules retain the ability to bind to TIM3. Alternatively, in some embodiments, an agent that inhibits CEACAM1-stimulated TIM3 activity or TIM3-stimulated CEACAM1 activity can include or comprise a soluble CEACAM1 protein or conjugate, or protein or antibody; small interfering RNA specific for or targeting CEACAM1 mRNA; or antisense RNA that hybridizes with the messenger RNA of CEACAM1.

Exemplary agents that bind CEACAM1, and methods for identifying such agents and whether such agents enhance or suppress T-cell activity are found, for example, in U.S. Pat. Nos. 7,132,255 and 6,852,320, and the references cited therein, the contents of which are herein incorporated by reference in their entireties.

Moreover, because homophilic binding of CEACAM1 up-regulates TIM3, inhibiting homophilic CEACAM1 binding can be used, in some embodiments, to negatively modulate this up-regulation. Conversely, in some embodiments of the compositions and methods described herein, agents that enhance CEACAM1 homophilic binding can be used to up-regulate TIM3 expression. Hence, some embodiments of the compositions and methods described herein provide for the modulation of CEACAM1 homophilic binding as an approach to modulate TIM3 expression or function in a cell population. Trans-homophilic CEACAM1 binding induces cis-dimerization by an allosteric mechanism transmitted by the N terminal immunoglobulin-like domain. CEACAM1-L homodimer formation is reduced by coexpression of CEACAM1-S and modulated by antibody ligation. Transmembrane signaling by CEACAM1 can operate by alteration of the monomer/dimer equilibrium. Müller et al., 187 J. Cell Biol. 569 (2009). Exemplary agents that selectively decrease or increase homophilic CEACAM1 binding are described, for example, in U.S. Pat. Nos. 7,132,255 and 6,852,320, and the references cited therein, the contents of which are herein incorporated by reference in their entireties.

In some embodiments, a fusion polypeptide comprises a TIM3 or CEACAM1 polypeptide and a second heterologous polypeptide to increase the in vivo stability of the fusion polypeptide, or to modulate its biological activity or localization, or to facilitate purification of the fusion polypeptide. Exemplary heterologous polypeptides that can be used to generate TIM3 or CEACAM1 fusion polypeptides for use in the compositions and methods described herein include, but are not limited to, polyhistidine (His or 6His tag), Glu-Glu, glutathione S transferase (GST), thioredoxin, polypeptide A, polypeptide G, an immunoglobulin heavy chain constant region (Fc), and maltose binding polypeptide (MBP), which are particularly useful for isolation of the fusion polypeptides by affinity chromatography. For the purpose of affinity purification, relevant matrices for affinity chromatography, such as glutathione-, amylase-, and nickel- or cobalt-conjugated resins are used. Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion polypeptides and thereby liberate the recombinant polypeptides therefrom. The liberated polypeptides can then be isolated from the fusion domain by subsequent chromatographic separation. Another fusion domain well known in the art is green fluorescent polypeptide (GFP); such labeled molecules may also be referred to as derivatives. These fusions are well-known to those of skill in the art. See, e.g., PCT US2007/024067.

In some embodiments of the compositions and methods described herein, a bispecific polypeptide agent that specifically binds to both TIM3 and CEACAM1 is used. As used herein, the term "bispecific polypeptide agent" refers to a polypeptide that comprises a first polypeptide domain which has a binding site that has binding specificity for a first target, and a second polypeptide domain which has a binding site that has binding specificity for a second target, i.e., the agent has specificity for two targets, e.g., CEACAM1 and TIM3. The first target and the second target are not the same (i.e., are different targets (e.g., proteins)). The different targets can be co-expressed on the same cell or in cis, as discussed herein for CEACAM1 and TIM3. A bispecific polypeptide agent can bind targets present on a single cell (heterophilic binding in cis), and/or bind one target on one cell and the other on another cell (heterophilic binding in trans). Accordingly, a bispecific polypeptide agent as described herein can selectively and specifically bind to a cell that expresses the first target and the second target. A non-limiting example of a bispecific polypeptide agent is a bispecific antibody construct. Bispecific antibody constructs comprising antigen-binding portions of antibodies specific for two different antigens, e.g., TIM3 and CEACAM1 can be readily constructed by one of skill in the art. Generally, sequences encoding the antigen-binding domain of a first antibody characterized and known to bind a desired epitope on one antigen can be joined, either directly, or through any of a variety of linkers as known to the ordinarily skilled artisan, to sequences encoding the antigen-binding domain of a second antibody characterized and known to bind a desired epitope on a second antigen. Such sequences can be inserted into an appropriate vector and introduced to a cell to produce the bispecific antibody polypeptide by methods known to those of ordinary skill in the art.

As used herein, the term "multispecific polypeptide agent" refers to a polypeptide that comprises at least a first polypeptide domain having a binding site that has binding specificity for a first target, and a second polypeptide domain having a binding site that has binding specificity for a second target, e.g., TIM3 and CEACAM-1 respectively. The first target and the second target are not the same (i.e., are different targets (e.g., proteins)), but can both be present (e.g., co-expressed) on a cell. A multispecific polypeptide agent as described herein can in addition bind one or more additional targets, i.e., a multispecific polypeptide can bind at least two, at least three, at least four, at least five, at least six, or more targets, wherein the multispecific polypeptide agent has at least two, at least, at least three, at least four, at least five, at least six, or more target binding sites respectively. A multispecific polypeptide agent binds a cell that expresses all the targets the agent is specific for more strongly (e.g., with greater avidity) than a cell that expresses only one target, or less targets than the agent is specific for. A non-limiting example of a multispecific polypeptide agent is a multispecific antibody or antigen-binding fragment thereof. For the avoidance of doubt, a bispecific polypeptide agent is a type or subset of multispecific polypeptide agent.

Additionally, stable plasma polypeptides, which typically have a half-life greater than 20 hours in the circulation, can be used, in some embodiments, to construct fusion polypeptides with TIM3 or CEACAM1. Such plasma polypeptides include but are not limited to immunoglobulins, serum albumin or portions thereof, lipopolypeptides, apolipopolypeptides, and transferrin. Sequences that can target the TIM3 or CEACAM1 molecules to a particular cell or tissue type can also be attached to the TIM3 or CEACAM1 to create a specifically-localized TIM3 or CEACAM1 fusion polypeptide. See, e.g., PCT US2007/024067.

In some embodiments, the TIM3 or CEACAM1 polypeptides provided herein, or used in the methods described herein, can further comprise post-translational modifications. Exemplary post-translational polypeptide modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified polypeptides can contain non-amino acid elements, such as lipids, poly- or mono-saccharide, and phosphates. Such molecules can also be referred to as derivatives.

Other derivatives of TIM3 or CEACAM1 peptides for use in the compositions and methods described herein include those that are conjugated or associated with polymers, such as PEG, that can enhance the half-life of the peptide in vivo. PEG modification is well-known in the art. See, e.g., PCT US2007/024067.

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein).

As used herein, "immunoglobulin" refers to a family of polypeptides that retain the immunoglobulin fold characteristic of antibody molecules, which comprise two 13 sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signaling (for example, receptor molecules, such as the PDGF receptor).

A "target site" or "ligand interaction site" on the target molecule means a site, epitope, antigenic determinant, part, domain or stretch of amino acid residues on the target that is a site for binding to a ligand, receptor or other binding partner, a catalytic site, a cleavage site, a site for allosteric interaction, a site involved in multimerisation (such as homomerization or heterodimerization) of the target; or any other site, epitope, antigenic determinant, part, domain or stretch of amino acid residues on the target or antigen that is involved in a biological action or mechanism of the target, e.g., TIM3 or CEACAM1. More generally, a "ligand interaction site" can be any site, epitope, antigenic determinant, part, domain or stretch of amino acid residues on a target or antigen to which a binding site of an agent, or a bispecific or multispecific agent described herein can bind such that the target (and/or any pathway, interaction, signalling, biological mechanism or biological effect in which the target or antigen is involved), e.g., the interaction between CEACAM1 and TIM3 is modulated.

As used herein, a "blocking" antibody or an antibody "antagonist" is one which inhibits or reduces biological activity of the antigen(s) it binds. For example, a CEACAM1/TIM-3 bispecific antagonist antibody binds CEACAM1 and TIM-3 and inhibits the ability of CEACAM1 and TIM-3 to induce or maintain T-cell tolerance. In certain embodiments, the blocking antibodies or antagonist antibodies or portions thereof described herein completely inhibit the biological activity of the antigen(s).

As used herein "domain" refers to a folded protein structure which retains its tertiary structure independently of the rest of the protein. Generally, domains are responsible for discrete functional properties of proteins, and in many cases can be added, removed or transferred to other proteins without loss of function or properties of the remainder of the protein to which it is added or transferred and/or of the domain itself. In the context of an antibody, or a portion thereof, the term "binding domain" refers to such a domain that is directed against an antigenic determinant. By "single antibody variable domain" is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain. Thus, a bispecific polypeptide agent will comprise at least two different binding domains Simple binding assays can be used to screen for or detect agents that bind to TIM3 or CEACAM1, or disrupt the interaction between a TIM3 polypeptide and a CEACAM1 polypeptide. Because TIM3 and CEACAM1 are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners.

Further, agents that inhibit or enhance the CEACAM1/TIM3 interaction for use in the compositions and methods described herein, including recombinant CEACAM1 or TIM3 peptido-mimetics, can be identified by, for example, transfecting cells with CEACAM1 and TIM3 expression vectors (e.g., 293T-cells transfected with human CEACAM1 and TIM3 expression plasmids); contacting the cells with an agent; lysing the cells; and characterizing the CECAM1/TIM3 interaction in comparison with cells not contacted with agent. Cells can be characterized using, for example, co-immunoprecipitation.

Another assay for identifying agents that inhibit or enhance the CEACAM1/TIM3 interaction for use in the compositions and methods described herein analyzes the expression of TIM3 up-regulated by CEACAM1 homophilic ligation. For example, T-cells of mice can be activated, e.g., by administration of SEB, and subsequently T-cells isolated and re-exposed to SEB with or without CEACAM1 (e.g., CEACAM1 N domain-Fc or another peptide-mimetic) and with or without agent, and TIM3 expression compared, for example, by FACS. In samples where cells are contacted with an agent that inhibits the homophilic CEACAM1 ligation, TIM3 expression is lower than in cells lacking the agent. For example, an in vitro assay, such as an ELISA assay with plate bound CEACAM1 or TIM3 fusion proteins can be used and TIM3 or CEACAM1 binding monitored, respectively, in the presence of factors that can modulate these interactions. Similar studies can be performed with cells transfected with CEACAM1 or TIM3 using factors which mimic TIM3 or CEACAM1 binding respectively or compete for binding. Alternatively or additionally, BIACORE (surface plasmon resonance) assays can be performed with soluble CEACAM1 or TIM3 isoforms for binding and competition analyses.

Detection methods useful in such assays include antibody-based methods (i.e., an antibody directed against the "free" protein), direct detection of a reporter moiety incorporated into the "free" protein (such as a fluorescent label), and proximity energy transfer methods (such as a radioactive "free" protein resulting in fluorescence or scintillation of molecules incorporated into the immobilized protein or the solid support).

Another variation of assays to determine binding of a TIM3 protein to a CEACAM1 protein is through the use of affinity biosensor methods. Such methods may be based on the piezoelectric effect, electrochemistry, or optical methods, such as ellipsometry, optical wave guidance, and surface plasmon resonance (SPR). For example, efficacy of an siRNA on the expression of TIM3 or CEACAM1 can be monitored using methods known in the art such as quantitative RT-PCR with specific oligonucleotide primers for each gene respectively, or ELISA for TIM3 and/or CEACAM1 from a sample of peripheral blood. Alternatively, the population of blood cells can be determined by FACS analysis using the markers characteristic of particular populations and subpopulations known in the art or disclosed herein.

Assays to determine the activity of TIM3 are disclosed in U.S. Patent Pub. No. 2005/0191721. In an example of an ex vivo assay, human monocytes are isolated by negative selection from the peripheral blood of healthy subjects using magnetic beads (Miltenyi Biotech). Monocytes ($2 \times 10^5$/well) are stimulated with graded doses of the CEACAM1 polypeptides and cytokine production is measured after 48 hours by ELISA and compared to cytokine production in monocytes stimulated with either TIM3 or a combination of CEACAM1 and TIM3.

In some aspects, provided herein are methods for enhancing or suppressing an immune response in vivo, comprising administering to the subject a therapeutically effective amount of an agent that modulates the interaction of CEACAM1 with TIM3, as described herein. Modulation of T-cell tolerance by molecules that affect the interaction of CEACAM1 with TIM3 is useful for specifically enhancing or suppressing an immune response in vivo, which can be useful for the treatment of conditions related to immune function including autoimmune disease, cancer, and transplantation (e.g., bone marrow or organs). Modulation of T-cell tolerance also is useful in in vitro or non-therapeutic applications including determining whether T-cells of a subject are functional (e.g., proliferation and/or cytotoxic functions), to determine if a treatment has rendered T-cells non-functional, in experimental models of cancer, autoimmune disease, and transplantation, e.g., to determine the effects of increases or decreases in T-cell function on particular organs or physiological processes, and to test for agents which increase or decrease T-cell activity. Other uses will be apparent to one of ordinary skill in the art. The agents that modulate CEACAM1/TIM3 interactions can be used alone as a primary therapy or in combination with other therapeutics as a combination therapy to enhance the therapeutic benefits of other medical treatments.

As used herein, "modulating" or "to modulate" generally means either reducing or inhibiting the activity of, or alternatively increasing the activity of, a target or antigen, such as CEACAM1 or TIM3, as measured using a suitable in vitro, cellular, or in vivo assay. In particular, "modulating" or "to modulate" can mean either reducing or inhibiting the activity of, or alternatively increasing a (relevant or intended) biological activity of, a target or antigen, such as CEACAM1 or TIM3, as measured using a suitable in vitro, cellular or in vivo assay (which will usually depend on the target involved), by at least 5%, at least 10%, at least 25%, at least 50%, at least 60%, at least 70%, at least 80%, at least 90%, or more, inclusive, compared to activity of the target in the same assay under the same conditions but without the presence of an agent. Thus, as used herein, the term "modulating" can refer to an increase or decrease in the TIM3/CEACAM1 interaction relative to a subject not treated with an agent that modulates the TIM3/CEACAM1 interaction. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, inclusive, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more.

As will be clear to the skilled person, "modulating" can also involve effecting a change (which can either be an increase or a decrease) in affinity, avidity, specificity and/or selectivity of a target or antigen, such as CEACAM1 or TIM3, for one or more of its ligands, binding partners, partners for association into a homomultimeric or heteromultimeric form, or substrates; and/or effecting a change (which can either be an increase or a decrease) in the sensitivity of the target or antigen, such as CEACAM1 or TIM3, for one or more conditions in the medium or surroundings in which the target or antigen is present (such as pH, ion strength, the presence of co-factors, etc.), compared to the same conditions but without the presence of a bispecific or multispecific polypeptide agent. Again, this can be determined in any suitable manner and/or using any suitable assay known per se or described herein, depending on the target involved. "Modulating" can also mean effecting a change (i.e., an activity as an agonist, as an antagonist or as a reverse agonist, respectively, depending on the target or antigen, such as CEACAM1 or TIM3, and the desired biological or physiological effect) with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable (in vitro and usually cellular or in assay) assay known per se or described herein, depending on the target or antigen involved.

Modulating can, for example, also involve allosteric modulation of the target, such as CEACAM1 or TIM3; and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

Thus, for example, TIM3 or CEACAM1 activity is "decreased" if one or more signaling activities or downstream read-outs of TIM3 or CEACAM1 activity is reduced by a statistically significant amount, such as by at least 10%, at least 20%, at least 30%, at least 40%, at least 50%, at least 60%, at least 70%, at least 80%, at least 90%, at least 95%, at least 97%, at least 98%, or more, up to and including at least 100%, in the presence of an agent or stimulus relative to the absence of such modulation. As will be understood by one of ordinary skill in the art, in some embodiments, if TIM3 or CEACAM1 activity is decreased, some downstream read-outs will decrease but others can increase (i.e. things that are normally suppressed by TIM3 or CEACAM1 activity), and the converse would be in those embodiments where Tim-3/Ceacam1 activity is increased.

Conversely, TIM3 or CEACAM1 activity is "increased" if one or more signaling activities or downstream read-outs of TIM3 or CEACAM1 activity is increased by a statistically significant amount, for example by at least 10%, at least 20%, at least 30%, at least 40%, at least 50%, at least 60%, at least 70%, at least 80%, at least 90%, at least 95%, at least 97%, at least 98%, or more, up to and including at least 100% or more, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more, in the presence of an agent or stimulus, relative to the absence of such agent or stimulus.

As used herein, the term "promotes T cell tolerance" means that a given treatment or set of conditions leads to increased T cell tolerance. One of ordinary skill in the art can determine whether increased T cell tolerance is achieved using, for example, an SEB model where signal 1 (SEB) strongly stimulates CEACAM1 followed by TIM3 upregulation which is CEACAM1-dependent. In the absence of CEACAM1 (such as in control knock-out mice, for example) or in the presence of factors that block CEACAM1 upregulation or function, TIM3 is unable to be activated upon SEB stimulation. Such a model can be adapted to examine fusion proteins, antibodies, peptides, etc. that modulate CEACAM1 and TIM3 using T cell tolerance as the readout. In normal mice, neonatal injection of staphylococcal enterotoxin B (SEB) induces tolerance in T cells that express reactive T cell receptor (TCR) V beta regions. If T cell tolerance is abrogated or reduced, such as, for example, in the absence of TIM3, then T cells expressing Vbeta8 would have reduced tolerance, i.e., have greater activity.

A subject in need of modulation of T-cell tolerance using the methods described herein includes but is not limited to a subject having or at risk for cancer, a subject diagnosed with an autoimmune disease, an immunocompromised individual, an organ transplant recipient, or a subject suffering from infection by a pathogen.

As used herein, an "immune response" being modulated refers to a response by a cell of the immune system, such as a B cell, T cell (CD4 or CD8), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4+ response or a CD8+ response. Such responses by these cells can include, for example, cytotoxicity, proliferation, cytokine or chemokine production, trafficking, or phagocytosis, and can be dependent on the nature of the immune cell undergoing the response. In some embodiments of the compositions and methods described herein, an immune response being modulated is T-cell tolerance.

In some embodiments of the methods described herein, the subject being administered an agent for modulating CEACAM1 and TIM3 interactions is diagnosed with, has, or suffers from an autoimmune disease. Accordingly, provided herein, in some aspects, are methods of treating a subject having or diagnosed with an autoimmune disorder comprising administering an effective amount of an agent for modulating CEACAM1 and TIM3 interactions. Also provided herein, in some aspects, are agents that modulate CEACAM1 and TIM3 interactions for use in increasing T cell tolerance or treating an autoimmune disorder in a subject.

"Autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include cancer cells.

Accordingly, in some embodiments, the autoimmune diseases to be treated or prevented using the methods described herein, include, but are not limited to: rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, *pemphigus* (e.g., *pemphigus vulgaris*), Grave's disease, autoimmune hemolytic anemia, autoimmune thrombocytopenic purpura, *scleroderma* with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Autoimmune disease has been recognized also to encompass atherosclerosis and Alzheimer's disease. In one embodiment of the aspects described herein, the autoimmune disease is selected from the group consisting of multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, psoriasis and myasthenia gravis.

In some embodiments of the methods described herein, the subject being administered an agent for modulating CEACAM1 and TIM3 interactions has or will receive a transplant, such as an organ transplant. Accordingly, provided herein, in some aspects, are methods of treating a subject who is an organ or tissue transplant recipient, comprising administering an effective amount of an agent for modulating CEACAM1 and TIM3 interactions. In some embodiments, the methods described herein are used for increasing transplantation tolerance in a subject, comprising administering to the subject a therapeutically effective amount of an agent for modulating CEACAM1 and TIM3 interactions; or a cell population contacted with an agent for modulating CEACAM1 and TIM3 interactions, such as T cell population. Also provided herein, in some aspects, are agents that modulate CEACAM1 and TIM3 interactions for use in increasing T cell tolerance or increasing transplantation tolerance in a subject. In some such embodiments, the subject is a recipient of an allogenic transplant. The transplant can be any organ or tissue transplant, including but not limited to heart, kidney, liver, skin, pancreas, bone marrow, skin or cartilage. "Transplantation tolerance," as used herein, refers to a lack of rejection of the donor organ by the recipient's immune system.

In other aspects and embodiments of the methods described herein, the subject being administered an agent for modulating CEACAM1 and TIM3 interactions has a cancer or tumor. Accordingly, provided herein, in some aspects, are methods of treating a subject having a cancer or tumor comprising administering an effective amount of an agent for modulating CEACAM1 and TIM3 interactions. Also provided herein, in some aspects, are agents that modulate CEACAM1 and TIM3 interactions for use in decreasing T cell tolerance or treating a cancer or tumor in a subject.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments described herein, the methods further comprise administering a tumor or cancer antigen to a subject being administered an agent for modulating CEACAM1 and TIM3 interactions described herein.

A number of tumor antigens have been identified that are associated with specific cancers. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer, the immune systems of these patients often fail to respond to the tumor antigens.

In some embodiments of the methods described herein, the methods further comprise administering a chemotherapeutic agent to the subject being administered an agent for modulating CEACAM1 and TIM3 interactions. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE; vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. In addition, the methods of treatment can further include the use of radiation.

In some embodiments of the methods described herein, the subject being administered an agent for modulating CEACAM1 and TIM3 interactions has an infection with a pathogen, such as a bacterium, virus, fungus, or parasite. Also provided herein, in some aspects, are agents that modulate CEACAM1 and TIM3 interactions for use in decreasing T cell tolerance or treating an infection with a pathogen in a subject. In some embodiments of these aspects and all such aspects described herein, the subject has a chronic infection.

Examples of infectious viruses include: Retroviridae (for example, HIV); Picornaviridae (for example, polio viruses, hepatitis A virus; enteroviruses, human coxsackie viruses, rhinoviruses, echoviruses); Caliciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions and methods described herein are contemplated for use in treating infections with these viral agents.

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. The compositions and methods described herein are contemplated for use in treating infections with these fungal agents.

Examples of infectious bacteria include: *Helicobacterpyloris, Borelia burgdorferi, Legionella pneumophilia, Mycobacteria* sps (such as *M. tuberculosis, M avium, M intracellulare, M kansaii, M gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracia, Corynebacterium diphtheriae, corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israeli*. The compositions and methods described herein are contemplated for use in treating infections with these bacterial agents. Other infectious organisms (such as protists) include: *Plasmodium falciparum* and *Toxoplasma gondii*. The compositions and methods described herein are contemplated for use in treating infections with these agents.

In some embodiments of the aspects described herein, the methods further comprise administering an effective amount of a viral, bacterial, fungal, or parasitic antigen in conjunction with an agent for modulating CEACAM1 and TIM3 interactions. Non-limiting examples of suitable viral antigens include: influenza HA, NA, M, NP and NS antigens; HIV p24, pol, gp41 and gp120; Metapneumovirus (hMNV) F and G proteins; Hepatitis C virus (HCV) E1, E2 and core proteins; Dengue virus (DEN1-4) E1, E2 and core proteins; Human Papilloma Virus L1 protein; Epstein Barr Virus gp220/350 and EBNA-3A peptide; Cytomegalovirus (CMV) gB glycoprotein, gH glycoprotein, pp65, IE1 (exon 4) and pp 150; Varicella Zoster virus (VZV) IE62 peptide and glycoprotein E epitopes; Herpes Simplex Virus Glycoprotein D epitopes, among many others. The antigenic polypeptides can correspond to polypeptides of naturally occurring animal or human viral isolates, or can be engineered to incorporate one or more amino acid substitutions as compared to a natural (pathogenic or non-pathogenic) isolate.

As used herein, the terms "treat" "treatment" "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder, such as an autoimmune disease, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "effective amount" as used herein refers to the amount of an agent for modulating CEACAM1 and TIM3 interactions needed to alleviate at least one or more symptom of the disease or disorder, and relates to a sufficient amount of pharmacological composition to provide the desired effect, i.e., promote or inhibit T cell tolerance, for example. The term "therapeutically effective amount" therefore refers to an amount of an agent for modulating CEACAM1 and TIM3 interactions using the methods as disclosed herein, that is sufficient to effect a particular effect when administered to a typical subject. An effective amount as used herein would also include an amount sufficient to delay the development of a symptom of the disease, alter the course of a symptom of disease (for example but not limited to, slow the progression of a symptom of the disease), or reverse a symptom of disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent for modulating CEACAM1 and TIM3 interactions), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

The agents useful according to the compositions and methods described herein, including antibodies and other polypeptides, are isolated agents, meaning that the agents are substantially pure and are essentially free of other substances with which they may be found in nature or in vivo systems to an extent practical and appropriate for their intended use. In particular, the agents are sufficiently pure and are sufficiently free from other biological constituents of their hosts cells so as to be useful in, for example, producing pharmaceutical preparations. Because an isolated agent may be admixed with a pharmaceutically acceptable carrier in a pharmaceutical preparation, the agents may comprise only a small percentage by weight of the preparation.

The agents described herein for modulating CEACAM1 and TIM3 interactions can be administered to a subject in need thereof by any appropriate route which results in an effective treatment in the subject. As used herein, the terms "administering," and "introducing" are used interchangeably and refer to the placement of a polypeptide agent into a subject by a method or route which results in at least partial localization of such agents at a desired site, such as a site of inflammation, such that a desired effect(s) is produced.

In some embodiments, the agents described herein for modulating CEACAM1 and TIM3 interactions are administered to a subject by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the agents for modulating CEACAM1 and TIM3 interactions for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of an agent for modulating CEACAM1 and TIM3 interactions other than directly into a target site, tissue, or organ, such as a tumor site, such that it enters the subject's circulatory system and, thus, is subject to metabolism and other like processes.

For the clinical use of the methods described herein, administration of an agent for modulating CEACAM1 and TIM3 interactions can include formulation into pharmaceutical compositions or pharmaceutical formulations for parenteral administration, e.g., intravenous; mucosal, e.g., intranasal; ocular, or other mode of administration. In some embodiments, an agent for modulating CEACAM1 and TIM3 interactions described herein can be administered along with any pharmaceutically acceptable carrier compound, material, or composition which results in an effective treatment in the subject. Thus, a pharmaceutical formulation for use in the methods described herein can contain an agent for modulating CEACAM1 and TIM3 interactions as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an agent for modulating CEACAM1 and TIM3 interactions. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water;

(16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The agents for modulating CEACAM1 and TIM3 interactions described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a bispecific or multispecific polypeptide agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of an agent for modulating CEACAM1 and TIM3 interactions that can be used in the methods described herein are illustrated below.

Parenteral Dosage Forms. Parenteral dosage forms of an agent for modulating CEACAM1 and TIM3 interactions can also be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol formulations. An agent for modulating CEACAM1 and TIM3 interactions can be packaged in a pressurized aerosol container together with suitable propellants, for example, hydrocarbon propellants like propane, butane, or isobutane with conventional adjuvants. An agent for modulating CEACAM1 and TIM3 interactions can also be administered in a non-pressurized form such as in a nebulizer or atomizer. An agent for modulating CEACAM1 and TIM3 interactions agent can also be administered directly to the airways in the form of a dry powder, for example, by use of an inhaler.

Suitable powder compositions include, by way of illustration, powdered preparations of an agent for modulating CEACAM1 and TIM3 interactions thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the agents for modulating CEACAM1 and TIM3 interactions described herein further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms. In some embodiments of the methods described herein, an agent for modulating CEACAM1 and TIM3 interactions can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the agents for modulating CEACAM1 and TIM3 interactions described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

In some embodiments, an agent for modulating CEACAM1 and TIM3 interactions for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the agent for modulating CEACAM1 and TIM3 interactions agent administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Embodiments of the various aspects described herein can be illustrated by the following paragraphs:

A. A composition for modulating the interaction between TIM3 and CEACAM1, the composition comprising a bispecific agent comprising binding sites specific for TIM3 and CEACAM1.

B. The composition of paragraph A, wherein the bispecific agent binds TIM3 and CEACAM1 and inhibits signaling mediated by the interaction of TIM3 and CEACAM1.

C. The composition of paragraph A, wherein the bispecific agent binds TIM3 and CEACAM1 and increases signaling mediated by the interaction of TIM3 and CEACAM1.

D. The composition of any one of paragraphs A-C, wherein the bispecific agent modulates the interaction between TIM3 and CEACAM1 on the same cell.

E. The composition of any one of paragraphs A-C, wherein the bispecific agent modulates the interaction between TIM3 on a first cell and CEACAM1 on a second cell.

F. The composition of any one of paragraphs A-E, wherein the bispecific agent comprises an antibody or antigen binding portion thereof that specifically binds TIM3 and an antibody or antigen binding portion thereof that specifically binds CEACAM1.

G. A composition for modulating T cell tolerance, the composition comprising an agent that modulates the interaction of CEACAM1 with TIM3.

H. The composition of paragraph G, wherein the agent inhibits the interaction of CEACAM1 with TIM3 and inhibits T cell tolerance.

I. The composition of paragraph G, wherein the agent enhances or mimics the interaction of CEACAM1 with TIM3 and promotes T cell tolerance.

J. The composition of any one of paragraphs G-I, wherein the agent comprises a proteo-mimetic of CEACAM1 that binds to TIM3.

K. The composition of paragraph J, wherein the proteo-mimetic binds to TIM3 and activates signaling mediated by the interaction of TIM3 and CEACAM1.

L. The composition of paragraph J, wherein the proteo-mimetic binds to TIM3 and inhibits signaling mediated by the interaction of TIM3 and CEACAM1.

M. The composition of any one of paragraphs G-L, wherein the agent comprises a proteo-mimetic of TIM3 that binds to CEACAM1.

N. The composition of paragraph M, wherein the proteo-mimetic binds to CEACAM1 and activates signaling mediated by the interaction of TIM3 and CEACAM1.

O. The composition of paragraph M, wherein the proteo-mimetic binds to CEACAM1 and inhibits signaling mediated by the interaction of TIM3 and CEACAM1.

P. The composition of paragraph M, wherein the proteo-mimetic binds comprises SEQ ID NO: 30 or SEQ ID NO: 31.

Q. The composition of paragraph G, wherein the agent comprises a proteo-mimetic of CEACAM1 that binds to TIM3 and a proteo-mimetic of TIM3 that binds to CEACAM1.

R. The composition of paragraph G, wherein the agent comprises a polypeptide that specifically binds TIM-3.

S. The composition of paragraph G, wherein the agent comprises a polypeptide that specifically binds CEACAM1.

T. The composition of paragraph R, wherein the polypeptide that specifically binds TIM3 comprises an antibody or antigen binding portion thereof.

U. The composition of paragraph S, wherein the polypeptide that specifically binds CEACAM1 comprises an antibody or antigen binding portion thereof.

V. The composition of paragraph G, wherein the agent comprises an antibody or antigen-binding portion thereof that specifically binds TIM3 and an antibody or antigen-binding portion thereof that specifically binds CEACAM1.

W. A method of modulating the interaction of CEACAM1 with TIM3, the method comprising contacting a cell with an agent that binds CEACAM1 and/or TIM3 and modulates binding of CEACAM1 to TIM3.

X. The method of paragraph W, wherein the agent increases signaling mediated by CEACAM1 interaction with TIM3.

Y. The method of paragraph W, wherein the agent inhibits signaling mediated by CEACAM1 interaction with TIM3.

Z. The method of paragraph W, wherein the agent comprises binding sites specific for both CEACAM1 and TIM3.

AA. The method of paragraph W, wherein the agent comprises a bispecific polypeptide agent comprising binding sites specific for TIM3 and CEACAM1.

BB. The method of paragraph Z, wherein the bispecific polypeptide agent comprises an antibody or antigen binding portion thereof that specifically binds TIM3 and an antibody or antigen binding portion thereof that specifically binds CEACAM1.

CC. A method of modulating T cell tolerance, the method comprising administering an agent that modulates the interaction of TIM3 with CEACAM1.

DD. The method of paragraph CC, wherein the agent increases signaling mediated by CEACAM1 interaction with TIM3 and increases T cell tolerance.

EE. The method of paragraph CC, wherein the agent inhibits signaling mediated by CEACAM1 interaction with TIM3.

FF. The method of paragraph CC, wherein the agent comprises binding sites specific for both CEACAM1 and TIM3.

GG. A method of modulating T cell tolerance in a subject in need thereof, the method comprising administering an effective amount of an agent that modulates the interaction of TIM3 with CEACAM1.

HH. The method of paragraph GG, wherein the agent increases or mimics signaling mediated by CEACAM1 interaction with TIM3 and increases T cell tolerance.

II. The method of paragraph HH, wherein the subject has an autoimmune disorder.

JJ. The method of paragraph HH, wherein the subject is a transplant recipient.

KK. The method of paragraph GG, wherein the agent inhibits signaling mediated by CEACAM1 interaction with TIM3 and inhibits T cell tolerance.

LL. The method of paragraph KK, wherein the subject has cancer or a tumor.

MM. The method of paragraph KK, wherein the subject is a transplant recipient

NN. The method of any one of paragraphs GG-MM, wherein the agent comprises a proteo-mimetic of CEACAM1 that binds to TIM3.

OO. The method of paragraph NN, wherein the proteo-mimetic binds to TIM3 and activates signaling mediated by the interaction of TIM3 and CEACAM1.

PP. The method of paragraph NN, wherein the proteo-mimetic binds to TIM3 and inhibits signaling mediated by the interaction of TIM3 and CEACAM1.

QQ. The method of any one of paragraphs GG-OO, wherein the agent comprises a proteo-mimetic of TIM3 that binds to CEACAM1.

RR. The method of paragraph QQ, wherein the proteo-mimetic binds to CEACAM1 and activates or mimics signaling mediated by the interaction of TIM3 and CEACAM1.

SS. The method of paragraph QQ, wherein the proteo-mimetic binds to CEACAM1 and inhibits signaling mediated by the interaction of TIM3 and CEACAM1.

TT. The method of paragraph QQ, wherein the proteo-mimetic binds comprises SEQ ID NO: 30 or SEQ ID NO: 31.

UU. The method of paragraph QQ, wherein the agent comprises a proteo-mimetic of CEACAM1 that binds to TIM3 and a proteo-mimetic of TIM3 that binds to CEACAM1.

VV. The method of any one of paragraphs CC-MM, wherein the agent comprises a polypeptide that specifically binds TIM-3.

WW. The method of any one of paragraphs CC-MM, wherein the agent comprises a polypeptide that specifically binds CEACAM1.

XX. The method of paragraph VV, wherein the polypeptide that specifically binds TIM3 comprises an antibody or antigen binding portion thereof.

YY. The method of paragraph WW, wherein the polypeptide that specifically binds CEACAM1 comprises an antibody or antigen binding portion thereof.

ZZ. The method of any one of paragraphs VV-YY, wherein the agent comprises an antibody or antigen-binding portion thereof that specifically binds TIM3 and an antibody or antigen-binding portion thereof that specifically binds CEACAM1.

AAA. The method of any one of paragraphs VV-ZZ, wherein the agent comprises binding sites specific for both CEACAM1 and TIM3.

BBB. An agent that modulates the interaction of TIM3 with CEACAM1 for use in modulating T cell tolerance in a subject.

CCC. The use of paragraph BBB, wherein the agent the agent increases or mimics signaling mediated by CEACAM1 interaction with TIM3 and increases T cell tolerance.

DDD. The use of paragraph CCC wherein the subject has an autoimmune disorder.

EEE. The use of paragraph CCC, wherein the subject is a transplant recipient.

FFF. The use of paragraph BBB, wherein the agent inhibits signaling mediated by CEACAM1 interaction with TIM3 and inhibits T cell tolerance.

GGG. The use of paragraph FFF, wherein the subject has cancer or a tumor.

HHH. The use of paragraph FFF, wherein the subject is a transplant recipient

III. The use of any one of paragraphs BBB-HHHH, wherein the agent comprises a proteo-mimetic of CEACAM1 that binds to TIM3.

JJJ. The use of paragraph III, wherein the proteo-mimetic binds to TIM3 and activates signaling mediated by the interaction of TIM3 and CEACAM1.

KKK. The use of paragraph III, wherein the proteo-mimetic binds to TIM3 and inhibits signaling mediated by the interaction of TIM3 and CEACAM1.

LLL. The use of any one of paragraphs BBB-HHHH, wherein the agent comprises a proteo-mimetic of TIM3 that binds to CEACAM1.

MMM. The use of paragraph LLL, wherein the proteo-mimetic binds to CEACAM1 and activates or mimics signaling mediated by the interaction of TIM3 and CEACAM1.

NNN. The use of paragraph MMM, wherein the proteo-mimetic binds to CEACAM1 and inhibits signaling mediated by the interaction of TIM3 and CEACAM1.

OOO. The use of paragraph MMM, wherein the proteo-mimetic binds comprises SEQ ID NO: 30 or SEQ ID NO: 31.

PPP. The use of paragraph MMM, wherein the agent comprises a proteo-mimetic of CEACAM1 that binds to TIM3 and a proteo-mimetic of TIM3 that binds to CEACAM1.

QQQ. The use of any one of paragraphs BBB-HHHH, wherein the agent comprises a polypeptide that specifically binds TIM-3.

RRR. The use of any one of paragraphs BBB-HHHH, wherein the agent comprises a polypeptide that specifically binds CEACAM1.

SSS. The use of paragraph RRR, wherein the polypeptide that specifically binds TIM3 comprises an antibody or antigen binding portion thereof.

TTT. The use of paragraph SSS, wherein the polypeptide that specifically binds CEACAM1 comprises an antibody or antigen binding portion thereof.

UUU. The use of any one of paragraphs QQQ-TTT, wherein the agent comprises an antibody or antigen-binding portion thereof that specifically binds TIM3 and an antibody or antigen-binding portion thereof that specifically binds CEACAM1.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

EXAMPLES

Example 1. CEACAM1 and TIM3 Interactions 293T-cells were transfected with human CEACAM1 and TIM3 expression plasmids. Whole cell lysate was prepared 48 hours after transfection for co-immunoprecipitation by anti-HA mAb for TIM3 and western blot for CEACAM1 (anti-Flag). (Left panel) or co-immunoprecipitation by anti-flag for Ceacam1 and western blot for Tim-3 (anti-HA) (Right panel). As depicted in FIG. 1, CEACAM1 exhibits a biochemical interaction with TIM3.

Figure 2B:
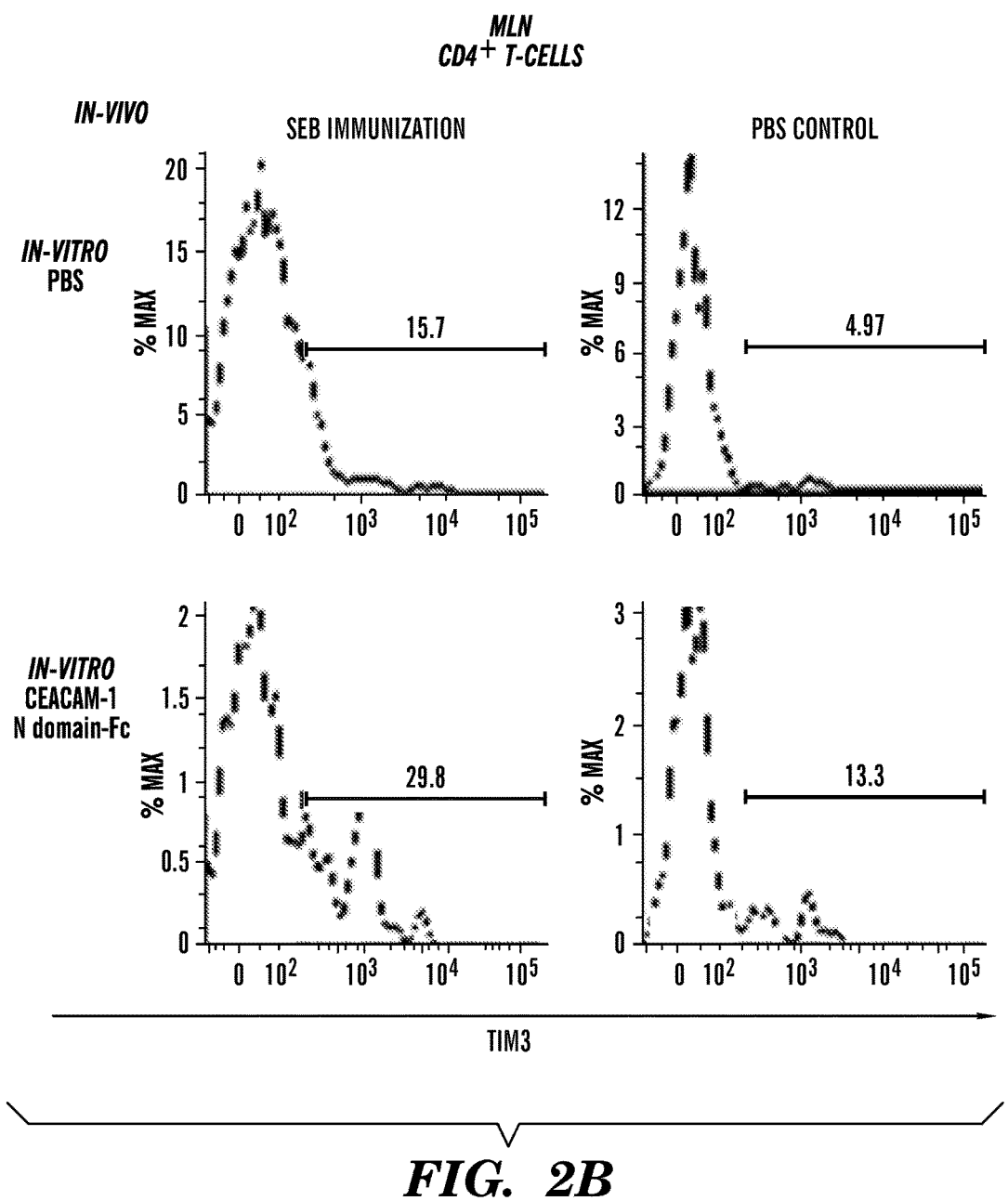
FIG. 2B shows a mouse CEACAM1-N domain fusion protein up-regulates TIM-3 in vitro. CD4$^+$T-cells were isolated from 8-days-SEB-immunized mice or PBS control mice. Cells were in vitro re-stimulated with 0.5 mg/ml CEACAM1-N domain fusion protein or PBS as control. After 48 hours, TIM3 expression was examined on gated CD4$^+$T-cells.

Mice were injected intraperitoneally with 100 μg/100 μl SEB, or 100 μl of PBS as control. After 8 days (before the crash of Vβ8 T-cells), the expression of CEACAM1 on Vβ8 T-cells (SEB-reactive), and on of Vβ6 T-cell (SEB non-reactive) from mice in both of these groups was analyzed. As shown in the data from FACS analysis (FIG. 2A) maximal CEACAM1 expression was demonstrated on the proportion of SEB-reactive T-cells during the 8-days SEB-administration. $CD4^+$T-cells were isolated from 8-days-SEB-immunized mice or PBS control mice. Cells were in vitro re-stimulated with 0.5 mg/ml SEB or PBS as control. After 48 hours, TIM3 expression was examined on gated $CD4^+$T-cells. Mouse CEACAM1-N domain fusion protein up-regulates TIM-3 in vitro, as shown in FIG. 2B.

Figure 3:
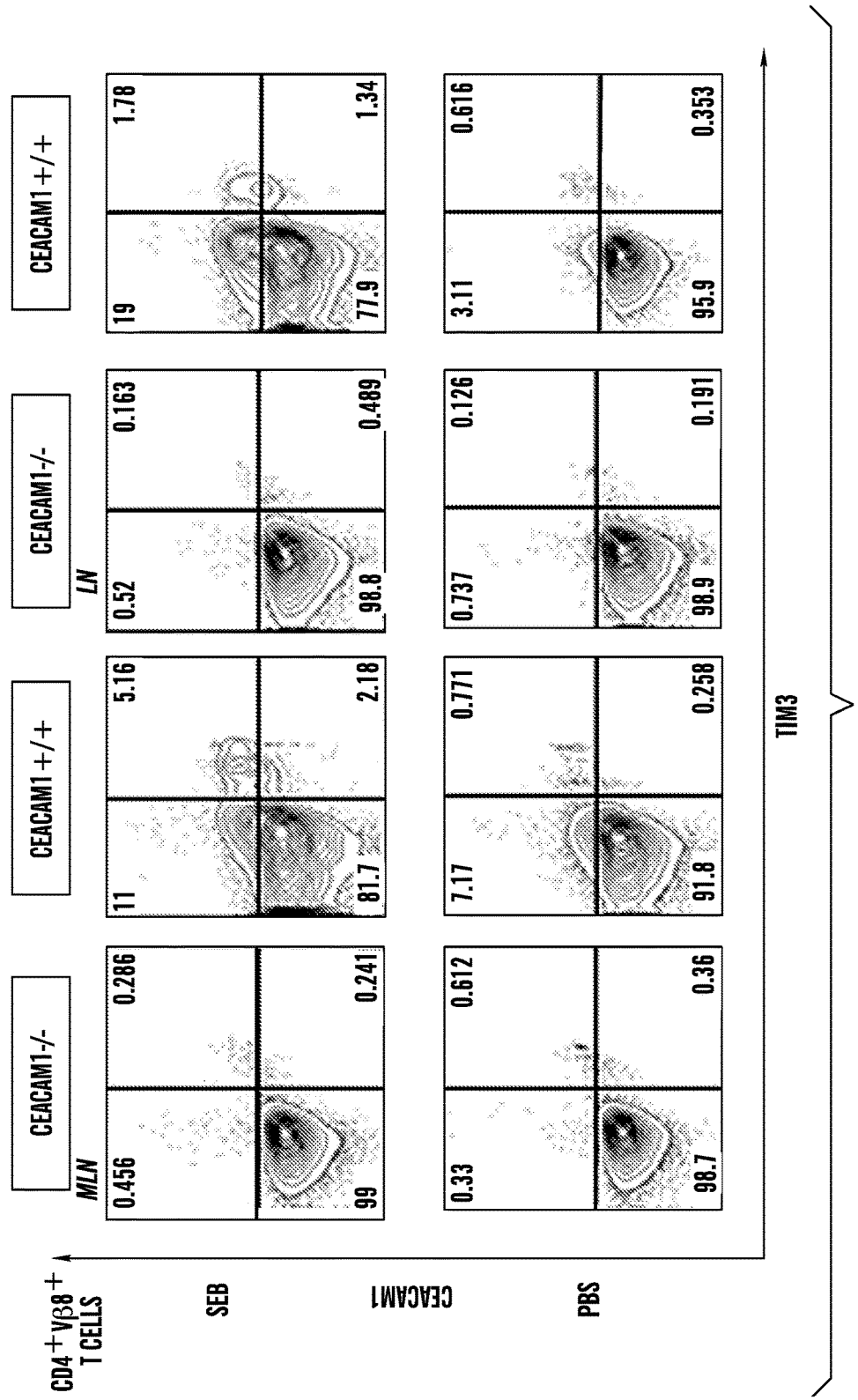
FIG. 3 demonstrates deficient induction of TIM3 in CEACAM1$^{-/-}$ mice. Mice were intraperitoneally injected with 100 µg/100 µl SEB, or 100 µl of PBS as control. After 8 days of SEB injection, the expression of CEACAM1 and TIM3 expression on CD4$^+$Vβ8$^+$ T-cells of mesenteric lymph nodes (MLN) and lymph nodes (LN) from WT (Ceacam1$^{+/+}$) and KO (Ceacam1$^{-/-}$) mice were analyzed.

Mice were intraperitoneally injected with 100 μg/100 μl SEB, or 100 μl of PBS as control. After 8 days of SEB injection, the expression of CEACAM1 and TIM3 expression on $CD4^+V\beta8^+$T-cells of mesenteric lymph nodes (MLN) and lymph nodes (LN) from WT ($Ceacam1^{+/+}$) and KO ($CEACAM1^{-/-}$) mice were analyzed. It was demonstrated that there is deficient induction of TIM3 in $Ceacam1^{-/-}$ mice (FIG. 3).

CEACAM1 expression was analyzed by quantitative PCR. CEACAM1 expression in pan T-cells stimulated with CD3, and CD3/CD8 for 0, 2 or 4 days, which is low on resting T-cells, is transcriptionally regulated by ligation of T-cells through the TCR/CD3 complex (signal 1) but negatively regulated when the TCR/CD3 complex is co-engaged by the classical co-stimulatory signal (signal 2) provided by CD28 (FIG. 4).

Example 2. CEACAM1 and TIM3 Interactions on T-Cells in Cancer

Figure 6:
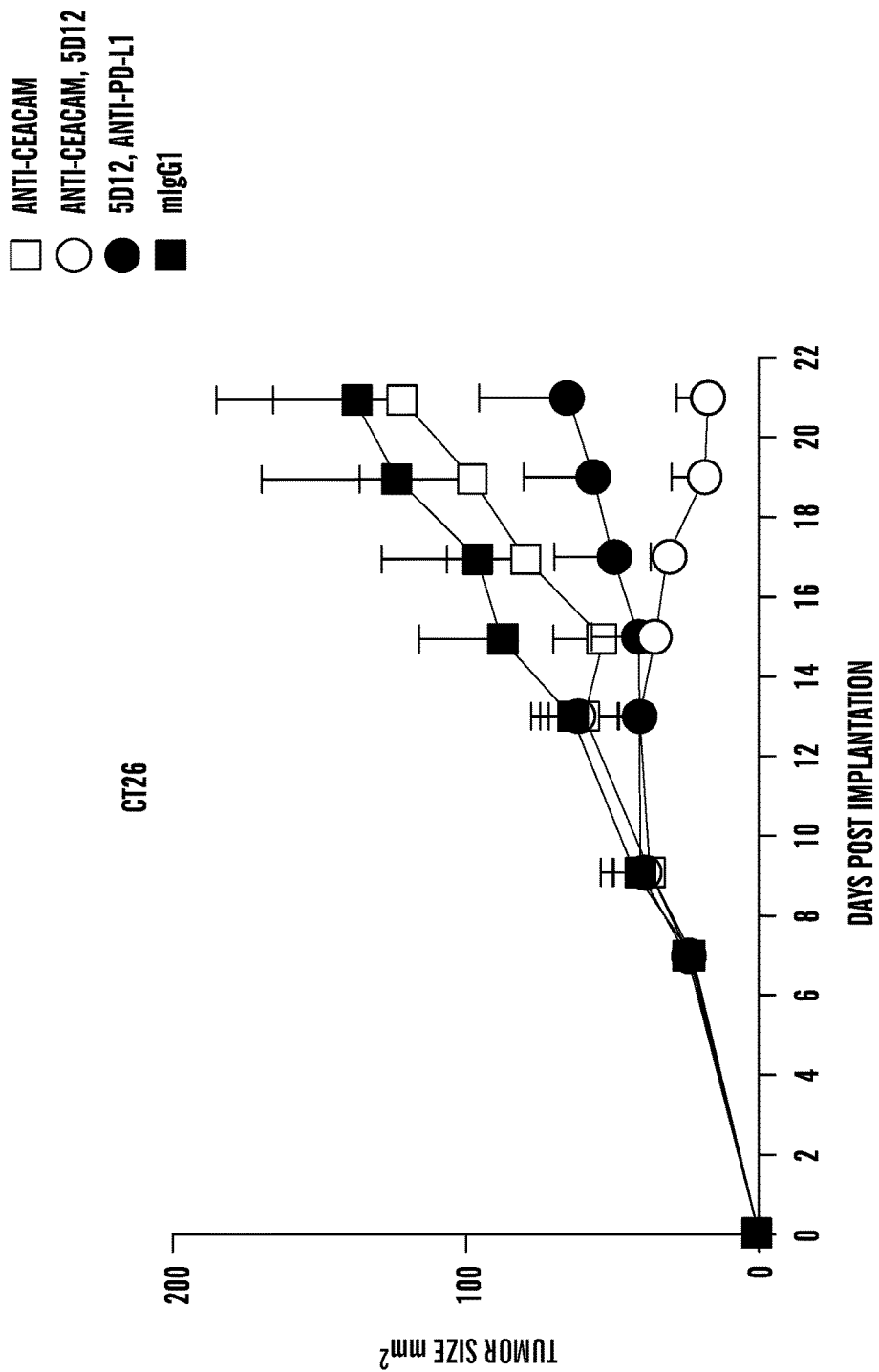
FIG. 6 demonstrates that anti-Tim3 and anti-Ceacam1 antibodies synergize to induce tumor regression. Using the colorectal cell line CT26 in an in vivo mouse model, co-blockade of CEACAM1 and TIM3 relative to PD-L1 and TIM3 was examined and its effects on tumor growth subcutaneously were measured. Co-blockade of CEACAM1 and TIM3 results in significant suppression of cancer and tumor size and growth, and exceeds that seen with co-blockade of TIM3 and PD-L1.
Figure 7:
FIG. 7 shows examples of TIM3 peptides expected to bind to CEACAM1. Peptide 1 is a linear peptide from aa residues 58-77 (SEQ ID NO: 30). Peptide 2 is a non-linear peptide that includes amino acids 58-62, a SGSG linker and amino acids 112-119 of TIM3 (SEQ ID NO: 31).
Figure 8A:
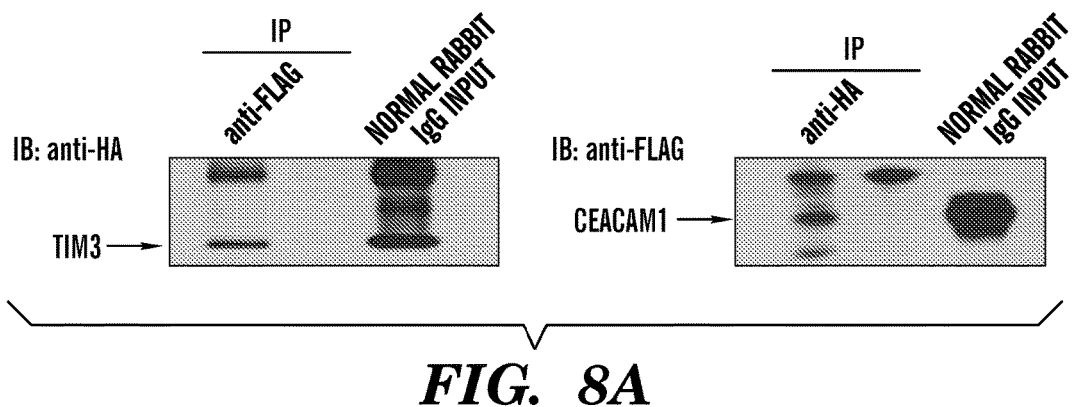
FIGS. 8A-8C show a biochemical demonstration that human CEACAM1 and TIM3 interact specifically in cis and around the C-C' loop of TIM3. Human embryonic kidney (HEK) cells were transfected with FLAG-tagged CEACAM1 and/or HA-tagged TIM3 which was wild type (WT) mutated at various positions in and around the TIM3 C-C' loop and adjacent to the FG loop. 48 hours after transfection, lysates were immunoprecipitated (IP) with either FLAG- or HA specific monoclonal antibodies (mAb) and immunoblotted (IB) for CEACAM1 (with either anti-FLAG or anti-CEACAM1 5F4 mAbs) or TIM3 (anti-HA mAb).
Figure 8B:
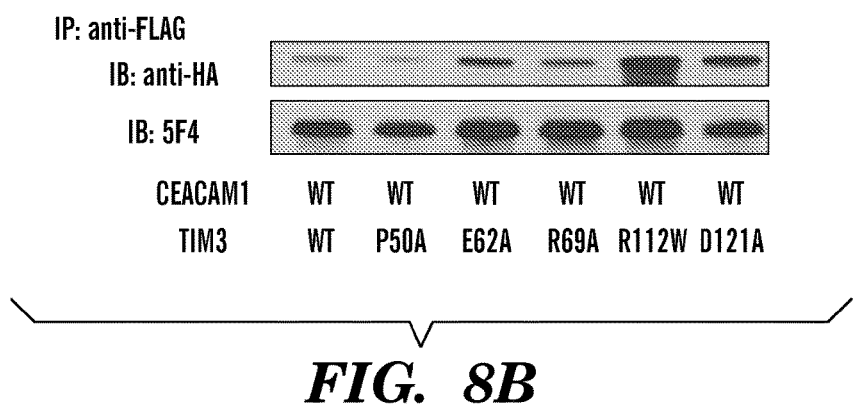
Figure 8C:
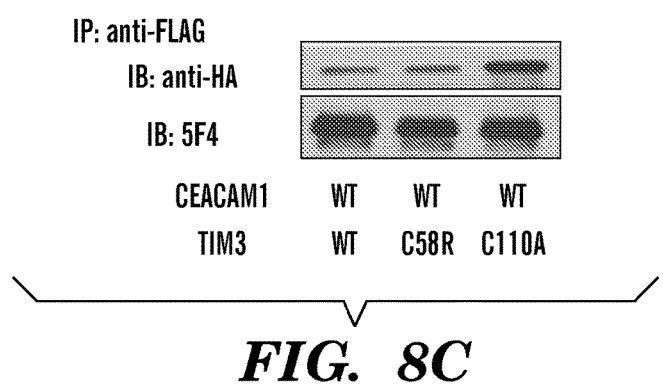
Figure 9:
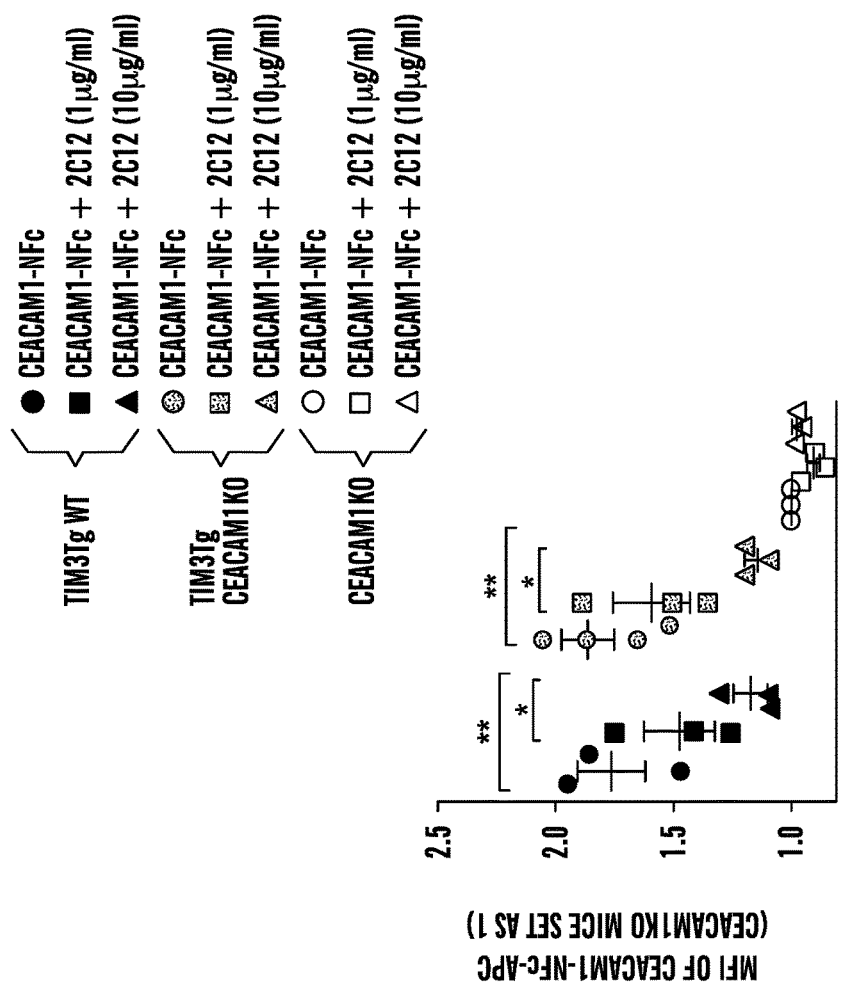
FIG. 9 shows evidence that CEACAM1 functionally binds to TIM3 in trans between two apposing cells. More specifically, CEACAM1 IgV N-domain binds in trans to TIM3 on primary transgenic T cells and the interaction is blocked with an anti-TIM3 monoclonal antibody (2C12). Primary naïve T cells were isolated from B6 (WT) mice with transgenic (Tg) overexpression of TIM3 in T cells, wherein TIM3 is controlled by the human CD2 promotor, and TIM3 Tg mice crossed to Ceacam1$^{-/-}$ mice (knockout) or Ceacam1$^{-/-}$ mice. Primary T cells were stained with a mouse N-domain as an Fc fusion protein in the presence or absence of varying concentrations of a TIM3 specific monoclonal antibody, 2C12, to block binding. *, P<0.05; **, P<0.01
Figure 10A:
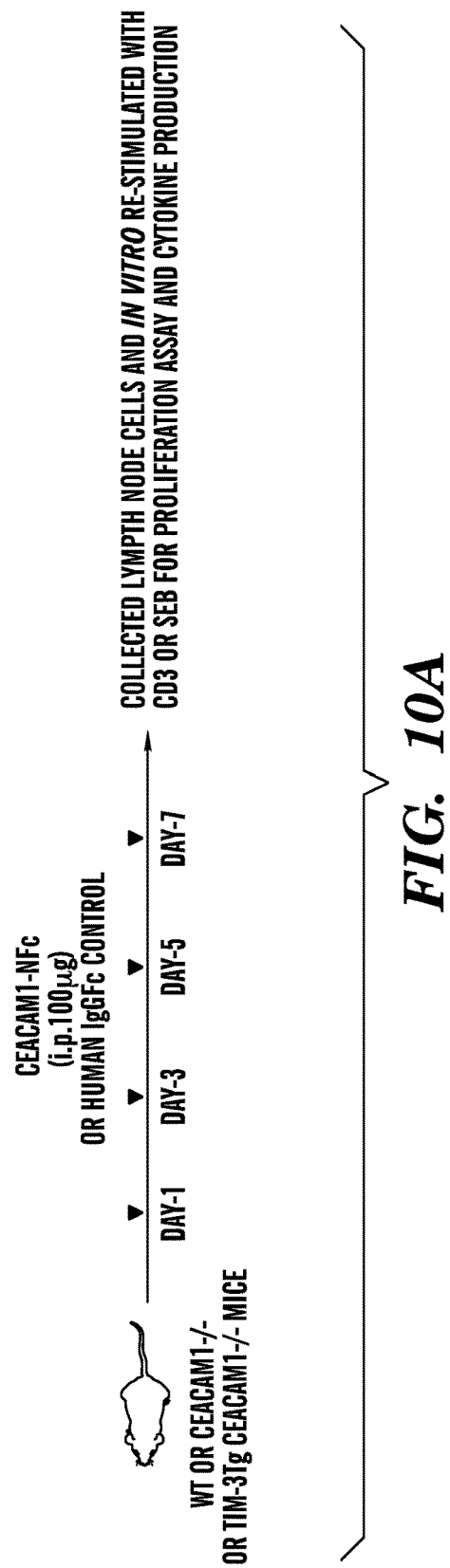
FIGS. 10A-10B demonstrate that administration of CEACAM1 N domain as an Fc fusion protein in vivo can bind in trans to TIM3 on primary T cells that transgenically overexpress TIM3 and induce tolerance.
Figure 10B:
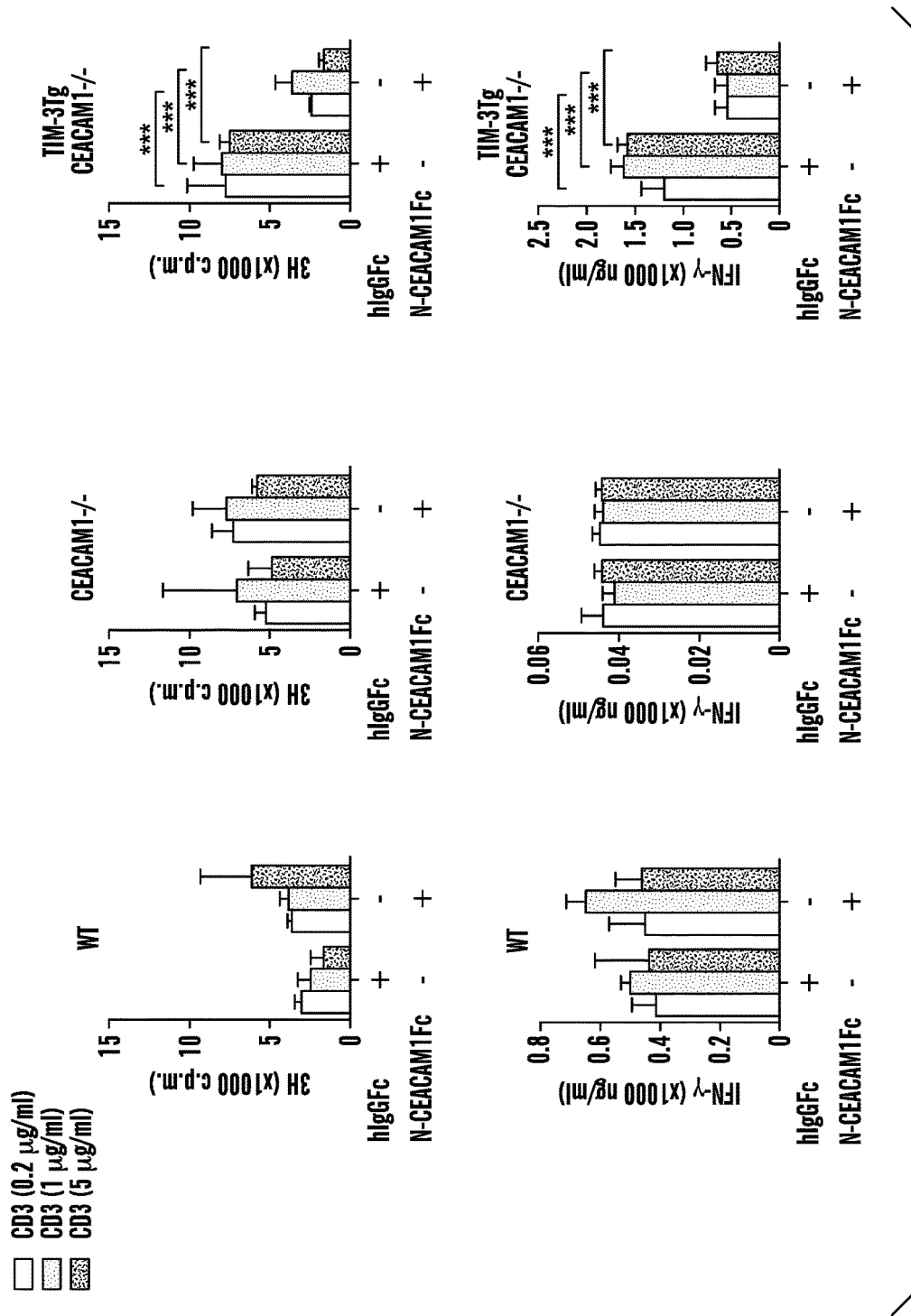
Figure 10B:
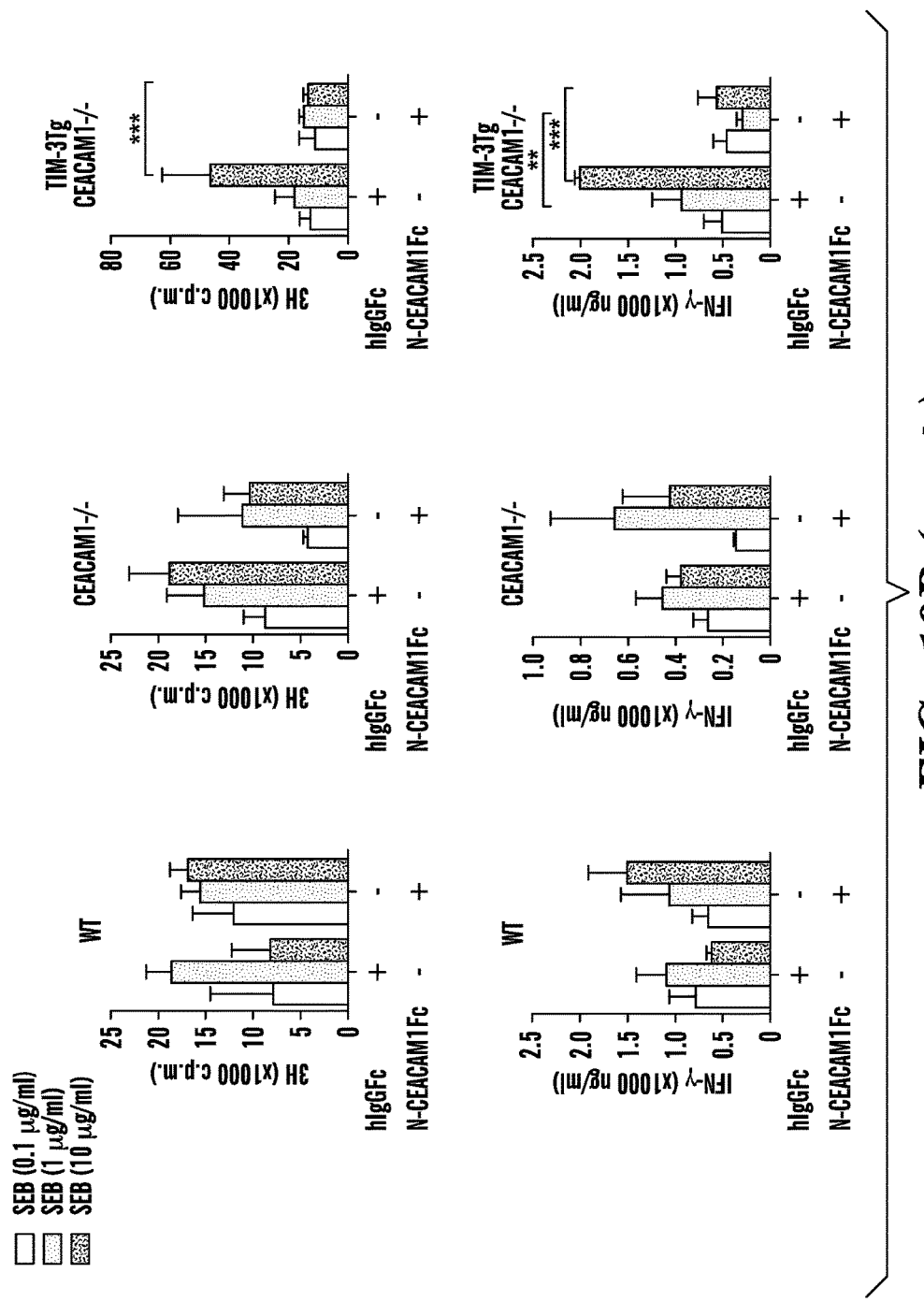
Figure 11:
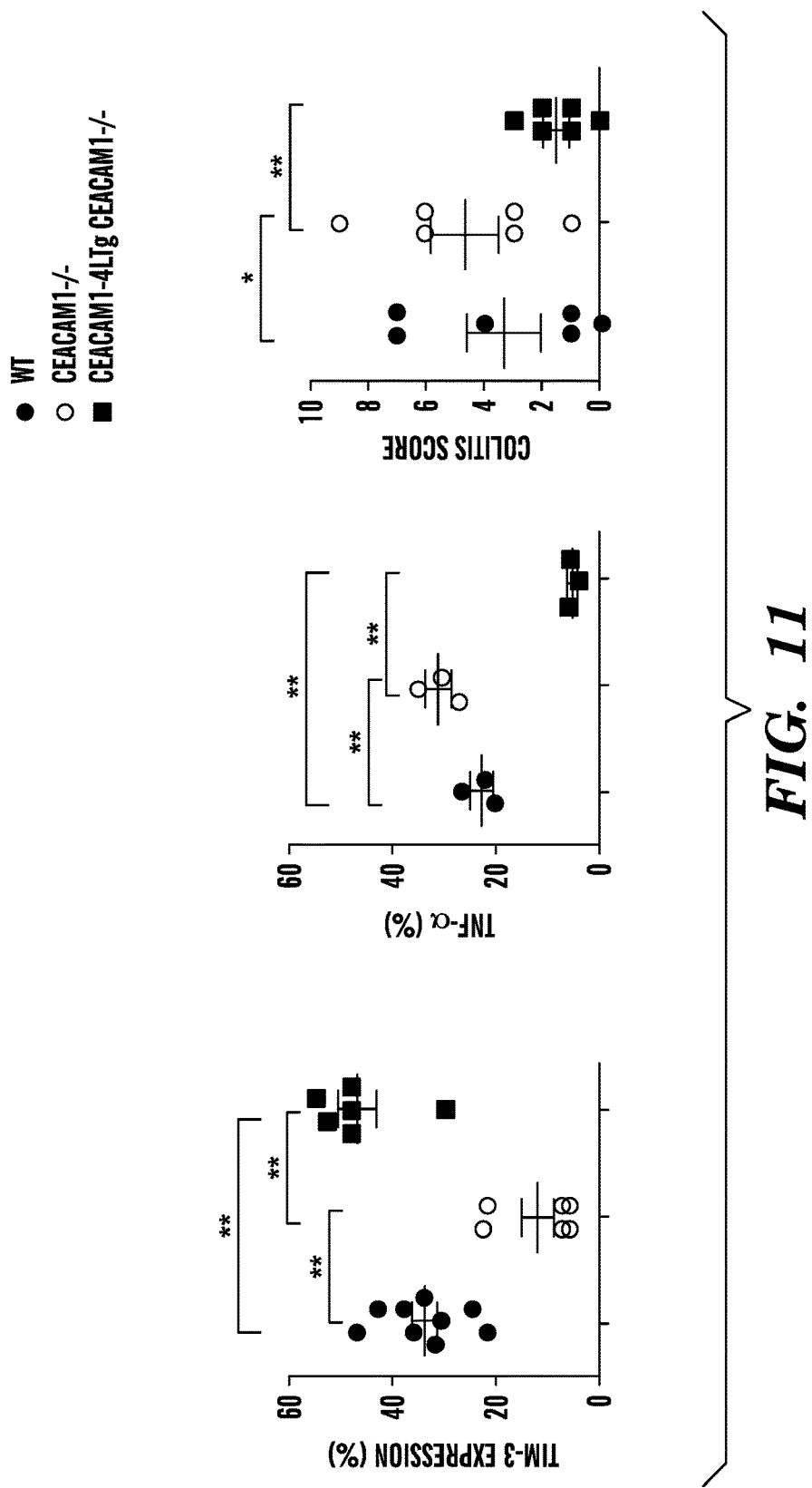
FIG. 11 demonstrates that transgenic reconstitution of CEACAM1-4L variant into T cells of Ceacam1$^{-/-}$ mice restores TIM3 expression on activated T cells in vivo after transfer of naïve T cells into Rag2-deficient recipient mice in association with decreased colitis and decreased TNF expression by adoptively transferred T cells. Naïve CD62L$^+$ CD4$^+$ T cells from WT, Ceacam1$^{-/-}$ or CEACAM1-4L Tg/Ceacam1$^{-/-}$ mice were transferred into Rag2$^{-/-}$ mice and at 8 weeks mice examined for TIM3 and TNF expression on adoptively transferred T cells and the severity of colitis. Colitis score represents quantitative histopathology. Protection provided by restoration of CEACAM1 expression on T cells is demonstrated. Rag2 knockout recipients provide CEACAM1 in trans. *, P<0.05; **, P<0.01
Figure 12:
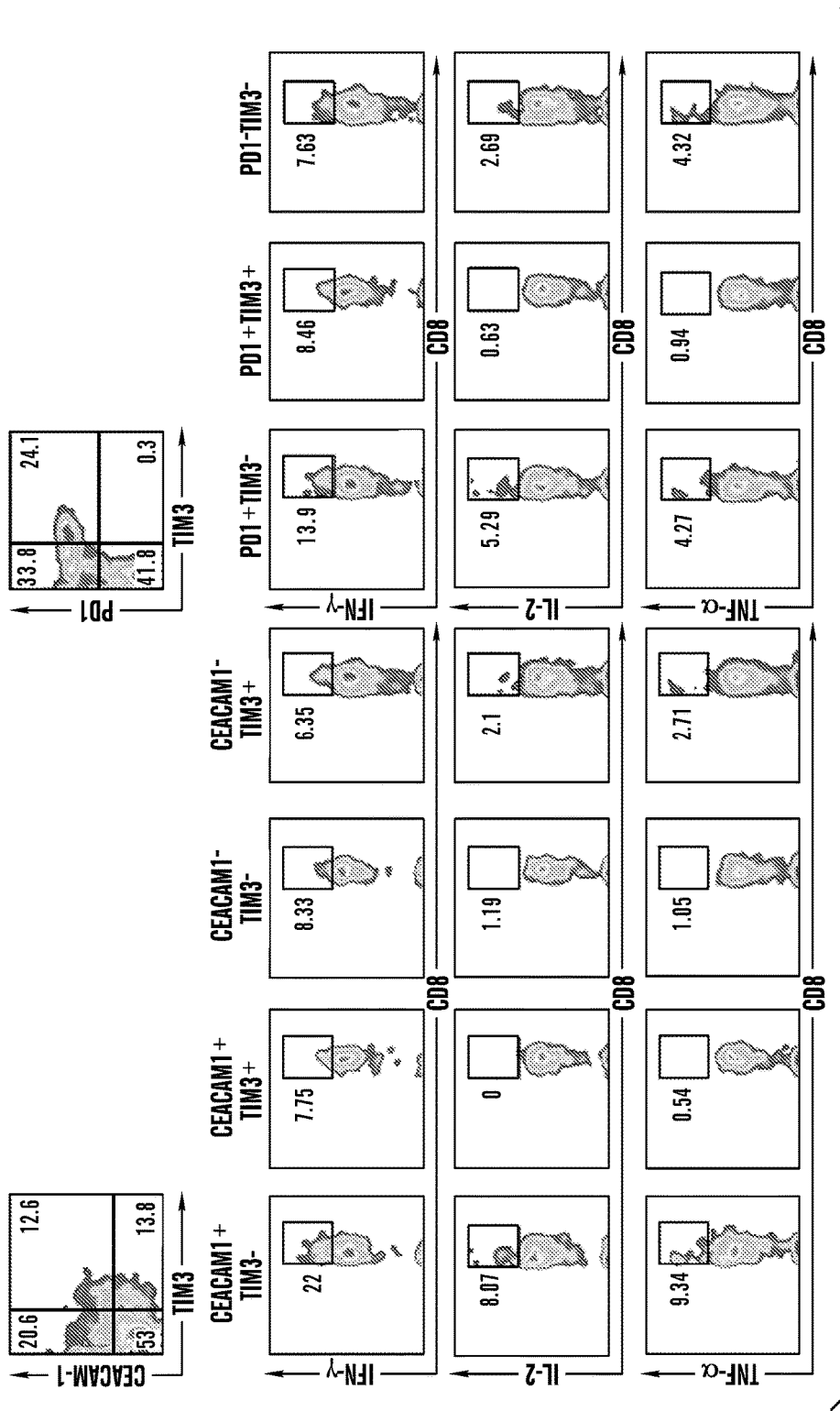
FIG. 12 demonstrates that CEACAM1 and TIM3 track together in exhausted T cells during anti-cancer immune responses.
Figure 13A:
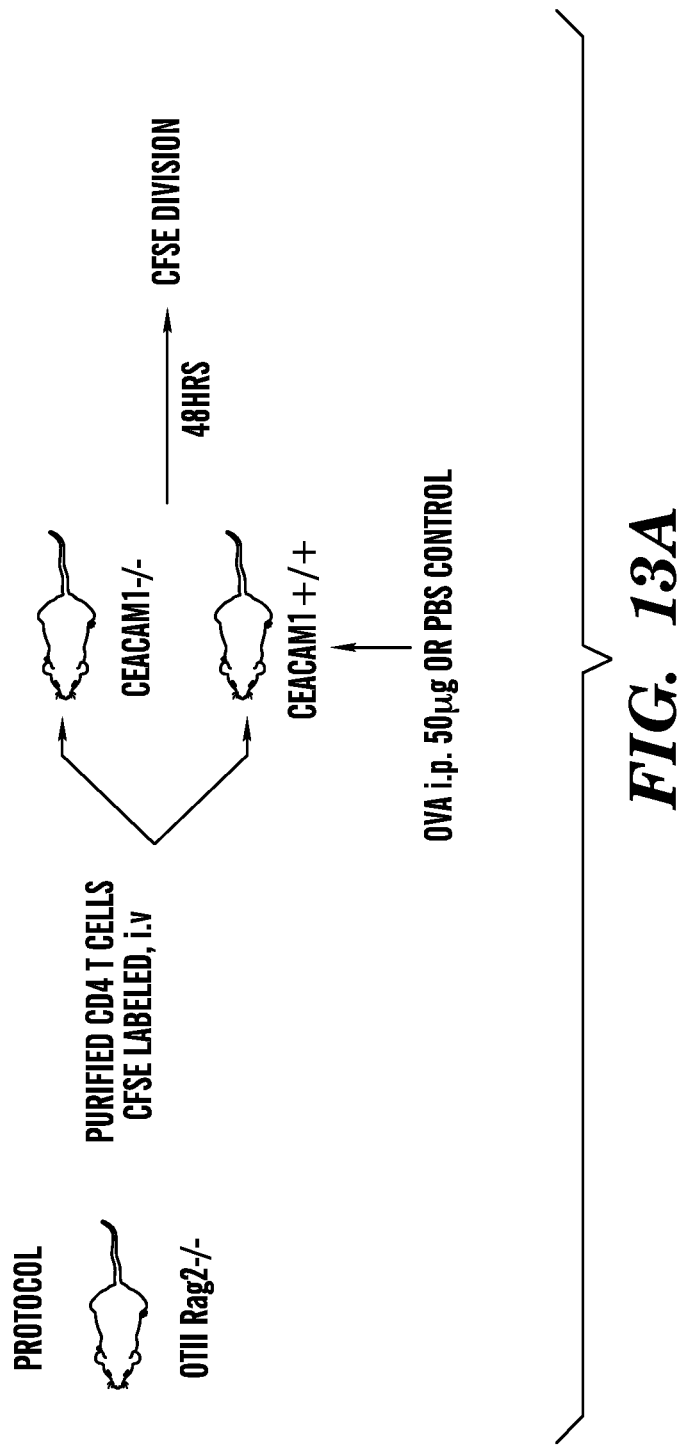
FIGS. 13A-13C demonstrate that CEACAM1 and TIM3 are required for antigen specific tolerance. More specifically, adoptive transfer of CFSE labeled OTII-Rag2KO (knockout) primary naïve T cells into CEACAM1-deficient recipients leads to decreased tolerance in response to antigen (ovalbumin) stimulation as shown by increased proliferation of the transferred cells in vivo.
Figure 13B:
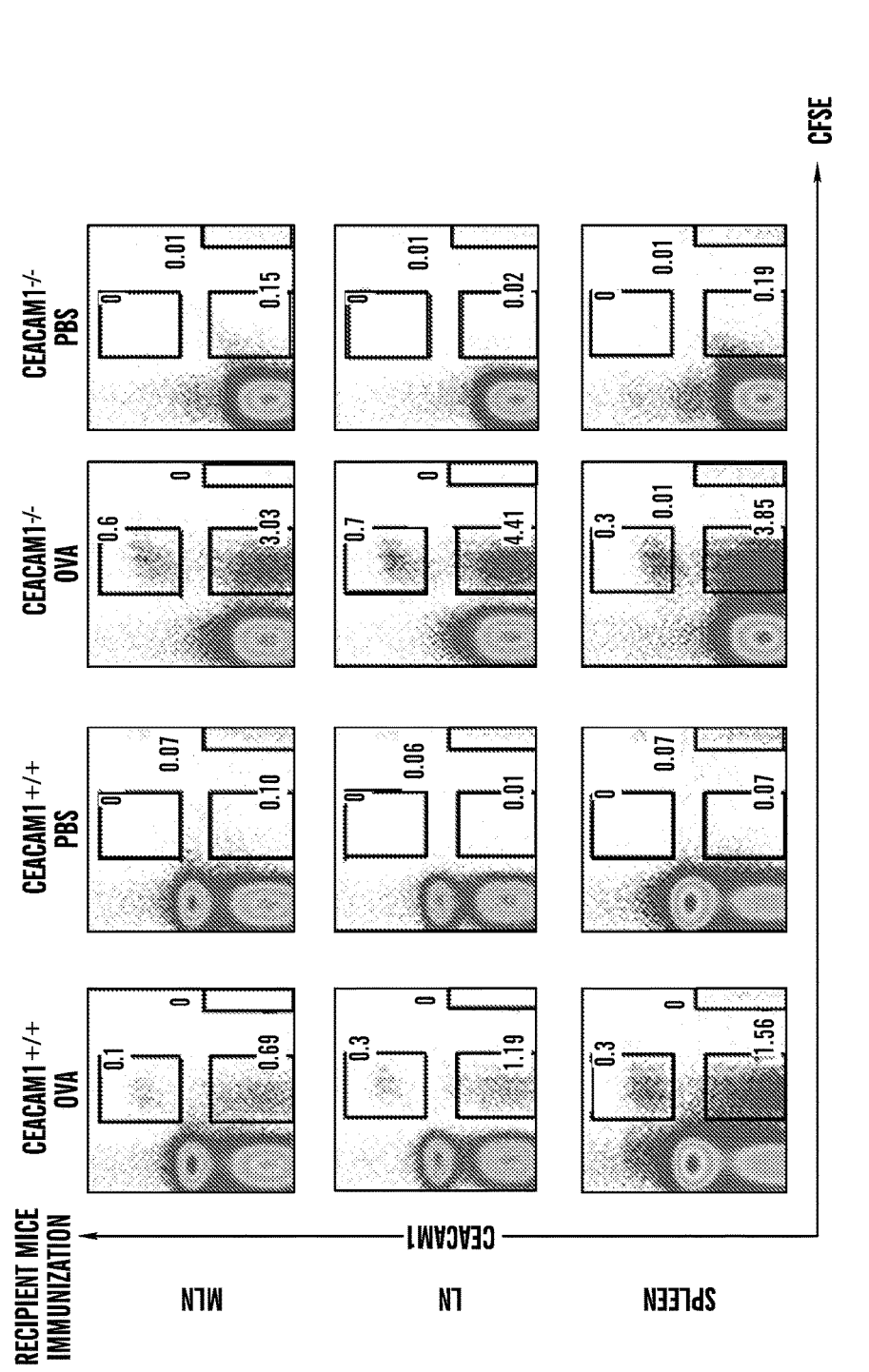
Figure 13C:
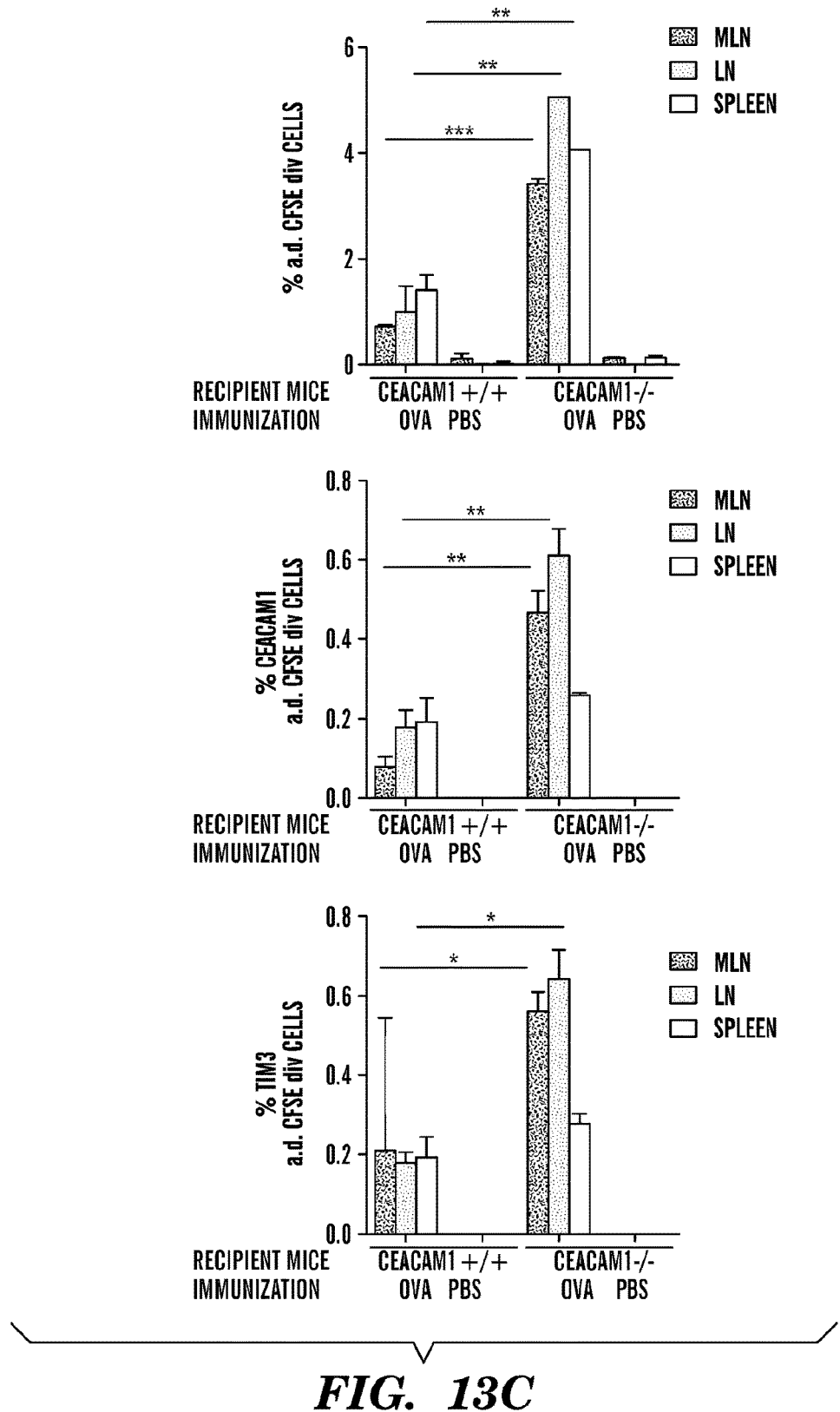
Figure 14:
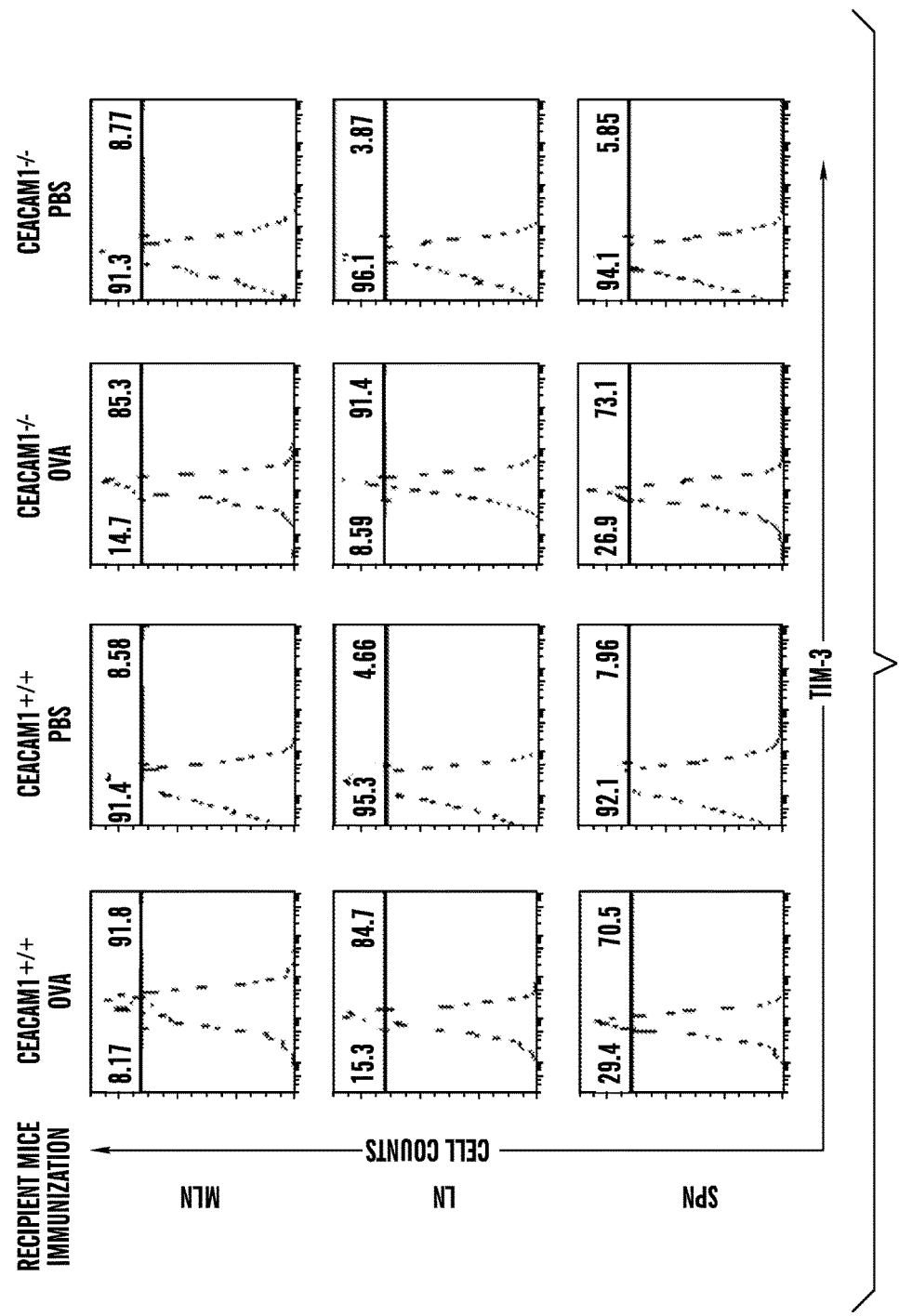
FIG. 14 demonstrates that adoptive transfer of OTII-Rag2 KO primary naïve T cells into CEACAM1-deficient or sufficient mice leads to upregulation of TIM3, indicating that expression of CEACAM1 in trans is not required for upregulation of TIM3 on activated T cells, although CEACAM1 is required in cis. In addition, TIM3 expression is only observed on CEACAM1$^+$ T cells, indicating that these two cell surface molecules are coordinately expressed. OT11 Tg-Rag ko T cells were adoptively transferred into WT or CEACAM1-deficient mice and activated antigen (ovalbumin) and the expression of CEACAM1 and TIM3 examined by flow cytometry on the Tg T cells. Both molecules were coordinately expressed on the activated T cells regardless of CEACAM1 expression on the antigen presenting cell.
Figure 14:
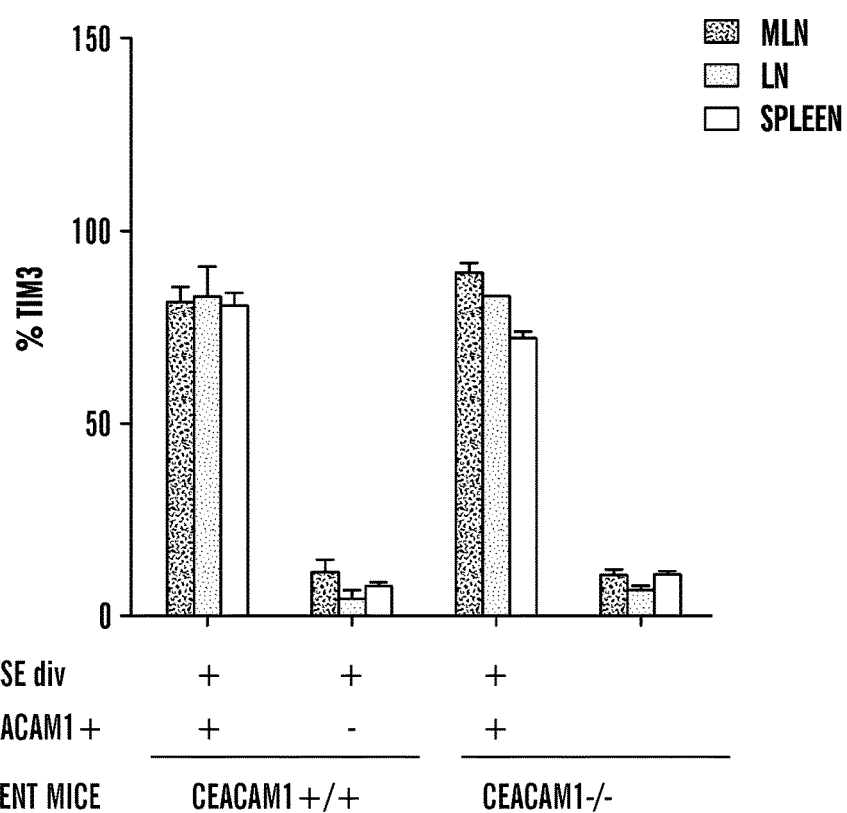

The role for CEACAM1 and TIM3 in T-cell modulation is examined in mice bearing the solid tumor CT26 colon or other solid tumors. The proportion of tumor infiltrating lymphocytes (TILs) expressing CEACAM1 or TIM3 is determined. For tumor production, $5\times10^5$ CT26 cells are implanted into the right flank of wild type Balb/c mice. Tumor surface is measured in two dimensions using a caliper. As described herein, FIG. 6 demonstrates that anti-Tim3 and anti-Ceacam1 antibodies synergize to induce tumor regression in a mouse model of cancer. Using the colorectal cell line CT26 in an in vivo mouse model, co-blockade of CEACAM1 and TIM3 relative to PD-1 and TIM3 was examined and its effects on tumor growth subcutaneously were measured. Co-blockade of CEACAM1 and TIM3 resulted in significant suppression of cancer and tumor size and growth, and exceeded that seen with co-blockade of TIM3 and PD1.

The expression of CEACAM1 and TIM3 in the spleens, peripheral blood cells, and lymphoid tissues of these mice is also examined. Tumor infiltrating lymphocytes are isolated by dissociating tumor tissue in the presence of collagenase D (25 mg/ml) for 20 min prior to centrifugation on a discontinuous PERCOLL gradient (GE Healthcare). Isolated cells are then used in various assays of T cell function. In particular, the frequency of $CD8^+$ cells that are also $CEACAM1^+$ or $TIM3^+$ is examined. Additionally, the expression of CEACAM1 and TIM3 is examined in $CD8^+$ TIL subpopulations, such as CD44 and CD62L cells. Expression of CEACAM1 and TIM3 indicates the functional states of these cells. Further, the expression (i.e., secretion) of cytokines, such as IL-2, TNFα and IFNγ can be measured ex vivo, for example by flow cytometry. Single cell suspensions are stained with antibodies against CD4 (RM4-5), CD8 (53-6.7), CD44 (IM7), CD62L (MEL-14) (BIOLEGEND), TIM3 (8B.2C12) (EBIOSCIENCE), and CD66. 7AAD is used to exclude dead cells. For intracytoplasmic cytokine staining, cells are stimulated in vitro with PMA (50 ng/ml) and ionomycin (1 μg/ml) for 3 hr in the presence of Golgi plug (BD BIOSCIENCES). Cells are then harvested and stained with CD8, TIM3 and CEACAM1 prior to fixation and permeabilization. Permeabilized cells are then stained for IL-2 (JES6-5H4), TNFα (MP6-XT22) and IFNγ (XMG1.2). All data are collected on a BD LSRII (BD Biosciences) and analyzed with FLOWJO Software (TREE STAR). For example, $CEACAM1^+TIM3^+$ cells are typically associated with TIL exhaustion, indicated by impaired IFNγ production.

Additionally, the loss of the ability to proliferate in response to TCR stimulation is among the effector functions lost in tolerant T cells. The ability of TILs to proliferate directly ex vivo is examined by determining expression of Ki-67, a nuclear protein expressed by cells that have entered into the cell cycle. It has been noted, however, that in individuals chronically infected with HIV, cells that are arrested in G1 can express Ki-67 (Combadere et al., 2000). DNA content is also examined by simultaneously staining with TO-PRO-3 iodide. By doing so, cells arrested in G1 can be discerned from cells that have progressed to S, G2 and M phase. TILs are isolated and stimulated directly ex vivo prior to examination of Ki-67 expression and DNA content. TILs are harvested and cultured in vitro in the presence of anti-CD3 (1 μg/ml) for 48 hrs. Cells are then stained with antibodies against CD8, CEACAM1, or TIM3 prior to permeabilization and staining with antibody against Ki-67 (BIOLEGEND) and with TO-PRO-3 iodide (INVITROGEN). All data are collected on a BD LSRII (BD BIOSCIENCES) and analyzed with FLOWJO software (TREE STAR). The abundance of $TIM3^+$ or CEACAM1+ cells in G0, G1 and S-M phases of cell cycle is then determined.

The discovery disclosed herein that CEACAM1 and TIM3 are ligands for each other indicates that combined targeting of these two pathways could prove to be the most efficacious means to restore anti-tumor immunity in vivo. Before commencing in vivo treatments, the expression of the CEACAM1 and TIM3 interaction on lymphocytes in CT26 tumor-bearing mice is confirmed. CT26 tumor-bearing mice are then treated with an anti-TIM3 antibody that was previously described to have blocking function in vivo (Monney et al. 2002), anti-CEACAM1 antibody (Watt et al., 2001), or both, or control immunoglobulins. For example, mice are treated with either 100 μg of anti-TIM3 antibody i.p. on days 0, 2 and 4; or 100 μg of anti-CEACAM1 antibody i.p. on days 0, 3, 6, 9 and 12, or a mixture of anti-TIM3 and anti-CEACAM1 antibodies on the same days, or isotype control immunoglobulins (Rat IgG1 and RatIgG2b). These treatments are then compared. Combined treatment with anti-TIM3 and anti-CEACAM1 can result in a dramatic reduction in tumor growth, reflected in both tumor size and efficacy among the test subjects.

The effect of anti-TIM3 plus anti-CEACAM1 treatment in mice bearing B16 melanoma is also tested, and the combined treatment can exhibit enhanced survival relative to control immunoglobulin, anti-TIM3- or anti-CEACAM1- treated mice.

To address directly whether treatment with anti-TIM3 plus anti-CEACAM1 indeed restores TILs function, TILs from mice bearing CT26 tumor are isolated and cultured in the presence of anti-TIM3 (e.g., clone 5D12), anti-CEACAM1 (e.g., 5F4), anti-TIM3 plus anti-CEACAM1 antibodies, or control immunoglobulins. TILs are harvested and cultured ($1-3\times10^5$/well) in the presence of soluble anti-CD3 (5 μg/ml) and 10 μg/ml of either anti-TIM3, anti-CEACAM1, both anti-TIM3 plus anti-CEACAM1, or control immunoglobulins (Rat IgG1 and RatIgG2b). After 96 hr, culture supernatants are collected and IFNγ measured by cytometric bead array (CBA) (BD BIOSCIENCES). Additionally, the effect of anti-TIM3 plus anti-CEACAM1 treatment on peripheral T-cell responses from tumor-bearing mice is also examined. More specifically, for instance, cells from the tumor draining lymph node of treated mice are cultured with the tumor antigen AH1 (30 μg/ml). Supernatant is collected at 48 hr, and production of IFNγ assessed.

Example 3. Experimental Autoimmune Encephalomyelitis

SJL mice are immunized with 100 μg of PLP 139-151 emulsified in either complete Freund's adjuvant (CFA) supplemented with *Mycobacterium tuberculosis* (4 mg/ml), incomplete Freund's adjuvant (IFA) containing either 100 μg of anti-TIM3, anti-CEACAM1, both anti-TIM3 and anti-CEACAM1, mouse IgG1 (EBIOSCIENCE), or IFA alone. Mice are also administered 100 ng pertussis toxin (List) intravenously on days 0 and 2. All antibodies used in vivo are LPS free. Mice are monitored daily for the development of disease, which is scored according to the following scale: 0, no clinical signs; 1, loss of tail tone; 2, hindlimb weakness; 3, hindlimb paralysis; 4, forelimb paralysis; and 5, moribund or dead. EAE symptoms are generally exacerbated by agents that inhibit T cell tolerance. In view of the discovery disclosed herein that CEACAM1 is a ligand for TIM3, it is considered that treatment with anti-TIM3 inhibitory antibody and anti-CEACAM1 inhibitory antibody, either by co-administration or in the form of a bispecific polypeptide agent, will synergistically exacerbate EAE symptoms or disease markers. In contrast, co-administration of agents that activate TIM3 and CEACAM1-mediated signaling or of a bispecific agent that activates TIM3/CEACAM-mediated signaling is contemplated to synergize for reduction of EAE symptoms or disease markers.

Cells from a mouse with EAE are stained with monoclonal antibodies against CD11b, CD45, CEACAM1, TIM3, or Rat IgG1 isotype control.

The invention claimed is:

1. A composition comprising a proteo-mimetic agent comprising SEQ ID NO: 31.

2. The composition of claim 1, wherein the proteo-mimetic agent is fused to a heterologous polypeptide, or portion thereof.

3. The composition of claim 2, wherein the heterologous polypeptide is selected from the group consisting of transferrin, serum albumin, or an immunoglobulin heavy chain constant region (Fc).

4. The composition of claim 1, wherein the proteo-mimetic agent is conjugated to a polymer.

5. The composition of claim 4, wherein the polymer is polyethylene glycol (PEG).

6. A composition comprising a fusion polypeptide comprising (a) a proteo-mimetic agent consisting of SEQ ID NO: 30; and (b) a heterologous polypeptide, or portion thereof.

7. The composition of claim 6, wherein the heterologous polypeptide is selected from the group consisting of transferrin, serum albumin, or an immunoglobulin heavy chain constant region (Fc).

8. A composition comprising a conjugate molecule comprising (a) a proteo-mimetic agent consisting of SEQ ID NO: 30; and (b) a polymer, wherein the polymer is polyethylene glycol (PEG).

* * * * *

UNITED STATES PATENT AND TRADEMARK OFFICE
CERTIFICATE OF CORRECTION

| | |
|---|---|
| PATENT NO. | : 10,513,540 B2 |
| APPLICATION NO. | : 14/418726 |
| DATED | : December 24, 2019 |
| INVENTOR(S) | : Blumberg et al. |

It is certified that error appears in the above-identified patent and that said Letters Patent is hereby corrected as shown below:

In the Specification

At Column 1, Lines 17-20:
"This invention was made with government support under Grant No. NIKDK51362, awarded by the National Institutes of Health. The government has certain rights in the invention," should be replaced with --This invention was made with government support under DK051362 awarded by the National Institutes of Health. The government has certain rights in the invention.--

Signed and Sealed this
Sixteenth Day of May, 2023

Katherine Kelly Vidal
*Director of the United States Patent and Trademark Office*